United States Patent
Sanchez et al.

(10) Patent No.: US 12,285,236 B2
(45) Date of Patent: Apr. 29, 2025

(54) METHODS AND SYSTEMS FOR GENERATING DEPTH PROFILES WITH IMPROVED OPTICAL RESOLUTION

(71) Applicant: ENSPECTRA HEALTH, INC., Mountain View, CA (US)

(72) Inventors: Gabriel Sanchez, Menlo Park, CA (US); Fred Landavazo, IV, Redwood City, CA (US); Kathryn Montgomery, Mountain View, CA (US); Piyush Arora, San Carlos, CA (US)

(73) Assignee: ENSPECTRA HEALTH, INC., Mountain View, CA (US)

( * ) Notice: Subject to any disclaimer, the term of this patent is extended or adjusted under 35 U.S.C. 154(b) by 434 days.

(21) Appl. No.: 17/317,661

(22) Filed: May 11, 2021

(65) Prior Publication Data

US 2022/0007943 A1  Jan. 13, 2022

Related U.S. Application Data

(63) Continuation of application No. PCT/US2019/061306, filed on Nov. 13, 2019.
(Continued)

(51) Int. Cl.
*A61B 5/00* (2006.01)
*G06T 7/00* (2017.01)

(52) U.S. Cl.
CPC .......... *A61B 5/0075* (2013.01); *A61B 5/0071* (2013.01); *A61B 5/0084* (2013.01);
(Continued)

(58) Field of Classification Search
CPC ......................................... A61B 5/0059–0091
See application file for complete search history.

(56) References Cited

U.S. PATENT DOCUMENTS

| | | | |
|---|---|---|---|
| 365,525 | A | 6/1887 | Lauhoff |
| 2,189,298 | A | 2/1940 | Kurt et al. |

(Continued)

FOREIGN PATENT DOCUMENTS

| | | |
|---|---|---|
| AT | 257294 T | 1/2004 |
| AU | 4145801 A | 8/2001 |

(Continued)

OTHER PUBLICATIONS

B. Masters et al, "Multiphoton Excitation Fluorescence Microscopy and Spectroscopy of In Vivo Human Skin", Biophysical Journal, vol. 72, pp. 2405-2412, Jun. 1997 (Year: 1997).*
(Continued)

*Primary Examiner* — Joel Lamprecht
*Assistant Examiner* — Nyrobi Celestine
(74) *Attorney, Agent, or Firm* — WILSON SONSINI GOODRICH & ROSATI

(57) ABSTRACT

Provided herein are methods, devices, and systems that may improve optical resolution when imaging through a thickness of samples. A method for generating a depth profile of a tissue of a subject may comprise using an optical probe to transmit an excitation light beam from a light source towards a surface of the tissue; using one or more focusing units in the optical probe to simultaneously adjust a depth and a position of a focal point of the excitation light beam along a scanning path; detecting at least a subset of the signals generated upon contacting the tissue with the excitation light beam; and using one or more computer processors programmed to process the at least the subset of the signals to generate the depth profile of the tissue.

20 Claims, 16 Drawing Sheets

Related U.S. Application Data

(60) Provisional application No. 62/760,620, filed on Nov. 13, 2018.

(52) U.S. Cl.
CPC .. *G06T 7/0012* (2013.01); *G06T 2207/10016* (2013.01); *G06T 2207/10028* (2013.01); *G06T 2207/30024* (2013.01)

(56) References Cited

U.S. PATENT DOCUMENTS

| | | |
|---|---|---|
| 3,655,259 A | 4/1972 | Miyauchi et al. |
| 4,270,843 A | 6/1981 | Goto |
| 4,416,519 A | 11/1983 | Kobayashi |
| 4,515,444 A | 5/1985 | Prescott et al. |
| 4,570,641 A | 2/1986 | Lieber et al. |
| 4,598,715 A | 7/1986 | Machler et al. |
| 4,693,606 A | 9/1987 | Podolsky et al. |
| 5,056,530 A | 10/1991 | Butler et al. |
| 5,093,719 A | 3/1992 | Prescott |
| 5,159,402 A | 10/1992 | Ortiz, Jr. |
| 5,161,063 A | 11/1992 | Krill et al. |
| 5,181,511 A | 1/1993 | Nickolls et al. |
| 5,225,676 A | 7/1993 | Matsuya |
| 5,361,166 A | 11/1994 | Atkinson et al. |
| 5,414,561 A | 5/1995 | Wakimoto et al. |
| 5,457,576 A | 10/1995 | Atkinson et al. |
| 5,880,465 A | 3/1999 | Boettner et al. |
| 5,929,985 A | 7/1999 | Sandison et al. |
| 5,987,346 A | 11/1999 | Benaron et al. |
| 5,991,090 A | 11/1999 | Strahle |
| 6,032,071 A | 2/2000 | Binder |
| 6,198,834 B1 | 3/2001 | Belk et al. |
| 6,208,886 B1 | 3/2001 | Alfano et al. |
| 6,405,070 B1 | 6/2002 | Banerjee |
| 6,485,413 B1 | 11/2002 | Boppart et al. |
| 6,542,665 B2 | 4/2003 | Reed et al. |
| 6,546,278 B2 | 4/2003 | Walsh |
| 6,571,118 B1 | 5/2003 | Utzinger et al. |
| 6,580,941 B2 | 6/2003 | Webb et al. |
| 6,639,674 B2 | 10/2003 | Sokolov et al. |
| 6,643,071 B2 | 11/2003 | Schnitzer |
| 6,697,652 B2 | 2/2004 | Georgakoudi et al. |
| 6,760,112 B2 | 7/2004 | Reed et al. |
| 6,766,184 B2 | 7/2004 | Utzinger et al. |
| 6,785,471 B2 | 8/2004 | Lee et al. |
| 6,795,199 B2 | 9/2004 | Suhami |
| 6,839,483 B2 | 1/2005 | Reed et al. |
| 6,839,586 B2 | 1/2005 | Webb |
| 6,839,596 B2 | 1/2005 | Nelson et al. |
| 6,870,613 B1* | 3/2005 | Tisone ............... G01J 3/4406 356/317 |
| 6,889,075 B2 | 5/2005 | Marchitto et al. |
| 6,912,412 B2 | 6/2005 | Georgakoudi et al. |
| 6,967,725 B2 | 11/2005 | Denk et al. |
| 7,091,500 B2 | 8/2006 | Schnitzer |
| 7,307,774 B1 | 12/2007 | Schnitzer et al. |
| 7,336,988 B2 | 2/2008 | Schnitzer |
| 7,336,990 B2 | 2/2008 | Genet et al. |
| 7,414,729 B2 | 8/2008 | Xie et al. |
| 7,485,100 B2 | 2/2009 | Garcia-Webb et al. |
| 7,616,986 B2 | 11/2009 | Seibel et al. |
| 7,702,381 B2 | 4/2010 | Gaeta et al. |
| 8,068,899 B2 | 11/2011 | Llewellyn et al. |
| 8,259,167 B2 | 9/2012 | Ishiwata et al. |
| 8,380,268 B2 | 2/2013 | Georgakoudi et al. |
| 8,496,579 B2 | 7/2013 | Koenig et al. |
| 8,788,021 B1 | 7/2014 | Flusberg et al. |
| 8,807,801 B2 | 8/2014 | Oldham et al. |
| 8,897,858 B2 | 11/2014 | Sanchez et al. |
| 8,912,511 B2 | 12/2014 | Schoenborn et al. |
| 8,941,087 B2 | 1/2015 | Sun et al. |
| 9,055,866 B2 | 6/2015 | Narita et al. |
| 9,411,149 B2 | 8/2016 | Flusberg et al. |
| 9,433,350 B2 | 9/2016 | Schönborn et al. |
| 9,433,351 B2 | 9/2016 | Yu et al. |
| 9,636,020 B2 | 5/2017 | Flusberg et al. |
| 9,763,577 B2 | 9/2017 | Lee et al. |
| 9,846,121 B2 | 12/2017 | Schönborn et al. |
| 9,851,303 B2 | 12/2017 | Huber et al. |
| 9,983,127 B2 | 5/2018 | Liu et al. |
| 10,445,879 B1 | 10/2019 | Fuchs et al. |
| 10,460,150 B2 | 10/2019 | Jackson et al. |
| 10,499,797 B2 | 12/2019 | Sanchez et al. |
| 11,172,826 B2 | 11/2021 | Sanchez et al. |
| 11,633,149 B2 | 4/2023 | Sanchez et al. |
| 11,877,826 B2 | 1/2024 | Sanchez et al. |
| 2002/0139920 A1 | 10/2002 | Seibel et al. |
| 2002/0140942 A1 | 10/2002 | Fee et al. |
| 2002/0141714 A1 | 10/2002 | Reed et al. |
| 2002/0146202 A1 | 10/2002 | Reed et al. |
| 2003/0025913 A1* | 2/2003 | Izatt ............... G01B 9/0201 356/497 |
| 2003/0031410 A1 | 2/2003 | Schnitzer |
| 2003/0103262 A1 | 6/2003 | Descour et al. |
| 2003/0117715 A1 | 6/2003 | Schnitzer |
| 2003/0118305 A1 | 6/2003 | Reed et al. |
| 2003/0220549 A1 | 11/2003 | Liu et al. |
| 2003/0236458 A1 | 12/2003 | Hochman |
| 2004/0036838 A1 | 2/2004 | Podoleanu et al. |
| 2004/0051957 A1 | 3/2004 | Liang |
| 2004/0064053 A1 | 4/2004 | Chang et al. |
| 2004/0143190 A1 | 7/2004 | Schnitzer |
| 2004/0249305 A1 | 12/2004 | Reeves et al. |
| 2004/0254457 A1 | 12/2004 | Van Der Weide |
| 2004/0254474 A1* | 12/2004 | Seibel ............... G02B 21/0036 600/478 |
| 2004/0260148 A1 | 12/2004 | Schnitzer |
| 2004/0263959 A1 | 12/2004 | Dixon et al. |
| 2005/0038486 A1 | 2/2005 | Mulholland |
| 2005/0157981 A1 | 7/2005 | Berier et al. |
| 2005/0207668 A1 | 9/2005 | Perchant et al. |
| 2005/0242298 A1 | 11/2005 | Genet et al. |
| 2007/0038120 A1 | 2/2007 | Richards-Kortum et al. |
| 2007/0057211 A1 | 3/2007 | Bahlman et al. |
| 2007/0159673 A1 | 7/2007 | Freeman et al. |
| 2007/0167835 A1 | 7/2007 | Yu et al. |
| 2007/0263226 A1 | 11/2007 | Kurtz et al. |
| 2007/0283953 A1 | 12/2007 | Angelini et al. |
| 2007/0290145 A1 | 12/2007 | Viellerobe et al. |
| 2008/0192236 A1* | 8/2008 | Smith ............... A61B 5/6852 356/73 |
| 2008/0205833 A1 | 8/2008 | Fu et al. |
| 2008/0225388 A1 | 9/2008 | Hirata |
| 2008/0232667 A1 | 9/2008 | Kitamura et al. |
| 2008/0297922 A1 | 12/2008 | Lule |
| 2009/0012406 A1 | 1/2009 | Llewellyn et al. |
| 2009/0015785 A1 | 1/2009 | Blum et al. |
| 2009/0021724 A1 | 1/2009 | Mahadevan-Jansen et al. |
| 2009/0073455 A1 | 3/2009 | Onimura |
| 2009/0097108 A1 | 4/2009 | Fox et al. |
| 2009/0257065 A1 | 10/2009 | Hauger et al. |
| 2009/0323059 A1 | 12/2009 | Sun et al. |
| 2010/0110568 A1 | 5/2010 | Margolis |
| 2010/0177389 A1 | 7/2010 | Rouyer |
| 2010/0286674 A1 | 11/2010 | Ben-Yakar et al. |
| 2010/0290042 A1 | 11/2010 | Vakhshoori et al. |
| 2011/0117025 A1 | 5/2011 | Dacosta et al. |
| 2011/0125029 A1 | 5/2011 | Wang et al. |
| 2011/0128373 A1 | 6/2011 | Goldberg |
| 2011/0152744 A1 | 6/2011 | Choi et al. |
| 2011/0229640 A1 | 9/2011 | Lee et al. |
| 2011/0229840 A1 | 9/2011 | Liang et al. |
| 2012/0080616 A1 | 4/2012 | Schoenborn |
| 2012/0143065 A1 | 6/2012 | Sanchez et al. |
| 2012/0184827 A1 | 7/2012 | Shwartz et al. |
| 2012/0261551 A1 | 10/2012 | Rogers |
| 2012/0281265 A1 | 11/2012 | Zhang et al. |
| 2012/0327423 A1* | 12/2012 | Hanebuchi ......... G01B 9/02019 356/497 |
| 2013/0063727 A1 | 3/2013 | Xu |
| 2013/0070249 A1 | 3/2013 | Choi et al. |
| 2013/0079236 A1 | 3/2013 | Holmes |

(56) References Cited

U.S. PATENT DOCUMENTS

| | | |
|---|---|---|
| 2013/0211391 A1 | 8/2013 | Benyakar et al. |
| 2014/0023993 A1 | 1/2014 | Zeng et al. |
| 2014/0104619 A1 | 4/2014 | Nebosis |
| 2014/0187879 A1 | 7/2014 | Wood et al. |
| 2014/0187931 A1 | 7/2014 | Wood et al. |
| 2014/0187967 A1 | 7/2014 | Wood et al. |
| 2014/0213897 A1 | 7/2014 | Iftimia et al. |
| 2014/0276102 A1 | 9/2014 | Lee et al. |
| 2014/0276103 A1 | 9/2014 | Lee et al. |
| 2015/0062573 A1* | 3/2015 | Liu ............ A61B 5/444 356/300 |
| 2015/0141846 A1 | 5/2015 | Sanchez et al. |
| 2015/0157254 A1 | 6/2015 | Sun et al. |
| 2015/0164327 A1 | 6/2015 | Yaroslavsky et al. |
| 2015/0238089 A1 | 8/2015 | Fujinuma et al. |
| 2015/0260978 A1 | 9/2015 | Cremer et al. |
| 2015/0265155 A1 | 9/2015 | Zalev et al. |
| 2015/0317509 A1 | 11/2015 | Kil |
| 2015/0335385 A1 | 11/2015 | Miao et al. |
| 2016/0022178 A1 | 1/2016 | Wang et al. |
| 2016/0139388 A1 | 5/2016 | Asundi et al. |
| 2016/0253466 A1 | 9/2016 | Agaian et al. |
| 2016/0274346 A1 | 9/2016 | Chiang et al. |
| 2016/0317037 A1 | 11/2016 | Lee et al. |
| 2016/0320299 A1 | 11/2016 | Huang et al. |
| 2016/0320837 A1 | 11/2016 | Swedish et al. |
| 2016/0374857 A1 | 12/2016 | Fu et al. |
| 2016/0377546 A1 | 12/2016 | Ragan et al. |
| 2017/0010456 A1 | 1/2017 | Gopinath et al. |
| 2017/0049381 A1 | 2/2017 | Lieber et al. |
| 2017/0071467 A1* | 3/2017 | Raymond ............ A61B 3/107 |
| 2017/0143196 A1 | 5/2017 | Liang et al. |
| 2017/0209049 A1 | 7/2017 | Wang et al. |
| 2017/0234675 A1 | 8/2017 | Iddan et al. |
| 2017/0281077 A1 | 10/2017 | Pyun et al. |
| 2017/0284940 A1 | 10/2017 | Butte et al. |
| 2017/0319147 A1 | 11/2017 | Wang et al. |
| 2018/0028079 A1 | 2/2018 | Gurevich et al. |
| 2018/0110971 A1 | 4/2018 | Serrano Carmona |
| 2018/0228552 A1 | 8/2018 | Milner et al. |
| 2019/0129026 A1 | 5/2019 | Sumi et al. |
| 2019/0133452 A1 | 5/2019 | Sanchez et al. |
| 2019/0287246 A1 | 9/2019 | Pfister |
| 2020/0100659 A1 | 4/2020 | Sanchez et al. |
| 2020/0196938 A1 | 6/2020 | Sanchez et al. |
| 2021/0169336 A1 | 6/2021 | Sanchez et al. |
| 2024/0206734 A1 | 6/2024 | Sanchez et al. |
| 2024/0217832 A1 | 7/2024 | Snydacker et al. |
| 2025/0009231 A1 | 1/2025 | Sanchez et al. |

FOREIGN PATENT DOCUMENTS

| | | |
|---|---|---|
| AU | 2002364332 A1 | 7/2003 |
| AU | 2004297876 A1 | 6/2005 |
| AU | 2007219364 A1 | 4/2008 |
| AU | 2010261751 B2 | 5/2015 |
| AU | 2014236561 B2 | 8/2018 |
| BR | 9911603 A | 2/2001 |
| CA | 2398029 A1 | 8/2001 |
| CA | 2535843 A1 | 6/2005 |
| CA | 2906056 A1 | 9/2014 |
| CA | 2765620 C | 1/2018 |
| CN | 1303539 A | 7/2001 |
| CN | 102933137 A | 2/2013 |
| CN | 105473051 A | 4/2016 |
| DE | 19823955 A1 | 12/1999 |
| DE | 102006046925 A1 | 4/2008 |
| DE | 102009024943 A1 | 12/2010 |
| DE | 102009029831 A1 | 1/2011 |
| EP | 0594388 A1 | 4/1994 |
| EP | 1259163 A2 | 11/2002 |
| EP | 1082816 B1 | 1/2004 |
| EP | 1994874 A1 | 11/2008 |
| EP | 1929939 B1 | 12/2014 |
| EP | 2440119 B1 | 5/2015 |
| EP | 1664854 B1 | 7/2015 |
| EP | 2932892 A1 | 10/2015 |
| EP | 2443503 B1 | 12/2015 |
| EP | 2953215 A1 | 12/2015 |
| EP | 2967280 A2 | 1/2016 |
| EP | 3087423 A1 | 11/2016 |
| EP | 3095001 A2 | 11/2016 |
| EP | 3097443 A1 | 11/2016 |
| EP | 3171766 A1 | 5/2017 |
| EP | 1461601 B1 | 8/2017 |
| EP | 3273285 A1 | 1/2018 |
| ES | 2214875 T3 | 9/2004 |
| ES | 2544804 T3 | 9/2015 |
| ES | 2564529 T3 | 3/2016 |
| ES | 2647468 T3 | 12/2017 |
| FR | 2834340 B1 | 7/2004 |
| JP | 2002517117 A | 6/2002 |
| JP | 2003052642 A | 2/2003 |
| JP | 2003052699 A | 2/2003 |
| JP | 2004500197 A | 1/2004 |
| JP | 2005515434 A | 5/2005 |
| JP | 2006079000 A | 3/2006 |
| JP | 2007503851 A | 3/2007 |
| JP | 2007532982 A | 11/2007 |
| JP | 2008100057 A | 5/2008 |
| JP | 2008539436 A | 11/2008 |
| JP | 2011215061 A | 10/2011 |
| JP | 2011257215 A | 12/2011 |
| JP | 2016520339 A | 7/2016 |
| JP | 2017502300 A | 1/2017 |
| JP | 2017504836 A | 2/2017 |
| JP | 2017525435 A | 9/2017 |
| KR | 20160037834 A | 4/2016 |
| KR | 20170038024 A | 4/2017 |
| NZ | 520257 A | 10/2005 |
| RU | 2235420 C2 | 8/2004 |
| TW | 201634901 A | 10/2016 |
| TW | 201740101 A | 11/2017 |
| UA | 44939 C2 | 3/2002 |
| WO | WO-9962176 A1 | 12/1999 |
| WO | WO-0159423 A2 | 8/2001 |
| WO | WO-03060493 A1 | 7/2003 |
| WO | WO-2005057244 A2 | 6/2005 |
| WO | WO-2007000165 A1 | 1/2007 |
| WO | WO-2007014213 A2 | 2/2007 |
| WO | WO-2007105495 A1 | 9/2007 |
| WO | WO-2009157229 A1 | 12/2009 |
| WO | WO-2010142672 A1 | 12/2010 |
| WO | WO-2010146134 A2 | 12/2010 |
| WO | WO-2010146134 A3 | 3/2011 |
| WO | WO-2011028595 A2 | 3/2011 |
| WO | WO-2013082156 A1 | 6/2013 |
| WO | WO-2014012110 A2 | 1/2014 |
| WO | WO-2014137357 A1 | 9/2014 |
| WO | WO-2014152389 A1 | 9/2014 |
| WO | WO-2014152797 A2 | 9/2014 |
| WO | WO-2015002614 A1 | 1/2015 |
| WO | WO-2015054666 A1 | 4/2015 |
| WO | WO-2015100421 A1 | 7/2015 |
| WO | WO-2015109323 A2 | 7/2015 |
| WO | WO-2015112770 A1 | 7/2015 |
| WO | WO-2015168594 A1 | 11/2015 |
| WO | WO-2015185620 A1 | 12/2015 |
| WO | WO-2016015052 A1 | 1/2016 |
| WO | WO-2016145633 A1 | 9/2016 |
| WO | WO-2017139716 A1 | 8/2017 |
| WO | WO-2017156182 A1 | 9/2017 |
| WO | WO-2017173315 A1 | 10/2017 |
| WO | WO-2018018160 A1 | 2/2018 |
| WO | WO-2018201082 A1 | 11/2018 |
| WO | WO-2018204748 A1 | 11/2018 |
| WO | WO-2020102442 A1 | 5/2020 |
| WO | WO-2021097142 A1 | 5/2021 |

OTHER PUBLICATIONS

A. Pena et al, "Chiroptical Effects in the Second Harmonic Signal

(56) References Cited

OTHER PUBLICATIONS of Collagens I and IV", Journal of the American Chemical Society, vol. 127, No. 29, pp. 10314-10322, 2005 (Year: 2005).*
F. Stracke et al, "Multiphoton Microscopy for the Investigation of Dermal Penetration of Nanoparticle-Borne Drugs", Journal of Investigative Dermatology, vol. 126, pp. 2224-2233, May 2006 (Year: 2006).*
T. Le et al, "Label-free molecular imaging of atherosclerotic lesions using multimodal nonlinear optical microscopy", Journal of Biomedical Optics, vol. 12, No. 5, pp. 1-10, Oct. 2007 (Year: 2007).*
P. Campagnola, "Second Harmonic Generation Imaging Microscopy: Applications to Diseases Diagnostics", Analytical Chemistry, vol. 83, pp. 3224-3231, Mar. 2011 (Year: 2011).*
M. Roberts et al, "Non-invasive imaging of skin physiology and percutaneous penetration using fluorescence spectral and lifetime imaging with multiphoton and confocal microscopy", European Journal of Pharmaceutics and Biopharmaceutics, vol. 77, pp. 469-488, 2011 (Year: 2011).*
Y. Dancik et al, "Use of multiphoton tomography and fluorescence lifetime imaging to investigate skin pigmentation in vivo", Journal of Biomedical Optics, vol. 18, No. 2, pp. 1-13, Feb. 2013 (Year: 2013).*
S. Seidenari et al, "Multiphoton Laser Microscopy with Fluorescence Lifetime Imaging and Skin Cancer", Skin Cancer, pp. 279-290, 2015 (Year: 2015).*
M. Balu et al, "Rapid mesoscale multiphoton microscopy of human skin", Biomedical Optics Express, vol. 7, No. 11, pp. 4375-4387, Nov. 2016 (Year: 2016).*
Co-pending U.S. Application No. 202117495717, inventors Sanchez; Gabriel et al., filed on Oct. 6, 2021.
U.S. Appl. No. 16/585,789 Office Action dated Feb. 23, 2022.
U.S. Appl. No. 16/662,830 Supplemental Notice of Allowability dated Mar. 24, 2023.
U.S. Appl. No. 17/495,717 Notice of Allowance dated May 4, 2023.
EP19885962.1 Extended European Search Report dated Jun. 20, 2022.
U.S. Appl. No. 16/662,830 Office Action dated May 20, 2022.
PCT/US2020/060302 International Search Report and Written Opinion dated Mar. 9, 2021.
U.S. Appl. No. 16/662,830 Notice of Allowance dated Dec. 13, 2022.
U.S. Appl. No. 16/585,789 Final Office Action dated Oct. 14, 2022.
U.S. Appl. No. 17/096,602 Office Action dated Nov. 7, 2022.
U.S. Appl. No. 17/495,717 Office Action dated Nov. 8, 2022.
Anderson, et al., Contributions of muscle forces and tow-off kinematics to peak knee flexion during the swing phase of normal gait: an induced position analysis, Journal of Biomechanics, 37:731-737 (2004).
Armstrong, et al., In vivo size and shape measurement of the human upper airway using endoscopic longrange optical coherence tomography, Opt. Express, 11:1817-26 (2003).
Botcherby, et al. Fast measurement of sarcomere length and cell orientation in Langendorff-perfused hearts using remote focusing microscopy. Circ Res. Sep. 13, 2013;113(7):863-70. doi: 10.1161/CIRCRESAHA.113.301704. Epub Jul. 30, 2013.
Boulesteix, et al., Second-harmonic Microscopy of Unstained Living Cardiac Myocytes: Measurements of sarcomere length with 20-nm accuracy, Optics Letters, Sep. 1, 2004, 29(17):2031-33.
Brown, et al., Dynamic imaging of collagen and its modulation in tumors in vivo using second-harmonic generation, Nature Medicine, 9:796-800 (2003).
Campagnola, et al., Nonlinear Optical Spectroscopy, Optics & Photonics News, Jun. 2003, pp. 40-45.
Campagnola, et al. Three-dimensional high-resolution second-harmonic generation imaging of endogenous structural proteins in biological tissues. Biophysical Journal. 2002; 81:493-508.
Chu, et al., Studies of X(2)/X(3) Tensors in Submicron-Scaled Bio-Tissues by Polarization Harmonics Opticaln Microscopy, Biophysical Journal, 86: 3914-22 (Jun. 2004).

Delp, et al., An Interactive Graphics-based Model of the Lower Extremity to Study Orthopedic Surgical Procedures, IEEE Trans Biomed Eng., 37: 757-767. (1990).
Delp, et al., Open Sim: Open-Source Software to create and analyze dynamic simulations of movement, Biomedical Engineering IEEE, 54: 1940-50 (Nov. 2007) Abstract Only.
Dutton, H. Understanding Optical Communications, IBM, International Technical Support Organization Sep. 1998. Available at http://www.redbooks.ibm.com.
Edman, et al., Depression of tetanic force induced by loaded shortening of frog muscle fibres, J Physiol., 466: 535-552 (1993).
EP 20199801.0European Search Report, dated Jun. 11, 2021, 8 pages.
EP12853081.3 Examination Report dated Mar. 27, 2020.
EP12853081.3 Examination Report dated Nov. 9, 2017.
EP17764041.4 The Extended European Search Report dated Sep. 25, 2019.
EP18791038.5 The Extended European Search Report dated Dec. 22, 2020.
EPO. European Patent Application No. 12853081, European Search Report. (Jul. 1, 2015).
EPO. European Patent Application No. 12853081.3, Examination Report, 6 pgs. (Nov. 24, 2016).
Flusberg, et al., In Vivo Brain Imaging Using a Portable 3.9 Gram Two-photon Fluorescence Microendoscope, Optics Letters 30(17):2272-74 (Sep. 2005).
Freund, et al., Connective Tissue Polarity: Optical Second-harmonic Microscopy, Crossed-beam Summation, and Small-angle Scattering in Rat-tail Tendon, Biophysical Journal, 50: 693-712 (Oct. 1986).
Friden, et al., Physiologic consequences of surgical lengthening of extensor carpi radialis brevis muscle-tendon junction for tennis elbow, J Hand Surg., 19: 269-274 (1994). Abstract Only.
Fu, et al., Integration of a Double-clad Photonic Crystal Fiber, a GRIN lens and a MEMS mirror for nonlinear optical endoscopy, BIO Meeting, Fort Lauderdale (Mar. 19, 2006).
Fu, et al., Nonlinear optical endoscopy based on a double clad photonic crystal fiber and a MEMS mirror, Optics Express, 14(3): 1027-32 (Feb. 2006).
Gobel, et al. New angles on neuronal dendrites in vivo. J Neurophysiol. Dec. 2007;98(6):3770-9. Epub Sep. 26, 2007.
Gollapudi, et al., Experimental determination of sarcomere force-length relationship in type-1 human skeletal muscle fibers, J Biomech 42, pp. 2011-2016 (2009) Abstract Only.
Gordon, et al., The variation in isometric tension with sarcomere length in vertebrate muscle fibers, J Physiol, 184: 170-92. (1966).
Guo, et al., Second-harmonic Tomography of Tissues, Optics Letters, Sep. 1, 1997, 22(17):1323-25.
Guo, et al., Subsurface tumor progression investigated by noninvasive optical second harmonic tomography, Proc. Nat'l. Academy of Science, Sep. 1999, 96: 10854-856.
Helmchen, et al., Deep Tissue two-photon microscopy, Nature Methods, 2(12):932-940 (Dec. 2005).
Imaging and Optical technology at Aberdeen, Optics and Laser Technology 25(6), pp. 399-405 (1993).
Infantolino, et al., Individual sarcomere lengths in whole muscle fibers and optimal fiber length computation, Analrec (Hoboken) 293, pp. 1913-1919 (2010).
International search report and written opinion dated Jul. 26, 2017 for PCT Application No. US-201721439.
Julian, et al., Intersarcomere dynamics during fixed-end tetanic contractions of frog muscle fibres, J Physiol., 293: 365-78 (1979).
Julian, et al., Sarcomere length-tension relations of frog skinned muscle fibres at lengths above the optimum, J Physiol., 304: 529-39 (1980).
Jung, et al., In vivo mammalian brain imaging using one- and two-photon fluorescence microendoscopy, J. Neurophysiol, 92:3121-33 (May 2004).
Jung, et al. Miniaturized probe using 2 axis MEMS scanner for endoscopic multiphoton excitation microscopy. Proceedings of SPIE—The International Society for Optical Engineering, vol. 6851, Mar. 2008, pp. 1-7.
Jung, et al., Multiphoton endoscopy, Optics Letters, 28(11):902-904 (Jun. 2003).

(56) References Cited

OTHER PUBLICATIONS

Koch, G. MEMS-based scanning device facilitates microendoscopy. Optics Letters, Jul. 1, 2006. pp. 1-3, Online: http://www.photonics.com/Article.aspx?AID=43392, Accessed Feb. 20, 2016.
Konig, et al., High-resolution multiphoton tomography of human skin with subcellular spatial resolution and picosecond lime resolution, Society of Photo-Optical Instrum Engineers. (2003) Abstract Only.
Lee, et al., Integrated semiconductor optical sensor for chronic, minimally-invasive imaging of brain functions, Proceedings of the 28th IEEE, pp. 1025-1028 (Aug.-Sep. 2006).
Levene, et al., In vivo multiphoton microscopy of deep brain tissue, J. Neurophysiol, 91: 1908-12 (Dec. 2003).
Lieber, et al., Biomechanical properties of the brachioradialis muscle: Implications for surgical tendon transfer, The Journal of Hand Surgery, 30A(2):273-282 (Mar. 2005).
Lieber, et al., In Vivo Measurement of Human Wrist Extensor Muscle Sarcomere Length Changes, Journal of Neurophysiology, 71(3): 874-881 (Mar. 1994).
Lieber, et al., Sarcomere length in wrist extensor muscles, Changes may provide insights into the etiology of chronic lateral epicondylitis, Acta Orthop Scand, 68:249-254 (1997).
Ljung, et al., Sarcomere length varies with wrist ulnar deviation but not forearm pronation in the extensor carpi radialis brevis muscle, J Biomech., 32:199-202 (1999).
Llewellyn, et al., Minimally invasive high-speed imaging of sarcomere contractile dynamics in mice and humans, Nature 454, 784-788 (2008).
Manal, et al. A real-time EMG-driven virtual arm, Comput. Bioi. Med., 32(1):25-26 (Jan. 2002) Abstract Only.
Mertz, et al., Second-harmonic generation by focused excitation of in homogeneously distributed scatterers, Optics Communications 196: 325-330 (2001).
Mertz, Nonlinear microscopy: New techniques and applications, Current Opinion in Neurobiology, 14:610-616 (2004).
Messerschmidt, et al., Novel concept of GRIN optical systems for high resolution microendoscopy. Part 1: Physical aspects, Proc. of SPIE 6432, pp. 643202-1-643202-9 (2007).
Mohler, et al., Second-harmonic generation imaging of endogenous structural proteins, Methods, 29:97-109 (2003).
Monfared, et al., In Vivo Imaging of Mammalian Cochlear Blood Flow Using Fluorescence Microendoscope, Otology and Neurotology, 27:144-152 (2006).
Moreaux, et al., Coherent Scattering in Multi-Harmonic Light Microscopy, Biophysical Journal, 80: 1568-74 (Mar. 2001).
Murray, et al., Variability in surgical technique for brachioradialis tendon transfer, Evidence and implications, J Bone Joint Surg. Am., 88: 2009-16 (2006).
Niell, et al., Live Optical Imaging of Nervous System Development, Annu. Rev. Physiol., 66:771-798 and C1-C5 (2004).
Nucciotti, et al., Functional imaging of muscle cells by Second Harmonic Generation, Proc. of SPIE, 6089: 608911-1-608911-8 (2006).
Office Action dated Nov. 3, 2017 for U.S. Appl. No. 14/546,085.
Office action dated Jan. 27, 2017 for U.S. Appl. No. 14/546,085.
Olivier, et al. Cell lineage reconstruction of early zebrafish embryos using label-free nonlinear microscopy. Science. Aug. 20, 2010;329(5994):967-71. doi: 10.1126/science.1189428.
Panchangam, et al., A novel optical imaging system for investigating sarcomere dynamics in single skeletal muscle fibers, Proc. of SPIE, 6088: 608808-1-608808-11 (2006).
PCT/US12/66860 International Search Report and Written Opinion dated Apr. 17, 2013.
PCT/US2018/030011 International Search Report and Written Opinion dated Aug. 14, 2018.
PCT/US2019/061306 International Search Report dated Mar. 9, 2020.
Plotnikov, et al., Characterization of the Myosin-based source for Second-Harmonic Generation from muscle sarcomeres, Biophysical Journal, 90:693-703 (Jan. 2006).
Plotnikov, et al., Measurement of muscle disease by quantitative second-harmonic generation imaging, J. Biomed. Opt. 13 (Aug. 2008) Abstract Only.
Plotnikov, et al., Optical Clearing for Improved Contrast in Second Harmonic Generation Imaging of Skeletal Muscle, Biophysical Journal, 90:328-339 (Jan. 2006).
Ponten, et al., Intraoperative muscle measurements reveal a relationship between contracture formation and muscle remodeling, Muscle & Nerve 36, pp. 47-54 (Jul. 2007).
Rothstein, et al., Multi-photon excitation microscopy in intact animals, Journal of Microscopy, 22:58-64 (2006).
Rothstein, et al., Skeletal Muscle NAD(P)H Two-photon fluorescence microscopy in vivo: Topology and Optical inner filters, Biophysical Journal, 88: 2165-76 (Mar. 2005).
Schenkl, et al., Applications of rigid and flexible GRIN-endoscopes, Proc. of SPIE 6433, pp. 64330N-1-64330N-7 (2007).
Shaw, et al., Infrared spectroscopy of dystrophic mdx mouse muscle tissue distinguishes among treatment groups, J. Applied Physiol. 81: 2328-2335 (1996).
Smith, et al., Hamstring contractures in children with spastic cerebral palsy result from a stiffer extracellular matrix and increased in vivo sarcomere length, J Physiol., 589: 2625-2639. (2011).
U.S. Appl. No. 16/123,447 Notice of Allowance dated Aug. 11, 2021.
U.S. Appl. No. 16/123,447 Office Action dated Dec. 10, 2020.
U.S. Appl. No. 14/546,085 Notice of Allowance dated Jul. 22, 2019.
U.S. Appl. No. 14/546,085 Office Action dated Feb. 26, 2016.
U.S. Appl. No. 14/546,085 Office Action dated Jun. 8, 2016.
U.S. Appl. No. 14/546,085 Office Action dated Oct. 10, 2018.
Williams, et al., Interpreting Second-Harmonic Generation Images of Collagen I Fibrils, Biophysical Journal, 88:1377-86 (Feb. 2005).
Zipfel, et al., Live tissue intrinsic emission microscopy using multiphoton-excited native fluorescence and second harmonic generation, PNAS 100(12):7075-80 (Jun. 2003).
Zoumi, et al., Imaging cells and Extracellular Matrix in vivo by using Second-harmonic Generation and two-photon excited fluorescence, PNAS, Aug. 20, 2002, 99(17):11014-19.
Abuzaghleh et al. Noninvasive Real-Time Automated Skin Lesion Analysis System for Melanoma Early Detection and Prevention. Oncology, IEEE Journal of Translational Engineering in Health and Medicine, vol. 3 (2015). 12 pages.
U.S. Appl. No. 16/585,789 Office Action dated Aug. 1, 2023.
U.S. Appl. No. 17/096,602 Final Office Action dated Jul. 7, 2023.
Co-pending U.S. Appl. No. 18/404,020, inventors Sanchez; Gabriel et al., filed on Jan. 4, 2024.
PCT/US2019/061306 International Search Report and Written Opinion dated Mar. 9, 2020.
U.S. Appl. No. 17/096,602 Office Action dated Jul. 7, 2023.
U.S. Appl. No. 18/363,854 Office Action dated Apr. 23, 2024.
U.S. Appl. No. 16/585,789 Office Action dated Jan. 22, 2025.

* cited by examiner

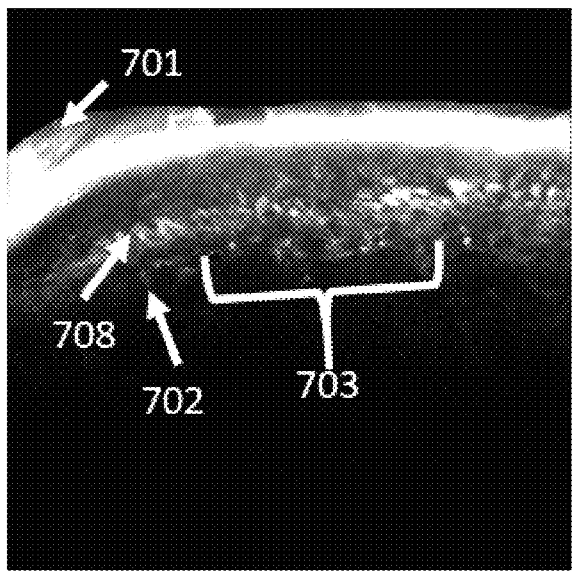
*FIG. 7A*
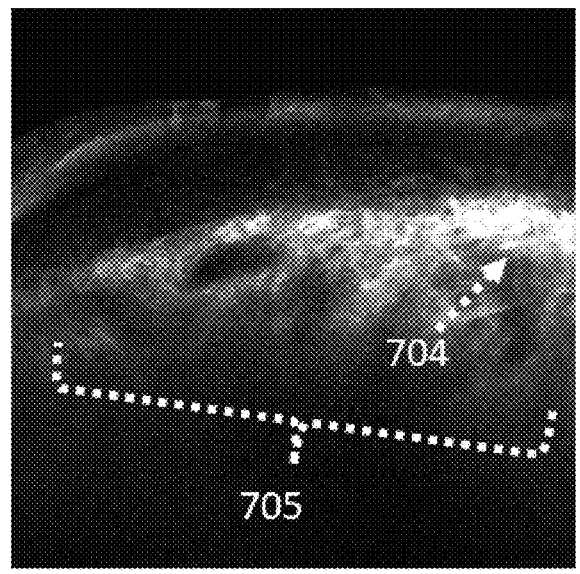
*FIG. 7B*
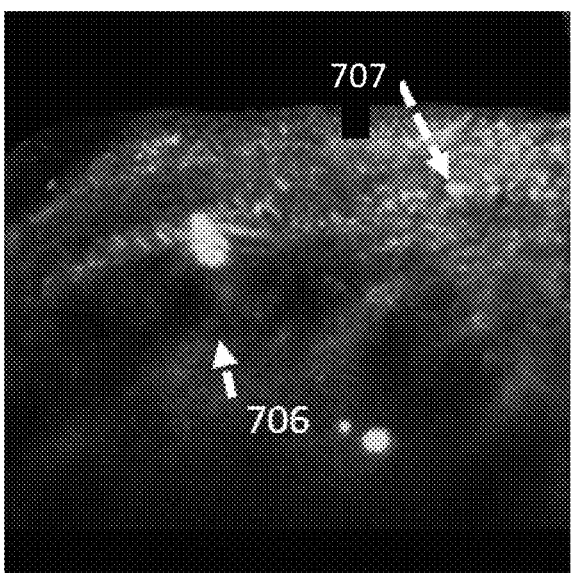
*FIG. 7C*
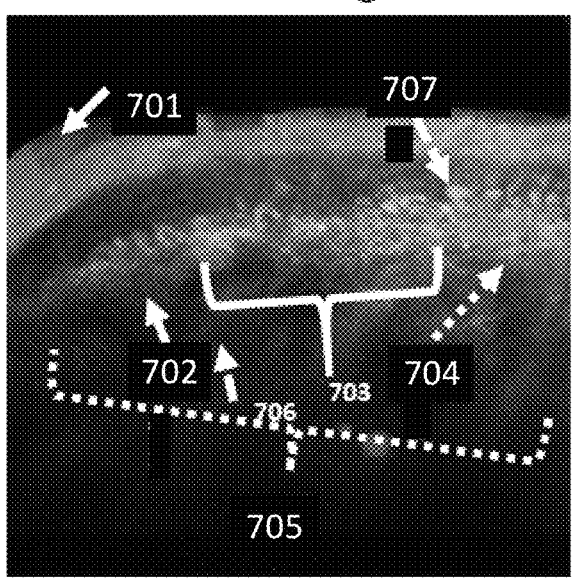
*FIG. 7D*
*FIG. 7*

METHODS AND SYSTEMS FOR GENERATING DEPTH PROFILES WITH IMPROVED OPTICAL RESOLUTION

CROSS-REFERENCE

This application is a continuation of International Patent Application No. PCT/US2019/061306, filed Nov. 13, 2019, which claims the benefit of U.S. Provisional Patent Application No. 62/760,620, filed Nov. 13, 2018, which is entirely incorporated herein by reference.

GOVERNMENT INTEREST STATEMENT

This invention was made with U.S. Government support under Small Business Innovation Research (SBIR) grant number 2R44CA221591-02A1 awarded by the Department of Health and Human Services, National Institutes of Health, and National Cancer Institute. The U.S. Government has certain rights in the invention.

BACKGROUND

Imaging devices that utilize point scanning excitation like non-linear microscopy, two-photon, three-photon, multi-photon, Confocal, Raman, Coherent anti-Stokes Raman spectroscopy, Optical Coherence Tomography (OCT) may be optically limited in their resolution in the direction parallel to the optical axis but perpendicular to the surface of the imaged sample.

Diffraction may prevent focusing light to an actual point but create a concentrated region of light called the point spread function (PSF). In three dimensions, the PSF may be an ellipsoid that is elongated in the Z direction (the direction parallel to the optical axis) relative to the XY plane. The size of the PSF may dictate the smallest feature that the system can resolve, for example, the system's imaging resolution. The PSF may be several times longer in the XZ/YZ planes (axial resolution) than that in the XY plane (lateral resolution). This effect may degrade image quality when attempting to image a cross section through the sample. The PSF size can be reduced by increasing the numerical aperture (NA) of the optical system, but the trend may remain that the PSF is longer in the Z direction than either the X or Y direction. When imaging within an immersion medium with refractive index near 1.5, the ratio between the axial PSF dimension to the lateral PSF dimension may be approximately 5/NA. Therefore, at an NA of 1.0, the axial PSF dimension may be five times larger than the lateral PSF dimension. This stretching of the PSF may increase for NA values below 1.0. For instance, at an NA of 0.7, the lateral resolution may be approximately 0.7 µm for excitation wavelengths in the near infrared spectrum for diffraction limited optical systems. In such a system, the axial resolution may be greater than 4 µm, which may be about six times worse than the lateral plane resolution. System constraints such as aberrations, lens diameters, and working distances may limit the practical NA that can be achieved.

SUMMARY

Provided herein are methods and apparatuses that may improve optical resolution when imaging through the thickness of samples. Further provided herein are methods and apparatuses that may improve disease diagnosis.

In an aspect, the present disclosure provides a method for generating a depth profile of a tissue of a subject, comprising (a) using an optical probe to transmit an excitation light beam from a light source to a surface of the tissue, which pulses of the excitation light beam, upon contacting the tissue, yield signals indicative of an intrinsic property of the tissue, wherein the optical probe comprises one or more focusing units that simultaneously adjust a depth and a position of a focal point of the excitation light beam; (b) detecting at least a subset of the signals; and (c) using one or more computer processors programmed to process the at least the subset of the signals detected in (b) to generate the depth profile of the tissue.

In some embodiments, the excitation light beam is a pulsed light beam. In some embodiments, the excitation light beam is a single beam of light. In some embodiments, the single beam of light is a pulsed beam of light. In some embodiments, the excitation light beam comprises multiple beams of light. In some embodiments, the method further comprises (b) comprising simultaneously detecting a plurality of subsets of the signals. In some embodiments, the method further comprises processing the plurality of subsets of the signals to generate a plurality of depth profiles, wherein the plurality of depth profiles is indicative of a probe position at a time of detecting the signals. In some embodiments, the plurality of depth profiles corresponds to a same scanning path. In some embodiments, the scanning path comprises a slanted scanning path. In some embodiments the method further comprises assigning a least one distinct color for each of the plurality of depth profiles. In some embodiments, the method further comprises combining at least a subset of data from the plurality of depth profiles to form a composite depth profile. In some embodiments, the method further comprises displaying, on a display screen, a composite image derived from the composite depth profile. In some embodiments, the composite image is a polychromatic image. In some embodiments, color components of the polychromatic images correspond to multiple depth profiles using subsets of signals that are synchronized in time and location. In some embodiments, each of the plurality of layers comprise data that identifies different characteristics than those of other layers. In some embodiments, the depth profiles comprises a plurality of sub-set depth profiles, wherein the plurality of sub-set depth profiles comprise optical data from processed generated signals. In some embodiments, the plurality of depth profiles comprises a first depth profile and a second depth profile.

In some embodiments, the first depth profile comprises data processed from a signal that is different from data generated from a signal comprised in the second depth profile. In some embodiments, wherein the first depth and the second depth profile comprise one or more processed signals independently selected from the group consisting of a second harmonic generation (SHG) signal, a multi photon fluorescence signal, and a reflectance confocal microscopy (RCM) signal. In some embodiments, the plurality of depth profile comprises a third depth profile comprising data processed from a signal selected from the group consisting of a SHG signal, a multi photon fluorescence signal, and an RCM signal. In some embodiments, the depth profile comprises individual components, images, or depth profiles created from the plurality of subsets of the signals. In some embodiments, the depth profile comprises a plurality of layers created from a plurality of subsets of images collected from a same location and time. In some embodiments, the method further comprises generating a plurality of depth profiles. In some embodiments, each of the plurality of depth profiles corresponds to a different probe position. In some embodiments, the plurality of depth profiles correspond to different scan patterns at the time of detecting the signals. In some embodiments, the different scan patterns correspond to a same time and probe position. In some embodiments, at least one scanning pattern of the different scan patterns comprises a slanted scanning pattern. In some embodiments, the slanted scanning pattern forms a slanted plane.

In some embodiments, the tissue comprises in vivo tissue. In some embodiments, (c) comprises generating an in vivo depth profile. In some embodiments, the depth profile is an annotated depth profile. In some embodiments, the annotation comprises at least one annotation selected from the group consisting of words and markings. In some embodiments, the signals comprise at least one signal selected from the group consisting of an SHG signal, a multi photon fluorescence signal, and an RCM signal. In some embodiments, the multi photon fluorescence signal comprises a plurality of multi photon fluorescence signals. In some embodiments, the signals comprise at least two signals selected from the group consisting of an SHG signal, a multi photon fluorescence signal, and an RCM signal. In some embodiments, the signals comprise an SHG signal, a multi photon fluorescence signal, and an RCM signal. In some embodiments, the signals further comprise at least one signal selected from the group consisting of third harmonic generation signals, coherent anti-stokes Raman scattering signals, stimulated Raman scattering signals, and fluorescence lifetime imaging signals.

In some embodiments, the signals are generated at a same time and location within the tissue. In some embodiments, the method further comprises prior to (a), contacting the tissue of the subject with the optical probe. In some embodiments, the method further comprises adjusting the depth and the position of the focal point of the excitation light beam along a scanning path. In some embodiments, the scanning path is a slanted scanning path. In some embodiments, the slanted scanning path forms a slanted plane positioned along a direction that is angled with respect to an optical axis of the optical probe. In some embodiments, an angle between the slanted plane and the optical axis is greater than 0 degrees and less than 90 degrees. In some embodiments, (a)-(c) are performed in an absence of administering a contrast enhancing agent to the subject. In some embodiments, the excitation light beam comprises unpolarized light. In some embodiments, the excitation light beam comprises polarized light. In some embodiments, the detecting is performed in a presence of ambient light. In some embodiments, (a) is performed without penetrating the tissue of the subject. In some embodiments, the method further comprises using the one or more computer processors to identify a characteristic of the tissue using the depth profile.

In some embodiments, the method further comprises using the one or more computer processors to identify a disease in the tissue. In some embodiments, the disease is identified with an accuracy of at least about 80%. In some embodiments, the disease is identified with an accuracy of at least about 90%. In some embodiments, the disease is a cancer. In some embodiments, the tissue is a skin of the subject, and wherein the cancer is skin cancer. In some embodiments, the depth profile has a resolution of at least about 0.8 micrometers. In some embodiments, the depth profile has a resolution of at least about 4 micrometers. In some embodiments, the depth profile has a resolution of at least about 10 micrometers. In some embodiments, the method further comprises measuring a power of the excitation light beam. In some embodiments, the method further comprises monitoring the power of the excitation light beam in real-time. In some embodiments, the method further comprises using the one or more computer processors to normalize for the power, thereby generating a normalized depth profile. In some embodiments, the method further comprises displaying a projected cross section image of the tissue generated at least in part from the depth profile. In some embodiments, the method further comprises displaying a composite of a plurality of layers of images. In some embodiments, each of the plurality of layers is generated by a corresponding depth profile of a plurality of depth profiles.

In another aspect, the present disclosure provides a system for generating a depth profile of a tissue of a subject, comprising: an optical probe that is configured to transmit an excitation light beam from a light source to a surface of the tissue, which the excitation light beam, upon contacting the tissue, yield signals indicative of an intrinsic property of the tissue, wherein the optical probe comprises one or more focusing units that are configured to simultaneously adjust a depth and a position of a focal point of the excitation light beam; one or more sensors configured to detect at least a subset of the signals; and one or more computer processors operatively coupled to the one or more sensors, wherein the one or more computer processors are individually or collectively programmed to process the at least the subset of the signals detected by the one or more sensors to generate a depth profile of the tissue.

In some embodiments, the excitation light beam is a pulsed light beam. In some embodiments, the pulsed light beam is a single beam of light. In some embodiments, the one or more focusing units comprise a z-axis scanner and a micro-electro-mechanical-system (MEMS) mirror. In some embodiments, the z-axis scanner comprises one or more lenses. In some embodiments, at least one of the one or more lenses is an afocal lens. In some embodiments, the z-axis scanner comprises an actuator. In some embodiments, the actuator comprises a voice coil. In some embodiments, the z-axis scanner and the MEMS mirror are separately actuated by two or more actuators controlled by the one or more computer processors. In some embodiments, the one or more computer processors are programmed or otherwise configured to synchronize movement of the z-axis scanner and the MEMS mirror. In some embodiments, the synchronized movement of the z-axis scanner and the MEMS mirror provides synchronized movement of one or more focal points at a slant angle.

In some embodiments, the signals comprises at least one signal selected from the group consisting of a second harmonic generation (SHG) signal, a multi photon fluorescence signal, and a reflectance confocal microscopy (RCM) signal. In some embodiments, the multi photon fluorescence signal comprises a plurality of multi photon fluorescence signals. In some embodiments, the signals comprise at least two signals selected from the group consisting of a SHG signal, a multi photon fluorescence signal, and an RCM signal. In some embodiments, the signals comprise a SHG signal, a multi photon fluorescence signal, and an RCM signal. In some embodiments, the tissue is epithelial tissue, and wherein the depth profile facilitates identification of a disease in the epithelial tissue of the subject. In some embodiments, the depth and the position of the focal point of the excitation light beam are adjusted along a scanning path. In some embodiments, the scanning path is a slanted scanning path. In some embodiments, the slanted scanning path is a slanted plane positioned along a direction that is angled with respect to an optical axis of the optical probe. In some embodiments, an angle between the slanted plane and the optical axis is between 0 degrees to 90 degrees.

In some embodiments, the light source comprises an ultra-fast pulse laser with a pulse duration less than about 200 femtoseconds. In some embodiments, during use, the optical probe is in contact with the surface of the tissue. In some embodiments, the system further comprises a sensor that detects a displacement between the optical probe and the surface of the tissue. In some embodiments, the optical probe is configured to receive at least one of the subset of the signals, wherein the at least one of the subset of the signals comprises at least one RCM signal. In some embodiments, the optical probe comprises a selective optic configured to send the at least one of the subset of the signals into a fiber optic element. In some embodiments, the optical probe comprises an alignment arrangement configured to focus and align the at least one of the subset of signals into the fiber optic element. In some embodiments, the alignment arrangement comprises a focusing lens and an adjustable refractive element between the focusing lens and the fiber optic element. In some embodiments, the focusing lens and the fiber optic element are in a fixed position with respect to the adjustable refractive element. In some embodiments, the adjustable refractive element is angularly moveable. In some embodiments, the adjustable refractive element further comprises at least one adjustment element.

In some embodiments, the system further comprises a moveable mirror, wherein the focusing lens is positioned between the moveable mirror and the refractive element. In some embodiments, the system further comprises a polarizing selective optic positioned between a beam splitter and the focusing lens. In some embodiments, the selective optic comprises an optical filter selected from the group consisting of a beam splitter, a polarizing beam splitter, a notch filter, a dichroic mirror, a long pass filter, a short pass filter, a bandpass filter, and a response flattening filter. In some embodiments, the at least the subset of the signals comprises polarized light. In some embodiments, the optical probe comprises one or more polarization selective optics which select a polarization of the polarized light. In some embodiments, the at least the subset of the signals comprises an RCM signal from a polarization of the polarized light. In some embodiments, the at least the subset of signals comprise unpolarized light. In some embodiments, the optical probe is configured to reject out of focus light.

In some embodiments, the one or more sensors comprises one or more photosensors. In some embodiments, the system further comprises a marking tool for outlining a boundary that is indicative of a location of the disease in the tissue of the subject. In some embodiments, the system is a portable system. In some embodiments, the portable system is less than or equal to 50 pounds. In some embodiments, the optical probe comprises a housing configured to interface with a hand of a user. In some embodiments, the housing further comprises a sensor within the housing. In some embodiments, the sensor is configured to locate the optical probe in space. In some embodiments, the sensor is an image sensor, wherein the image sensor is configured to locate the optical probe in space by tracking one or more features. In some embodiments, the one or more features comprise features of the tissue of the subject. In some embodiments, the one or more features comprise features of a space wherein the optical probe is used. In some embodiments, the image sensor is a video camera. In some embodiments, the system further comprises an image sensor adjacent to the housing. In some embodiments, the image sensor locates the optical probe in space. In some embodiments, the one or more features comprise features of the tissue of the subject.

In some embodiments, the one or more features comprise features of a space wherein the optical probe is used.

In some embodiments, the system further comprises a power sensor optically coupled to the excitation light beam. In some embodiments, the depth profile has a resolution of at least about 0.8 micrometers. In some embodiments, the depth profile has a resolution of at least about 4 micrometers. In some embodiments, the depth profile has a resolution of at least about 10 micrometers. In some embodiments, the depth profile is an in vivo depth profile. In some embodiments, the depth profile is an annotated depth profile. In some embodiments, the depth profile comprises a plurality of depth profiles. In some embodiments, the one or more computer processors are programmed to display a projected cross section image of tissue.

In another aspect, the present disclosure provides a method for analyzing tissue of a body of a subject, comprising: directing light to the tissue of the body of the subject; receiving a plurality of signals from the tissue of the body of the subject in response to the light directed thereto in (a), wherein at least a subset of the plurality of signals are from within the tissue; inputting data corresponding to the plurality of signals to a trained machine learning algorithm that processes the data to generate a classification of tissue of the body of the subject; and outputting the classification on a user interface of an electronic device of a user.

In some embodiments, the data comprises at least one depth profile. In some embodiments, the at least one depth profile comprises one or more layers. In some embodiments, the one or more layers are synchronized in time and location. In some embodiments, the depth profile comprises one or more depth profiles synchronized in time and location. In some embodiments, the plurality of signals are generated substantially simultaneously by the light. In some embodiments, the depth profile comprises an annotated depth profile. In some embodiments, the depth profile comprises an in-vivo depth profile. In some embodiments, the trained machine learning algorithm comprises an input layer, to which the data is presented; one or more internal layers; and an output layer. In some embodiments, the input layer includes a plurality of the depth profiles using data processed from one or more signals that are synchronized in time and location. In some embodiments, the depth profiles are generated using the optical probe. In some embodiments, the depth profiles comprise individual components, images, or depth profiles generated from a plurality of the subsets of signals. In some embodiments, the depth profile comprises a plurality of layers generated from a plurality of subsets of images collected from the same location and time. In some embodiments, each of a plurality of layers comprises data that identifies different characteristics than those of the other layers. In some embodiments, the depth profiles comprise a plurality of sub-set depth profiles.

In some embodiments, the classification identifies features of the tissue in the subject pertaining to a property of the tissue selected from the group consisting of health, function, treatment, and appearance. In some embodiments, the classification identifies the subject as having a disease. In some embodiments, the disease is a cancer. In some embodiments, the tissue is a skin of the subject, and wherein the cancer is skin cancer. In some embodiments, the plurality of signals comprise at least one signal selected from the group consisting of an SHG signal, a multi photon fluorescence signal, and an RCM signal. In some embodiments, the plurality of signals comprise at least two signals selected from the group consisting of a SHG signal, a multi photon fluorescence signal, and an RCM signal. In some embodiments, the plurality of signals comprise a SHG signal, a multi photon fluorescence signal, and an RCM signal. In some embodiments, the multi photon fluorescence signal comprises one or more multi photon fluorescence signals. In some embodiments, (c) comprises identifying one or more features corresponding to the plurality of signals using the trained machine learning algorithm. In some embodiments, the trained machine learning algorithm comprises a neural network. In some embodiments, the neural network comprises an input layer, to which data is presented. In some embodiments, the neural network further comprises one or more internal layers and an output layer.

In some embodiments, the input layer comprises a plurality of depth profiles generated using at least a subset of the plurality of signals synchronized in time and location. In some embodiments, at least one of the plurality of depth profiles is generated using the optical probe, wherein the optical probe comprises one or more focusing units, wherein the one or more focusing units comprise a z-axis scanner and a MEMS mirror. In some embodiments, at least one of the plurality of depth profiles comprises individual components from a plurality of subsets of the plurality of signals. In some embodiments, at least one depth profile of the plurality of depth profiles comprises a plurality of layers generated from optical data collected from the same location and time. In some embodiments, each of the plurality of layers comprises data that identifies a different characteristic than those of another layers. In some embodiments, the depth profile comprises a plurality of sub-set depth profiles. In some embodiments, the neural network comprises a convolutional neural network. In some embodiments, the data is controlled for an illumination power of the optical signal. In some embodiments, the method further comprises receiving medical data of the subject. In some embodiments, the medical data of the subject comprises at least one medical data selected from the group consisting of a physical condition, medical history, current and past occupations, age, sex, race, and nationally of the subject.

In some embodiments, the physical condition comprises vital signs of the subject. In some embodiments, the medical data comprises at least one medical data selected from the group consisting of structured data, time-series data, unstructured data, and relational data. In some embodiments, the medical data is uploaded to a cloud-based database. In some embodiments, the data comprises at least one medical data selected from the group consisting of structured data, time-series data, unstructured data, and relational data. In some embodiments, the data is uploaded to a cloud-based database. In some embodiments, the data is kept on a local device. In some embodiments, the data comprises depth profiles taken of overlapping regions of the tissue.

In another aspect, the present disclosure provides a system for analyzing tissue of a body of a subject, comprising: an optical probe that is configured to (i) direct an excitation light beam to the tissue of the body of the subject, and (ii) receive a plurality of signals from the tissue of the body of the subject in response to the light excitation beam directed thereto in (i), wherein at least a subset of the plurality of signals are from within the tissue; and one or more computer processors operatively coupled to the optical probe, wherein the one or more computer processors are individually or collectively programmed to (i) receive data corresponding to the plurality of signals, (ii) input the data to a trained machine learning algorithm that processes the data to generate a classification of the tissue of the body of the subject, and (iii) output the classification on a user interface of an electronic device of a user.

In some embodiments, the excitation light beam is a pulsed light beam. In some embodiments, the pulsed light beam is a single beam of light. In some embodiments, the data comprises at least one depth profile. In some embodiments, the at least one depth profile comprises one or more layers. In some embodiments, the one or more layers are synchronized in time and location. In some embodiments, the depth profile comprises one or more depth profiles synchronized in time and location. In some embodiments, the depth profile comprises an annotated depth profile. In some embodiments, the depth profile comprises an in-vivo depth profile. In some embodiments, the trained machine learning algorithm comprises an input layer, to which the data is presented; one or more internal layers; and an output layer. In some embodiments, the input layer includes a plurality of the depth profiles using data processed from one or more signals that are synchronized in time and location. In some embodiments, the depth profiles are generated using the optical probe.

In some embodiments, the optical probe comprises one or more focusing units. In some embodiments, the one or more focusing units comprise a z-axis scanner and a micro-electro-mechanical-system (MEMS) mirror. In some embodiments, the z-axis scanner comprises one or more lenses. In some embodiments, at least one of the one or more lenses is an afocal lens. In some embodiments, the z-axis scanner comprises an actuator. In some embodiments, the actuator comprises a voice coil. In some embodiments, the z-axis scanner and the MEMS mirror are separately actuated by two or more actuators controlled by the one or more computer processors. In some embodiments, the one or more computer processors are programmed or otherwise configured to synchronize movement of the z-axis scanner and the MEMS mirror. In some embodiments, the synchronized movement of the z-axis scanner and the MEMS mirror provides synchronized movement of focal points at a slant angle.

In some embodiments, the optical probe and the one or more computer processors are in a same device. In some embodiments, the device is a mobile device. In some embodiments, the optical probe is part of a device, and wherein the one or more computer processors are separate from the device. In some embodiments, the one or more computer processors are part of a computer server. In some embodiments, the one or more computer processors are part of a distributed computing infrastructure. In some embodiments, the one or more computer processors are programmed to receive medical data of the subject. In some embodiments, the medical data of the subject comprises at least one medical data selected from the group consisting of a physical condition, medical history, current and past occupations, age, sex, race, and nationally of the subject. In some embodiments, the physical condition comprises vital signs of the subject. In some embodiments, the medical data comprises at least one medical data selected from the group consisting of structured data, time-series data, unstructured data, and relational data. In some embodiments, the data comprises at least one medical data selected from the group consisting of structured data, time-series data, unstructured data, and relational data.

In another aspect, the present disclosure provides a method for generating a trained algorithm for identifying a characteristic in a tissue of a subject, comprising: (a) collecting signals from training tissues of subjects that have been previously or subsequently identified as having the characteristic; (b) processing the signals to generate data corresponding to depth profiles of the training tissues of the subjects; and (c) using the data from (b) to train a machine learning algorithm to yield a trained algorithm in computer memory for identifying the characteristic in the tissue of the subject wherein the tissue is independent of the training tissues.

In some embodiments, the characteristic is a disease. In some embodiments, the characteristic is a characteristic corresponding to a property of the tissue selected from the group consisting of a health, function, treatment, and appearance of the tissue. In some embodiments, the data comprises data having a consistent labeling and consistent properties. In some embodiments, the consistent properties comprise properties selected from the group consisting of illumination intensity, contrast, color, size, and quality. In some embodiments, the data is normalized with respect to an illumination intensity. In some embodiments, the depth profiles correspond to different positions of an optical probe on the tissue. In some embodiments, (a) comprises generating one or more depth profiles using at least a subset of the signals. In some embodiments, the at least the subset of the signals is synchronized in time and location. In some embodiments, the data correspond to the one or more depth profiles. In some embodiments, at least one of the one or more depth profiles comprises a plurality of layers.

In some embodiments, the plurality of layers is generated from a plurality of subsets of images collected at the same time and location. In some embodiments, each of the plurality of layers comprises data that identifies a different characteristics than that of another layer. In some embodiments, each of the one or more depth profiles comprises a plurality of sub-set depth profiles. In some embodiments, the method further comprises training the machine learning algorithm using each of the plurality of sub-set depth profiles individually. In some embodiments, the method further comprises generating a composite depth profile using the plurality of sub-set depth profiles. In some embodiments, the method further comprises using the composite depth profile to train the machine learning algorithm. In some embodiments, the method further comprises generating the one or more depth profiles using a first set of signals collected from a first region of a training tissue and a second set of signals from a second region of the training tissue. In some embodiments, the first region of the training tissue is different from the second region of the training tissue. In some embodiments, the first region of the training tissue has the disease. In some embodiments, the signals comprise two or more signals. In some embodiments, the two or more signals are selected from the group consisting of a second harmonic generation (SHG) signal, a multi photon fluorescence signal, and a reflectance confocal microscopy (RCM) signal. In some embodiments, the two or more signals are substantially simultaneous signals of a single region of the tissue. In some embodiments, the two or more signals are processed and combined to generate a composite image.

In another aspect, the present disclosure provides a system for generating a trained algorithm for identifying a characteristic in a tissue of a subject, comprising: a database comprising data corresponding to depth profiles of training tissues of subjects that have been previously or subsequently identified as having the characteristic, which depth profiles are generated from processing signals collected from the training tissues; and one or more computer processors operatively coupled to the database, wherein the one or more computer processors are individually or collectively programmed to (i) retrieve the data from the database and (ii) use the data to train a machine learning algorithm to yield a trained algorithm in computer memory for identifying the characteristic in the tissue of the subject wherein the tissue is independent of the training tissues.

In some embodiments, the characteristic is a disease. In some embodiments, the characteristic corresponds to a characteristic of the tissue selected from the group consisting of a health, function, treatment, and appearance. In some embodiments, the one or more computer processors are programmed to receive optical data of one or more depth profiles. In some embodiments, the depth profiles are generated using signals collected from the training tissues. In some embodiments, the signals are synchronized in time and location. In some embodiments, the depth profiles comprise a plurality of layers. In some embodiments, the plurality of layers is generated from a plurality of subsets of images collected at the same time and location. In some embodiments, each of the plurality of layers comprises data that identifies a different characteristic than that of another layer. In some embodiments, the one or more computer processors are programmed to receive medical data of the subject. In some embodiments, the medical data comprises at least one medical data selected from the group consisting of structured data, time-series data, unstructured data, and relational data. In some embodiments, the data comprises structured data, time-series data, unstructured data, relational data, or any combination thereof.

In some embodiments, the depth profiles have one or more annotations. In some embodiments, the depth profiles are in vivo depth profiles. In some embodiments the depth profiles are depth profiles of one or more overlapping regions of the tissue. In some embodiments, the characteristic is a disease. In some embodiments, the characteristic is a characteristic corresponding to a property of the tissue selected from the group consisting of a health, function, treatment, and appearance of the tissue. In some embodiments, the data comprises data having a consistent labeling and consistent properties. In some embodiments, the consistent properties comprise properties selected from the group consisting of illumination intensity, contrast, color, size, and quality. In some embodiments, the data is normalized with respect to an illumination intensity. In some embodiments, the depth profiles correspond to different positions of an optical probe on the tissue.

In another aspect, the present disclosure provides a method for aligning a light beam, comprising: (a) providing (i) a light beam in optical communication with a lens, wherein the lens is in optical communication with a refractive element, (ii) an optical fiber, and (iii) a detector in optical communication with the optical fiber, wherein the refractive element is positioned between the lens and the optical fiber; and (b) adjusting the refractive element to align the optical path with the optical fiber, wherein the optical path is thereby aligned with the optical fiber.

In some embodiments, a point spread function of the beamlet after interacting with the refractive element is sufficiently small to enable a resolution of the detector to be less than 1 micrometer. In some embodiments, the adjusting the position comprises applying a rotation to the refractive element. In some embodiments, the rotation is at most a 180° rotation. In some embodiments, the rotation is a rotation in at most two dimensions. In some embodiments, the rotation is a rotation in one dimension. In some embodiments, the method further comprises providing an adjustable mirror wherein the lens is fixed between the adjustable mirror and the adjustable refractive element and adjusting the adjustable mirror aligns the optical path prior to using the adjustable refractive element. In some embodiments, the providing the light beam comprises providing a generated light signal from an interaction with a tissue of a subject. In some embodiments, the tissue is an in vivo skin tissue.

In another aspect, the present disclosure provides a system for aligning a light beam, comprising: a light source that is configured to provide a light beam; a focusing lens in optical communication with the light source; an adjustable refractive element in optical communication with the lens; an optical fiber; and a detector in optical communication with the optical fiber, wherein the adjustable refractive element is positioned between the focusing lens and the optical fiber and is moveable to align an optical path between the focusing lens and the optical fiber.

In some embodiments, the focusing lens and the optical fiber are fixed with respect to the adjustable refractive element. In some embodiments, the adjustable refractive element is angularly moveable. In some embodiments, the system further comprises adjustment elements coupled to the adjustable refractive element, wherein the adjustment elements are configured to adjust a position of the adjustable refractive element. In some embodiments, the adjustment elements angularly move the adjustable refractive element. In some embodiments, the system further comprises a controller operatively coupled to the refractive element, wherein the controller is programmed to direct adjustment of the refractive element to align the optical path with the optical fiber. In some embodiments, the adjustment is performed without an input of a user. In some embodiments, the adjustment is performed by a user. In some embodiments, the system further comprises a beam splitter configured to direct light along the optical path towards the optical fiber. In some embodiments, the system further comprises a moveable mirror positioned between the beam splitter and the focusing lens. In some embodiments, the system further comprises a polarization selective optic positioned on the optical path. In some embodiments, the polarization selective optic is positioned between the beam splitter and the focusing lens. In some embodiments, the refractive element is a flat window.

In some embodiments, the refractive element is a glass refractive element. In some embodiments, a point spread function of a beamlet of light after interacting with the refractive element is sufficiently small to enable a resolution of the detector to be less than 1 micrometer. In some embodiments, the refractive element has a footprint of less than 1,000 $mm^2$. In some embodiments, the refractive element is configured to adjust a beamlet of light at most about 10 degrees. In some embodiments, the refractive element has a has a property that permits alignment of a beam of light exiting the lens to a fiber optic. In some embodiments, the diameter is less than about 20 microns. In some embodiments, the diameter is less than about 10 microns. In some embodiments, the fiber optic has a diameter of less than about 5 microns. In some embodiments, the property is at least one property selected from the group consisting of a refractive index, a thickness, and a range of motion. In some embodiments, an aberration introduced by the refractive element is less than 20% of a diffraction limit of the focusing lens. In some embodiments, the aberration is less than 10% of the diffraction limit. In some embodiments, the aberration is less than 5% of the diffraction limit. In some embodiments, the aberration is less than 2% of the diffraction limit. In some embodiments, the aberration is less than 1% of the diffraction limit.

In another aspect, the present disclosure provides a method for aligning a light beam, comprising: (a) providing (i) a light beam in optical communication with a beam splitter, wherein the beam splitter is in optical communication with a lens, wherein the lens is in optical communication with a refractive element, (ii) an optical fiber, and (iii) a detector in optical communication with the optical fiber, wherein an optical path from the refractive element is misaligned with respect to the optical fiber; (b) adjusting the refractive element to align the optical path with the optical fiber; and (c) directing the light beam to the beam splitter that splits the light beam into a beamlet, wherein the beamlet is directed through the lens to the refractive element that directs the beamlet along the optical path to the optical fiber, such that the detector detects the beamlet.

In another aspect, the present disclosure provides a system for aligning a light beam, comprising: a light source that is configured to provide a light beam; a beam splitter in optical communication with the light source; a lens in optical communication with the beam splitter; a refractive element in optical communication with the lens; an optical fiber; and a detector in optical communication with the optical fiber, wherein an optical path from the refractive element is misaligned with respect to the optical fiber, wherein the refractive element is adjustable to align the optical path with the optical fiber, such that, when the optical path is aligned with the optical fiber, the light beam is directed from the light source to the beam splitter that splits the light beam into a beamlet, wherein the beamlet is directed through the lens to the refractive element that directs the beamlet along the optical path to the optical fiber, such that the detector detects the beamlet.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 7A-7D show examples of images formed from scanned in-vivo depth profiles.

DETAILED DESCRIPTION

Figure 1:
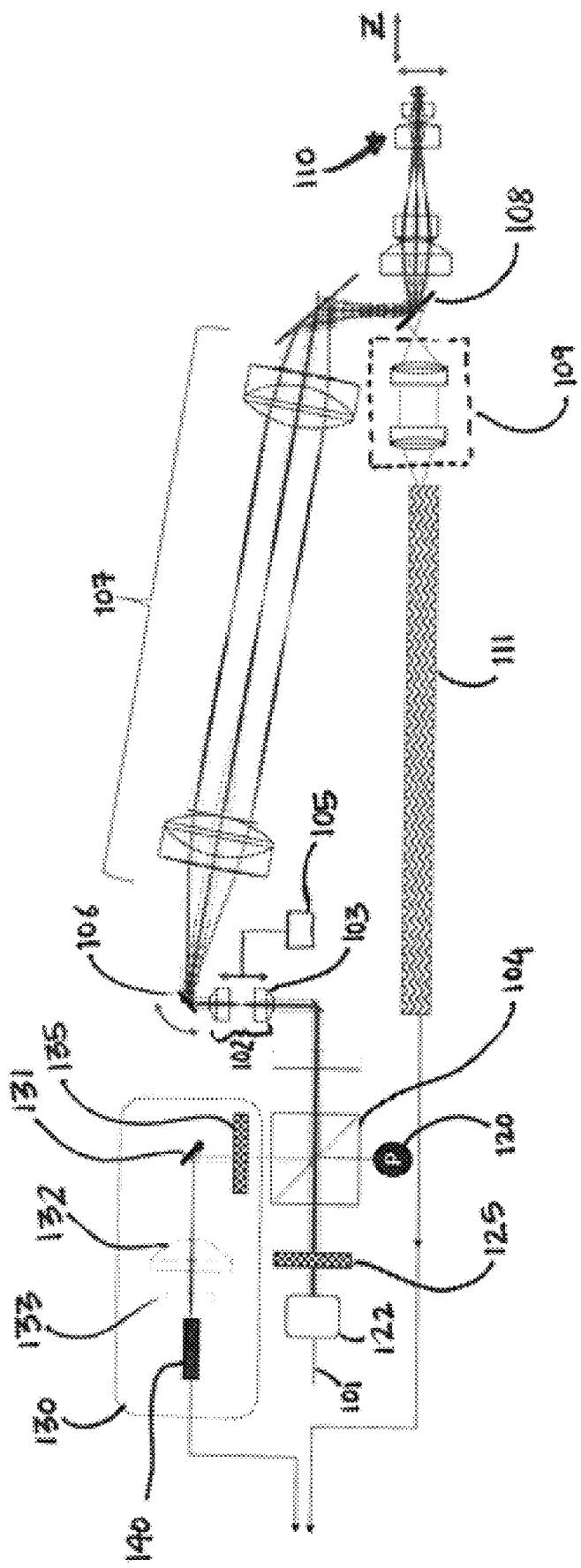
FIG. 1 shows examples of optical elements comprising focusing units for scanning a tissue.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "subject," as used herein, generally refers to an animal, such as a mammal. A subject may be a human or non-human mammal. A subject may be afflicted with a disease or suspected of being afflicted with or having a disease. The subject may not be suspected of being afflicted with or having the disease. The subject may be symptomatic. Alternatively, the subject may be asymptomatic. In some cases, the subject may be treated to alleviate the symptoms of the disease or cure the subject of the disease. A subject may be a patient undergoing treatment by a healthcare provider, such as a doctor.

The term "disease," as used herein, generally refers to an abnormal condition, or a disorder of a biological function or a biological structure such as an organ, that affects part or all of a subject. A disease may be caused by factors originally from an external source, such as infectious disease, or it may be caused by internal dysfunctions, such as autoimmune diseases. A disease can refer to any condition that causes pain, dysfunction, distress, social problems, and/or death to the subject afflicted. A disease may be an acute condition or a chronic condition. A disease may refer to an infectious disease, which may result from the presence of pathogenic microbial agents, including viruses, bacteria, fungi, protozoa, multicellular organisms, and aberrant proteins as prions. A disease may refer to a non-infectious disease, including but not limited to cancer and genetic diseases. In some cases, a disease can be cured. In some cases, a disease cannot be cured. In some cases, the disease is epithelial cancer. An epithelial cancer is a skin cancer including, but not limited to, non-melanoma skin cancers, such as basal cell carcinoma (BCC) and squamous cell carcinoma (SCC), and melanoma skin cancers.

The terms "epithelial tissue" and "epithelium," as used herein, generally refer to the tissues that line the cavities and surface of blood vessels and organs throughout the body. Epithelial tissue comprises epithelial cells of which there are generally three shapes: squamous, columnar, and cuboidal. Epithelial cells can be arranged in a single layer of cells as simple epithelium comprising either squamous, columnar, or cuboidal cells, or in layers of two or more cells deep as stratified (layered), comprising either squamous, columnar, and/or cuboidal.

The term "cancer," as used herein, generally refers to a proliferative disorder caused or characterized by a proliferation of cells which may have lost susceptibility to normal growth control. Cancers of the same tissue type usually originate in the same tissue and may be divided into different subtypes based on their biological characteristics. Non-limiting examples of categories of cancer are carcinoma (epithelial cell derived), sarcoma (connective tissue or mesodermal derived), leukemia (blood-forming tissue derived) and lymphoma (lymph tissue derived). Cancer may involve any organ or tissue of the body. Examples of cancer include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include the pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. In some cases, a cancer can be multicentric. In some cases, a cancer can be a cancer of unknown primary (CUP).

The term "lesion," as used herein, generally refers to an area(s) of disease and/or suspected disease, wound, incision, or surgical margin. Wounds may include, but are not limited to, scrapes, abrasions, cuts, tears, breaks, punctures, gashes, slices, and/or any injury resulting in bleeding and/or skin trauma sufficient for foreign organisms to penetrate. Incisions may include those made by a medical professional, such as but not limited to, physicians, nurses, mid-wives, and/or nurse practitioners, and dental professionals during treatment such as a surgical procedure.

The term "light," as used herein, generally refers to electromagnetic radiation. Light may be in a range of wavelengths from infrared (e.g., about 700 nm to about 1 mm) through the ultraviolet (e.g., about 10 nm to about 380 nm). Light may be visible light. Alternatively, light may be non-visible light. Light may include wavelengths of light in the visible and non-visible wavelengths of the electromagnetic spectrum.

The term "ambient light," as used herein, generally refers to the light surrounding an environment or subject, such as the light at a location in which devices, methods and systems of the present disclosure are used, such as a point of care location (e.g., a subject's home or office, a medical examination room, or operating room).

The term "optical axis" as used herein, generally refers to a line along which there may be some degree of rotational symmetry in an optical system such as a camera lens or microscope. The optical axis may be a line passing through the center of curvature of a lens or spherical mirror and parallel to the axis of symmetry. The optical axis herein is may also be referred to as the Z axis. For a system of simple lenses and mirrors, the optical axis may pass through the center of curvature of each surface and coincide with the axis of rotational symmetry. The optical axis may be coincident with the system's mechanical axis, as in the case of off-axis optical systems. For an optical fiber, the optical axis (also called as fiber axis) may be along the center of the fiber core.

The term "position," as used herein, generally refers to a location on a plane perpendicular to the optical axis as opposed to a "depth" which is parallel to the optical axis. For example, a position of a focal point can be a location of the focal point in the x-y plane. Whereas a "depth" position can be a location along a z axis (optical axis). A position of a focal point can be varied throughout the x-y plane. A focal point can also be varied simultaneously along the z axis.

The term "focal point" or "focal spot" as used herein generally refers to a point of light on an axis of a lens or mirror of an optical element to which parallel rays of light converge. The focal point or focal spot can be in a tissue sample to be imaged, from which a return signal is generated that can be processed to create depth profiles.

The term "focal plane" as used herein, generally refers a plane formed by focal points directed along a scan path. The focal plane can be where the focal point moves in an X and/or Y direction, along with a movement in a Z direction wherein the Z axis is generally an optical axis. A scan path may also be considered a focal path that comprises at least two focal points that define a path that is non-parallel to the optical axis. For example, a focal path may comprise a plurality of focal points shaped as a spiral. A focal path as used herein may or may not be a plane and may be a plane when projected on an X-Z or Y-Z plane. The focal plane may be a slanted plane. The slanted plane may be a plane that is oriented at an angle with respect to an optical axis of an optical element (e.g., a lens or a mirror). The angle may be between about 0° and about 90°. The slanted plane may be a plane that has non-zero Z axis components.

The term "depth profile," as used herein, generally refers to information or optical data derived from the generated signals that result from scanning a tissue sample. The scanning a tissue sample can be with imaging focal points extending in a parallel direction to an optical axis or z axis, and with varying positions on an x-y axis. The tissue sample can be, for example, in vivo skin tissue where the depth profile can extend across layers of the skin such as the dermis, epidermis, and subcutaneous layers. A depth profile of a tissue sample can include data that when projected on an X-Z or Y-Z plane creates a vertical planar profile that can translate into a projected vertical cross section image. The vertical cross section image of the tissue sample derived from the depth profile can be vertical or approximately vertical. In some cases, a depth profile provides varied vertical focal point coordinates while the horizontal focal point coordinates may or may not vary. A depth profile may be in the form of at least one plane at an angle to an optical plane (on an optical axis). For example, a depth profile may be parallel to an optical plane or may be at an angle less 90 degrees and greater than 0 degrees with respect to an optical plane. A depth profile may be generated using an optical probe that is contacting a tissue at an angle. For example, a depth profile may not be perpendicular to the optical axis, but rather offset by the same degree as the angle the optical probe is contacting the tissue. A depth profile can provide information at various depths of the sample, for example at various depths of a skin tissue. A depth profile can be provided in real-time. A depth profile may or may not correspond to a planar slice of tissue. A depth profile may correspond to a slice of tissue on a slanted plane. A depth profile may correspond to a tissue region that is not precisely a planar slice (e.g., the slice may have components in all three dimensions). A depth profile can be a virtual slice of tissue or a virtual cross section. A depth profile can be optical data scanned from in-vivo tissue. The data used to create a projected cross section image may be derived from a plurality of focal points distributed along a general shape or pattern. The plurality of distributed points can be in the form of a scanned slanted plane, a plurality of scanned slanted planes, or non-plane scan patterns or shapes (e.g., a spiral pattern, a wave pattern, or other predetermined or random or pseudorandom patterns of focal points.) The location of the focal points used to create a depth profile may be changed or changeable to track an object or region of interest within the tissue, that is detected or identified during scanning or related data processing. A depth profile may be formed from one or more distinct return signals or signals that correspond to anatomical features or characteristics from which distinct layers of a depth profile can be created. The generated signals used to form a depth profile can be generated from an excitation light beam. The generated signals used to form a depth profile can be synchronized in time and location. A depth profile may comprise a plurality of depth profiles where each depth profile corresponds to a particular signal or subset of signals that correspond to anatomical feature(s) or characteristics. The depth profiles can form a composite depth profile generated using signals synchronized in time and location. Depth profiles herein can be in vivo depth profiles wherein the optical data is taken of in vivo tissue. A depth profile can be a composite of a plurality of depth profiles or layers of optical data generated from different generated signals that are synchronized in time and location. A depth profile can be a depth profile generated from a subset of generated signals that are synchronized in time and location with other subsets of generated signals. A depth profile can include one or more layers of optical data, where each of the layer corresponds to a different subset of signals. A depth profile or depth profile optical data can also include data from processing the depth profile, the optical probe, other sensors, or information identified and corresponding to the time of the depth profile. Additionally, other data corresponding to subject information such as, for example, medical data, physical conditions, or other data, can also be included with optical data of a depth profile. Depth profiles can be annotated depth profiles with annotations or markings.

The term "projected cross section image" as used herein generally refers to an image constructed from depth profile information projected onto the XZ or YZ plane to create an image plane. In this situation, there may be no distortion in depths of structures relative to the surface of the tissue. The projected cross section image may be defined by the portion of the tissue that is scanned. A projected cross section image can extend in a perpendicular direction relative to the surface of the skin tissue. The data used to create a projected cross section image may be derived from a scanned slanted plane or planes, and/or non-plane scan patterns, shapes (e.g., a spiral, a wave, etc.), or predetermined or random patterns of focal points.

The term "fluorescence," as used herein, generally refers to radiation that can be emitted as the result of the absorption of incident electromagnetic radiation of one or more wavelengths (e.g., a single wavelength or two different wavelengths). In some cases, fluorescence may result from emissions from exogenously provided tags or markers. In some cases, fluorescence may result as an inherent response of one or more endogenous molecules to excitation with electromagnetic radiation.

The term "autofluorescence," as used herein, generally refers to fluorescence from one or more endogenous molecules due to excitation with electromagnetic radiation.

The term "multi-photon excitation," as used herein, generally refers to excitation of a fluorophore by more than one photon, resulting in the emission of a fluorescence photon. In some cases, the emitted photon is at a higher energy than the excitatory photons. In some cases, a plurality of multi-photon excitations may be generated within a tissue. The plurality of multi-photon excitations may generate a plurality of multi-photon signals. For example, cell nuclei can undergo a two-photon excitation. As another example, cell walls can undergo a three-photon excitation. At least a subset of the plurality of signals may be different. The different signals may have different wavelengths which may be used for methods described herein. For example, the different signals (e.g., two-photon or three-photon signals) can be used to form a map which may be indicative of different elements of a tissue. In some cases, the map is used to train machine learning based diagnosis algorithms.

The terms "second harmonic generation" and "SHG," as used herein, generally refer to a nonlinear optical process in which photons interacting with a nonlinear material are effectively "combined" to form new photons with about twice the energy, and therefore about twice the frequency and about half (½) the wavelength of the initial photons.

The terms "third harmonic generation" and "THG," as used herein, generally refer to a nonlinear optical process in which photons interacting with a nonlinear material are effectively "combined" to form new photons with about three times the energy, and therefore about three times the frequency and about a third (⅓) the wavelength of the initial photons.

The term "reflectance confocal microscopy" or "RCM," as used herein, generally refers to a process of collecting and/or processing reflected light from a sample (e.g., a tissue or any components thereof). The process may be a non-invasive process where a light beam is directed to a sample and returned light from the focal point within the sample ("RCM signal") may be collected and/or analyzed. The process may be in vivo or ex vivo. RCM signals may trace a reverse direction of a light beam that generated them. RCM signals may be polarized or unpolarized. RCM signals may be combined with a pinhole, single mode fiber, multi-mode fiber, intersecting excitation and collection optical pathways, or other confocal arrangements that restrict the light collected to that portion arising from the focal point.

The term "polarized light," as used herein, generally refers to light with waves oscillating in one plane. Unpolarized light can generally refer to light with waves oscillating in more than one plane.

The term "excitation light beam," as used herein, generally refers to the focused light beam directed to tissue to create a generated signal. An excitation light beam can be a single beam of light. An excitation light beam can be a pulsed single beam of light. An excitation beam of light can be a plurality of light beams. The plurality of light beams can be synchronized in time and location as described herein. An excitation beam of light can be a pulsed beam or a continuous beam or a combination one or more pulsed and/or continuous beams that are delivered simultaneously to a focal point of tissue to be imaged. The excitation light beam can be selected depending upon the predetermined type of return signal or generated signal as described herein.

The term "generated signal" as used herein generally refers to a signal that is returned from the tissue resulting from direction of focused light, e.g. excitation light, to the tissue and including but not limited to reflected, absorbed, scattered, or refracted light. Generated signals may include, but are not limited to, endogenous signals arising from the tissue itself or signals from exogenously provided tags or markers. Generated signals may arise in either in vivo or ex vivo tissue. Generated signals may be characterized as either single-photon generated signals or multi-photon generated signals as determined by the number of excitation photons that contribute to a signal generation event. Single-photon generated signals may include but are not limited to reflectance confocal microscopy ("RCM") signals, single-photon fluorescence, and single-photon autofluorescence. Single-photon generated signals, such as RCM, can arise from either a continuous light source, or a pulsed light source, or a combination of light sources that can be either pulsed or continuous. Single-photon generated signals may overlap. Single-photon generated signals may be deconvoluted. Multi-photon generated signals may be generated by at least 2, 3, 4, 5, or more photons. Multi-photon generated signals may include but are not limited to second harmonic generation, two-photon autofluorescence, two-photon fluorescence, third harmonic generation, three-photon autofluorescence, three-photon fluorescence, multi-photon autofluorescence, multi-photon fluorescence, and coherent anti-stokes Raman spectroscopy. Multi-photon generated signals can arise from either a single pulsed light source, or a combination of pulsed light sources as in the case of coherent anti-stokes Raman spectroscopy. Multi-photon generated signals may overlap. Multi-photon generated signals may be deconvoluted. Other generated signals may include but are not limited to Optical Coherence Tomography (OCT), single or multi-photon fluorescence/autofluorescence lifetime imaging, polarized light microscopy signals, additional confocal microscopy signals, and ultrasonography signals. Single-photon and multi-photon generated signals can be combined with polarized light microscopy by selectively detecting the components of said generated signals that are either linearly polarized light, circularly polarized light, unpolarized light, or any combination thereof. Polarized light microscopy may further comprise blocking all or a portion of the generated signal possessing a polarization direction parallel or perpendicular to the polarization direction of the light used to generate the signals or any intermediate polarization direction. Generated signals as described herein may be combined with confocal techniques utilizing a pinhole, single mode fiber, multimode fiber, intersecting excitation and collection optical pathways, or other confocal arrangements that restrict the light detected from the generated signal to that portion of the generated signal arising from the focal point. For example, a pinhole can be placed in a Raman spectroscopy instrument to generate confocal Raman signals. Raman spectroscopy signals may generate different signals based at least in part on different vibrational states present within a sample or tissue. Optical coherence tomography signals may use light comprising a plurality of phases to image a tissue. Optical coherence tomography may be likened to optical ultrasonography. Ultrasonography may generate a signal based at least in part on the reflection of sonic waves off of features within a sample (e.g., a tissue).

The term "contrast enhancing agent," as used herein, generally refers to any agent such as but not limited to fluorophores, metal nanoparticles, nanoshell composites and semiconductor nanocrystals that can be applied to a sample to enhance the contrast of images of the sample obtained using optical imaging techniques. Fluorophores can be antibody targeted fluorophores, peptide targeted fluorophores, and fluorescent probes of metabolic activity. Metallic nanoparticles can comprise metals such as gold and silver that can scatter light. Nanoshell composites can include nanoparticles comprising a dielectric core and metallic shell. Semiconductor nanocrystals can include quantum dots, for example quantum dots containing cadmium selenide or cadmium sulfide. Other contrasting agents can be used herein as well, for example by applying acetic acid to tissue.

The term "in real-time" and "real-time," as used herein, generally refers to immediate, rapid, not requiring operator intervention, automatic, and/or programmed. Real-time may include, but is not limited to, measurements in femtoseconds, picoseconds, nanoseconds, milliseconds, seconds, as well as longer, and optionally shorter, time intervals.

The term "tissue" as used herein, generally refers to any tissue sample. A tissue may be a sample that is healthy, benign, or otherwise free of a disease. A tissue may be a sample removed from a subject, such as a tissue biopsy, a tissue resection, an aspirate (such as a fine needle aspirate), a tissue washing, a cytology specimen, a bodily fluid, or any combination thereof. A tissue may comprise neurons. A tissue may comprise brain tissue, spinal tissue, or a combination thereof. A tissue may comprise cells representative of a blood-brain barrier. A tissue may comprise a skin tissue, breast tissue, bladder tissue, kidney tissue, liver tissue, colon tissue, thyroid tissue, cervical tissue, prostate tissue, lung tissue, heart tissue, muscle tissue, pancreas tissue, anal tissue, bile duct tissue, a bone tissue, uterine tissue, ovarian tissue, endometrial tissue, vaginal tissue, vulvar tissue, stomach tissue, ocular tissue, nasal tissue, sinus tissue, penile tissue, salivary gland tissue, gut tissue, gallbladder tissue, gastrointestinal tissue, bladder tissue, brain tissue, spinal tissue, a blood sample, or any combination thereof. The tissue may be blood vessels.

The term "numerical aperture" as used herein, generally refers to a dimensionless number that characterizes the range of angles over which the system can accept or emit light. Numerical aperture may be used in microscopy to describe the acceptance cone of an objective (and hence its light-gathering ability and resolution).

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The methods and systems disclosed herein may be used to form a depth profile of a sample of tissue by utilize scanning patterns that move an imaging beam focal point through the sample in directions that are slanted or angled with respect to the optical axis, in order to improve the resolution of the optical system imaging the samples (e.g., in vivo biologic tissues). The scanner can move its focal points in a line or lines and/or within a plane or planes that are slanted with respect to the optical axis in order to create a depth profile of tissue. The depth profile can provide a projected vertical cross section image generally or approximately representative of a cross section of the tissue that can be used to identify a possible disease state of the tissue. The methods and systems may provide a projected vertical cross section image of an in vivo sample of intact biological tissue formed from depth profile image components (e.g. scanned pattern of focal points). The methods and systems disclosed herein may also produce an image of tissue cross section that is viewed as a tissue slice but may represent different X-Y positions.

According to some embodiments the methods and systems disclosed herein may utilize a slanted plane or planes (or slanted focal plane or planes) formed by a scanning pattern of focal points within the slanted plane or planes. A system that can simultaneously control the X, Y, and Z positions of a focused spot may move the focus through a trajectory in the tissue. The trajectory can be predetermined, modifiable or arbitrary. A substantial increase in resolution may occur when scanning at an angle to the vertical Z axis (i.e., optical axis). The effect may arise, for example, because the intersection between a slanted plane and the point spread function (PSF) is much smaller than the PSF projection in the XZ or YZ plane. Thus, the effective PSF for a focused beam moved along a slanted line or in a slated plane may be smaller as the slant angle increases, approaching the lateral PSF resolution at an angle of 90° (at which point a scan direction line or scan plane can lie within the XY (lateral) plane). Slanted scanning or imaging as described herein, may be used with any type of return signal. Non-limiting examples of return signals can include generated signals described elsewhere herein.

A depth profile through tissue can be scanned at an angle (e.g., more than 0° and less than 90°) with respect to the optical axis, to ensure a portion of the scan trajectory is moving the focus in the Z direction. In some examples, modest slant angles may produce a substantial improvement in resolution. The effective PSF size can be approximated as $PSF_{lateral}/\sin(\theta)$ for modest angles relative to the Z axis, where $\theta$ is the angle between the z axis and the imaging axis. Additional detail may be found in FIG. 3. Thus, at a scan angle of 45°, the resolution along the depth axis of the slanted plane may be a factor of 1.414 larger than the lateral resolution. With submicron lateral resolution, near or submicron slant resolution may be achieved depending on the scan angle. The process may produce cross sectional resolution that is achievable with much higher numerical aperture (NA) optical systems. By operating at a more modest NA, the optics may be more robust to off axis aberrations and can scan larger fields of view and/or greater depths. Additionally, operating at a more modest NA may enable a smaller footprint for an imaging device while maintaining a high resolution.

When the projected cross section image is constructed, the depth profile information derived from the generated signals resulting from the slant scanning, may be projected onto the XZ or YZ plane to create an image plane. In this situation, there may be no distortion in depths of structures relative to the surface of the tissue. This projected cross section image, in some representative embodiments, can comprise data corresponding to a plane optically sliced at one or more angles to the vertical. A projected cross section image can have vastly improved resolution while still representing the depths of imaged structures or tissue.

Methods for Generating a Depth Profile

Disclosed herein are methods for generating a depth profile of a tissue of a subject. In an aspect, a method for generating a depth profile of a tissue of a subject may comprise using an optical probe to transmit an excitation light beam from a light source towards a surface of the tissue, which excitation light beam, upon contacting the tissue, generate signals indicative of an intrinsic property of the tissue; using one or more focusing units in the optical probe to simultaneously adjust a depth and a position of a focal point of the excitation light beam in a scanning pattern; detecting at least a subset of the signals generated upon contacting the tissue with the excitation light beam; and using one or more computer processors programmed to process the at least the subset of the signals detected to generate the depth profile of the tissue. The scanning pattern can comprise a plurality of focal points. The method described herein for generating a depth profile can alternatively utilize a combination of two or more light beams that are either continuous or pulsed and are collocated at the focal point.

The depth profile can be generated by scanning a focal point in a in a scanning pattern that includes one or more slanted directions. The scanning may or may not be in a single plane. The scanning may be in a slanted plane or planes. The scanning may be in a complex shape, such as a spiral, or in a predetermined, variable, or random array of points. A scanning pattern, a scanning plane, a slanted plane, and/or a focal plane may be a different plane from a visual or image cross section that can be created from processed generated signals. The image cross section can be created from processed generated signals resulting from moving imaging focal points across a perpendicular plane, a slanted plane, a non-plane pattern, a shape (e.g., a spiral, a wave, etc.), or a random or pseudorandom assortment of focal points.

The depth profile can be generated in real-time. For example, the depth profile may be generated while the optical probe transmits one or more excitation light beams from the light source towards the surface of the tissue. The depth profile may be generated at a frame rate of at least 1 frames per second (FPS), 2 FPS, 3 FPS, 4 FPS, 5 FPS, 10 FPS, or greater. In some cases, the depth profile may be generated at a frame rate of at most 10 FPS, 5 FPS, 4 FPS, 3 FPS, 2 FPS, or less. Frame rate may refer to the rate at which an imaging device displays consecutive images called frames. An image frame of the depth profile can provide a cross-sectional image of the tissue.

The image frame, or the area of an image, may be a quadrilateral with any suitable dimensions. An image frame may be rectangular, in some cases with equal sides (e.g., square), for example, depicting a 200 μm by 200 μm cross-section of the tissue. The image frame may depict a cross-section of the tissue having dimensions of at least about 50 μm by 50 μm, 100 μm by 100 μm, 150 μm by 150 μm, 200 μm by 200 μm, 250 μm by 250 μm, 300 μm by 300 μm, or greater. In some cases, the image frame may depict a cross-section of the tissue having dimensions of at most about 300 μm by 300 μm, 250 μm by 250 μm, 200 μm by 200 μm, 150 μm by 150 μm, 100 μm by 100 μm, 50 μm by 50 μm, or smaller. The image frame may not have equal sides.

The image frame may be at any angle with respect to the optical axis. For example, the image frame may be at an angle that is greater than about 0°, 5°, 10°, 15°, 20°, 25°, 30°, 35°, 40°, 45°, 50°, 60°, 70°, 80°, 90°, or more, with respect to the optical axis. The image frame may be at an angle that is less than or equal to about 90°, 85°, 80°, 75°, 70°, 65°, 60°, 50°, 40°, 30°, 20°, 10°, 5°, or less, with respect to the optical axis. In some cases, the angle is between any two of the values described above or elsewhere herein, e.g., between 0° and 50°.

The image frame may be in any design, shape, or size. Examples of shapes or designs include but are not limited to: mathematical shapes (e.g., circular, triangular, square, rectangular, pentagonal, or hexagonal), two-dimensional geometric shapes, multi-dimensional geometric shapes, curves, polygons, polyhedral, polytopes, minimal surfaces, ruled surfaces, non-orientable surfaces, quadrics, pseudospherical surfaces, algebraic surfaces, miscellaneous surfaces, Riemann surfaces, box-drawing characters, Cuisenaire rods, geometric shapes, shapes with metaphorical names, symbols, Unicode geometric shapes, other geometric shapes, or partial shapes or combination of shapes thereof. The image frame may be a projected image cross section image as described elsewhere herein.

The excitation light beam may be ultrashort pulses of light. Ultrashort pulses of light can be emitted from an ultrashort pulse laser (herein also referred to as an "ultrafast pulse laser"). Ultrashort pulses of light can have high peak intensities leading to nonlinear interactions in various materials. Ultrashort pulses of light may refer to light having a full width of half maximum (FWHM) on the order of femtoseconds or picoseconds. In some examples, an ultrashort pulse of light has a FWHM of at least about 1 femtosecond, 10 femtoseconds, 100 femtoseconds, 1 picosecond, 100 picoseconds, or 1000 picoseconds or more. In some instances, an ultrashort pulse of light may be a FWHM of at most about 1000 picoseconds, 100 picoseconds, 1 picosecond, 100 femtoseconds, 10 femtoseconds, 1 femtosecond or less. Ultrashort pulses of light can be characterized by several parameters including pulse duration, pulse repetition rate, and average power. Pulse duration can refer to the FWHM of the optical power versus time. Pulse repetition rate can refer to the frequency of the pulses or the number of pulses per second.

The probe can also have other sensors in addition to the power sensor. The information from the sensors can be used or recorded with the depth profile to provide additional enhanced information with respect to the probe and/or the subject. For example, other sensors within the probe can comprise probe position sensors, GPS sensors, temperature sensors, camera or video sensors, dermatascopes, accelerometers, contact sensors, and humidity sensors.

Non-limiting examples of ultrashort pulse laser technologies include titanium (Ti):Sapphire lasers, mode-locked diode-pumped lasers, mode-locked fiber lasers, and mode-locked dye lasers. A Ti:Sapphire laser may be a tunable laser using a crystal of sapphire ($Al_2O_3$) that is doped with titanium ions as a lasing medium (e.g., the active laser medium which is the source of optical gain within a laser). Lasers, for example diode-pumped laser, fiber lasers, and dye lasers, can be mode-locked by active mode locking or passive mode locking, to obtain ultrashort pulses. A diode-pumped laser may be a solid-state laser in which the gain medium comprises a laser crystal or bulk piece of glass (e.g., ytterbium crystal, ytterbium glass, and chromium-doped laser crystals). Although the pulse durations may not be as short as those possible with Ti:Sapphire lasers, diode-pumped ultrafast lasers can cover wide parameter regions in terms of pulse duration, pulse repetition rate, and average power. Fiber lasers based on glass fibers doped with rare-earth elements such as erbium, ytterbium, neodymium, dysprosium, praseodymium, thulium, or combinations thereof can also be used. In some cases, a dye laser comprising an organic dye, such as rhodamine, fluorescein, coumarin, stilbene, umbelliferone, tetracene, malachite green, or others, as the lasing medium, in some cases as a liquid solution, can be used.

The light source providing ultrashort pulses of light can be a wavelength-tunable, ultrashort-pulsed Ti:Sapphire laser. A Ti:Sapphire laser can be a mode-locked oscillator, a chirped-pulse amplifier, or a tunable continuous wave laser. A mode-locked oscillator can generate ultrashort pulses with a duration between about a few picoseconds and about 10 femtoseconds, and in cases about 5 femtoseconds. The pulse repetition frequency can be about 70 to 90 megahertz (MHz). The term 'chirped-pulse' generally refers to a special construction that can prevent the pulse from damaging the components in the laser. In a 'chirped-pulse' laser, the pulse can be stretched in time so that the energy is not all located at the same point in time and space, preventing damage to the optics in the amplifier. The pulse can then be optically amplified and recompressed in time to form a short, localized pulse.

Ultrashort pulses of light can be produced by gain switching. In gain switching, the laser gain medium is pumped with, e.g., another laser. Gain switching can be applied to various types of lasers including gas lasers (e.g., transversely excited atmospheric (TEA) carbon dioxide lasers). Adjusting the pulse repetition rate can, in some cases, be more easily accomplished with gain-switched lasers than mode-locked lasers, as gain-switching can be controlled with an electronic driver without changing the laser resonator setup. In some cases, a pulsed laser can be used for optically pumping a gain-switched laser. For example, nitrogen ultraviolet lasers or excimer lasers can be used for pulsed pumping of dye lasers. In some cases, Q-switching can be used to produce ultrafast pulses of light.

Tissue and cellular structures in the tissue can interact with the excitation light beam in a wavelength dependent manner and generate signals that relate to intrinsic properties of the tissue. The signals generated can be used to evaluate a normal state, an abnormal state, a cancerous state, or other features of the tissue in a subject pertaining to the health, function, treatment, or appearance of the tissue, such as skin tissue. The subset of the signals generated and collected can include at least one of second harmonic generation (SHG) signals, third harmonic generation (THG) signals, polarized light signals, and autofluorescence signals. A slanted plane imaging technique may be used with any generated signals as described elsewhere herein.

Higher harmonic generation microscopy (HHGM) (e.g., second harmonic generation and third harmonic generation), based on nonlinear multiphoton excitation, can be used to examine cellular structures in live and fixed tissues. SHG can generally refer to a nonlinear optical process in which photons with about the same frequency interact with a nonlinear material and effectively "combine" to generate new photons with about twice the energy, and therefore about twice the frequency and about half ($\frac{1}{2}$) the wavelength of the initial photons. Similarly, THG can generally refer to a nonlinear optical process in which photons with about the same frequency interact with a nonlinear material and effectively "combine" to generate new photons with about three times the energy, and therefore about three times the frequency and about one-third ($\frac{1}{3}$) the wavelength of the initial photons. Second harmonic generation (SHG) and third harmonic generation (THG) of ordered endogenous molecules, such as but not limited to collagen, microtubules, and muscle myosin, can be obtained without the use of exogenous labels and provide detailed, real-time optical reconstruction of molecules including fibrillar collagen, myosin, microtubules as well as other cellular information such as membrane potential and cell depolarization. The ordering and organization of proteins and molecules in a tissue, for example collagen type I and II, myosin, and microtubules, can generate, upon interacting with light, signals that can be used to evaluate the cancerous state of a tissue. SHG signals can be used to detect changes such as changes in collagen fibril/fiber structure that may occur in diseases including cancer, fibrosis, and connective tissue disorders. Various biological structures can produce SHG signals. In some cases, the labeling of molecules with exogenous probes and contrast enhancing agents, which can alter the way a biological system functions, may not be used. In some cases, methods herein for identifying a disease in an epithelial tissue of a subject may be performed in the absence of administering a contrast enhancing agent to the subject.

Another type of signal that can be generated and collected for determining a disease in a tissue may be autofluorescence. Autofluorescence can generally refer to light that is naturally emitted by certain biological molecules, such as proteins, small molecules, and/or biological structures. Tissue and cells can comprise various autofluorescent proteins and compounds. Well-defined wavelengths can be absorbed by chromophores, such as endogenous molecules, proteins, water, and adipose that are naturally present in cells and tissue. Non-limiting examples of autofluorescent fluorophores that can be found in tissues include polypeptides and proteins comprising aromatic amino acids such as tryptophan, tyrosine, and phenylalanine which can emit in the UV range and vitamin derivatives which can emit at wavelengths in a range of about 400 nm to 650 nm, including retinol, riboflavin, the nicotinamide ring of NAD(P)H derived from niacin, and the pyridolamine crosslinks found in elastin and some collagens, which are based on pyridoxine (vitamin B6).

The autofluorescence signal may comprise a plurality of autofluorescence signals. One or more filters may be used to separate the plurality of autofluorescence signals into one or more autofluorescence channels. For example, different parts of a tissue can fluoresce at different wavelengths, and wavelength selective filters can be used to direct each fluorescence wavelength to a different detector. One or more monochromators or diffraction gratings may be used to separate the plurality of autofluorescence signals into one or more channels. Another type of signal that can be generated or collected for determining a disease in a tissue may be reflectance confocal microscopy (RCM) signals. RCM can use light that is reflected of a sample, such as a tissue, when a beam of light from an optical probe is directed to the sample. RCM signals may be a small fraction of the light that is directed to the sample. The RCM signals may be collected by rejecting out of focus light. The out of focus light may or may not be rejected using a pinhole, a single mode fiber optic, or a similar physical filter. The interaction of the sample with the beam of light may or may not alter the polarization of the RCM signal. Different components of the sample may alter the polarization of the RCM signals to different degrees. The use of polarization selective optics in an optical path of the RCM signals may allow a user to select RCM signal from a given component of the sample. The system can select, split, or amplify RCM signals that correspond to different anatomical features or characteristics to provide additional tissue data. For example, based on the changes in polarization detected by the system, the system can select or amplify RCM signal components corresponding to melanin deposits by selecting or amplifying the RCM signal that associated with melanin, using the polarization selective optics. Other tissue components including but are not limited to collagen, keratin, elastin can be identified using the polarization selective optics. Non-limiting examples of generated signals that may be detected are described elsewhere herein.

An ultra-fast pulse laser may produce pulses of light with pulse durations at most 500 femtoseconds, 450 femtoseconds, 400 femtoseconds, 350 femtoseconds, 300 femtoseconds, 250 femtoseconds, 200 femtoseconds, 150 femtoseconds, 100 femtoseconds, or shorter. In some cases, the pulse duration is about 150 femtoseconds. In some cases, an ultra-fast pulse laser may produce pulses of light with pulse durations at least 100 femtoseconds, 150 femtoseconds, 200 femtoseconds, 250 femtoseconds, 300 femtoseconds, 350 femtoseconds, 400 femtoseconds, 450 femtoseconds, 500 femtoseconds, or shorter. The pulse repetition frequency of an ultra-fast pulse laser can be at least 10 MHz, 20 MHz, 30 MHz, 40 MHz, 50 MHz, 60 MHz, 70 MHz, 80 MHz, 90 MHz, 100 MHz, or greater. In some cases, the pulse repetition frequency of an ultra-fast pulse laser can be at most 100 MHz, 90 MHz, 80 MHz, 70 MHz, 60 MHz, 50 MHz, 40 MHz, 30 MHz, 20 MHz, 10 MHz, or less. In some cases, the pulse repetition frequency is about 80 MHz.

The collected signals can be processed by a programmed computer processor to generate a depth profile. The signals can be transmitted wirelessly to a programmed computer processor. As an alternative, the signals may be transmitted through a wired connection to a programmed computer processor. The signals or a subset of the signals relating to an intrinsic property of the tissue can be used to generate a depth profile with the aid of a programmed computer processor. The collected signals and/or generated depth profile can be stored electronically. In some cases, the signals and/or depth profile are stored until deleted by a user, such as a surgeon, physician, nurse, or other healthcare practitioner. When used for diagnosis and/or treatment, the depth profile may be provided to a user in real-time. A depth profile provided in real-time can be used as a pre-surgical image to identify the boundary of a disease, for example skin cancer. The depth profile can provide a visualization of the various layers of tissue, such as skin tissue, including the epidermis, the dermis, and/or the hypodermis. The depth profile can extend at least below the stratum corneum, the stratum lucidum, the stratum granulosum, the stratum spinosum or the squamous cell layer, and/or the basal cell layer. In some cases, the depth profile may extend at least 250 µm, 300 µm, 350 µm, 400 µm, 450 µm, 500 µm, 550 µm, 600 µm, 650 µm, 700 µm, 750 µm, or farther below the surface of the tissue. In some cases, the depth profile may extend at most 750 µm, 700 µm, 650 µm, 600 µm, 550 µm, 500 µm, 450 µm, 400 µm, 350 µm, 300 µm, 250 µm, or less below the surface of the tissue. In some cases, the depth profile extends between about 100 µm and 1 mm, between about 200 µm and 900 µm, between about 300 µm and 800 µm, between about 400 µm and 700 µm, or between about 500 µm and 600 µm below the surface of the tissue.

The method may further comprise processing the depth profile using the one or more computer processors to identify a disease in the tissue. The identification of the disease in the tissue may comprise one or more characteristics. The one or more characteristics may provide a quantitative value or values indicative of one or more of the following: a likelihood of diagnostic accuracy, a likelihood of a presence of a disease in a subject, a likelihood of a subject developing a disease, a likelihood of success of a particular treatment, or any combination thereof. The one or more computer processors may also be configured to predict a risk or likelihood of developing a disease, confirm a diagnosis or a presence of a disease, monitor the progression of a disease, and monitor the efficacy of a treatment for a disease in a subject.

The method may further comprise contacting the tissue of the subject with the optical probe. The contact may be direct or indirect contact. If the contact is a direct contact, performing the contact may comprise placing the optical probe next to the tissue of the subject without an intervening layer. If the contact is an indirect contact, performing the contact may comprise placing the optical probe next to the tissue of the subject with one or more intervening layers. The one or more intervening layers may comprise, but are not limited to, clothes, medical gauzes, and bandages. The contact may be monitored such that when contact between the surface of the epithelial tissue and the optical probe is disrupted, a shutter positioned in front of the detector (e.g., relative to the path of light) can be activated and block incoming light.

According to some representative embodiments, the scanning pattern may follow a slanted plane. The slanted plane may be positioned along a direction that is angled with respect to an optical axis of the optical probe. The angle between the slanted plane and the optical axis may be at most 45°. The angle between the slanted plane and the optical axis may be greater than or equal to about 5°, 10°, 15°, 20°, 25°, 30°, 35°, 40°, 45°, 55°, 60°, 65°, 70°, 75°, 80°, 85°, or greater. In other cases, the angle between the slanted plane and the optical axis may be less than or equal to about 85°, 80°, 75°, 70°, 65°, 60°, 55°, 50°, 45°, 35°, 30°, 25°, 20°, 15°, 10°, 5°, or less. In some cases, the angle between the slanted plane and the optical axis may be between any of the two values described above, for example, between about 5° and 50°.

According to various representative embodiments, the scanning path or pattern may follow one or more patterns that are designed to obtain enhanced, improved, or optimized image resolution. The scanning path or pattern may comprise, for example, one or more perpendicular planes, one or more slanted planes, one or more spiral focal paths, one or more zigzag or sinusoidal focal paths, or any combination thereof. The scanning path or pattern may be configured to maintain the scanning focal points near the optical element's center while moving in slanted directions. The scanning path or pattern may be configured to maintain the scanning focal points near the center of the optical axis (e.g., the focal axis).

The scanning pattern of the plurality of focal points may be selected by an algorithm. For example, a series of images may be taken using focal points moving at one or more scan angles (with respect to the optical axis). The scanning pattern may include perpendicular scanning and/or slant scanning. Depending upon the quality of the images taken, one or more additional images may be taken using different scan angles or combinations thereof, selected by an algorithm. As an example, if an image taken using a perpendicular scan or a smaller angle slant scan is of low quality, a computer algorithm may direct the system to take images using a combination of scan directions or using larger scan angles. If the combination of scan patterns results in an improved image quality, then the imaging session may continue using that combination of scan patterns.

Figure 2:
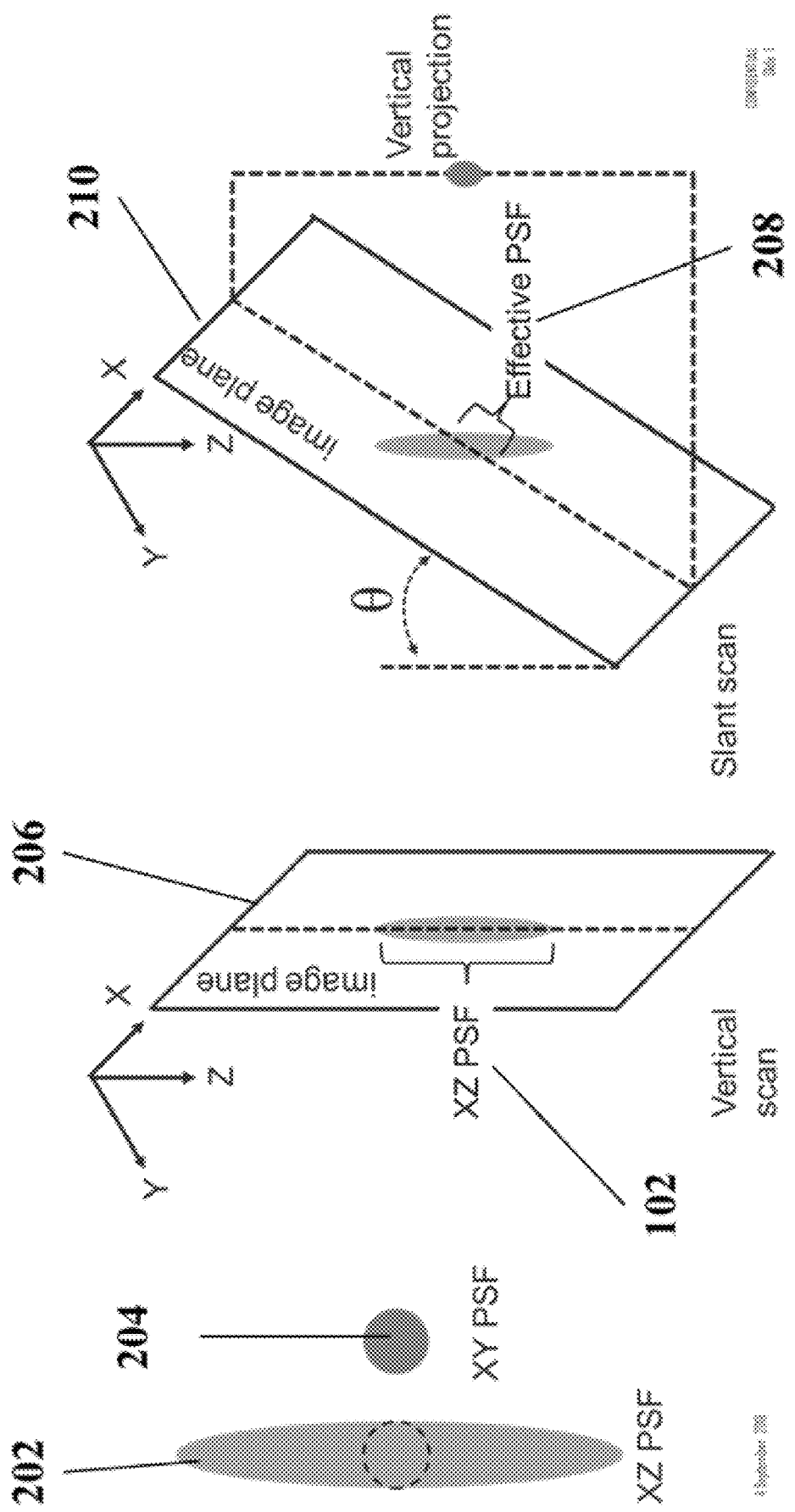
FIG. 2 shows an example of using a slanted plane for a slanted scanning process.

FIG. 2 shows an example of using a scan pattern on a slanted plane for a slant scanning process. Diffraction may create a concentrated region of light called the point spread function (PSF). In three dimensions, the PSF may be an ellipsoid that is elongated in the Z direction (the direction parallel to the optical axis) relative to the XY plane. The size of the PSF may dictate the smallest feature that the system can resolve, for example, the system's imaging resolution. In FIG. 2, for normal scanning process, the PSF 202 projected on vertical plane XZ 206 is in oval shape, and the PSF 204 projected on plane XY (plane XY is not shown) is in circle shape. The plane XZ 206 is parallel to the optical axis. For the slant scanning process, a substantial benefit in resolution may occur because the effective PSF 208 (the intersection between the slanted plane 210 and the PSF 202) may be much smaller than the PSF 202 projected on the XZ plane 206. The angle θ (slant angle) between the slanted plane 210 and the optical axis may be greater than or equal to about 5°, 10°, 15°, 20°, 25°, 30°, 35°, 40°, 45°, 55°, 60°, 65°, 70°, 75°, 80°, 85°, or greater. In other cases, the angle θ between the slanted plane 210 and the optical axis may be less than or equal to about 85°, 80°, 75°, 70°, 65°, 60°, 55°, 50°, 45°, 35°, 30°, 25°, 20°, 15°, 10°, 5°, or less. In some cases, the angle θ between the slanted plane 210 and the optical axis may be between any of the two values described above, for example, between about 5° and 50°.

Figure 3:
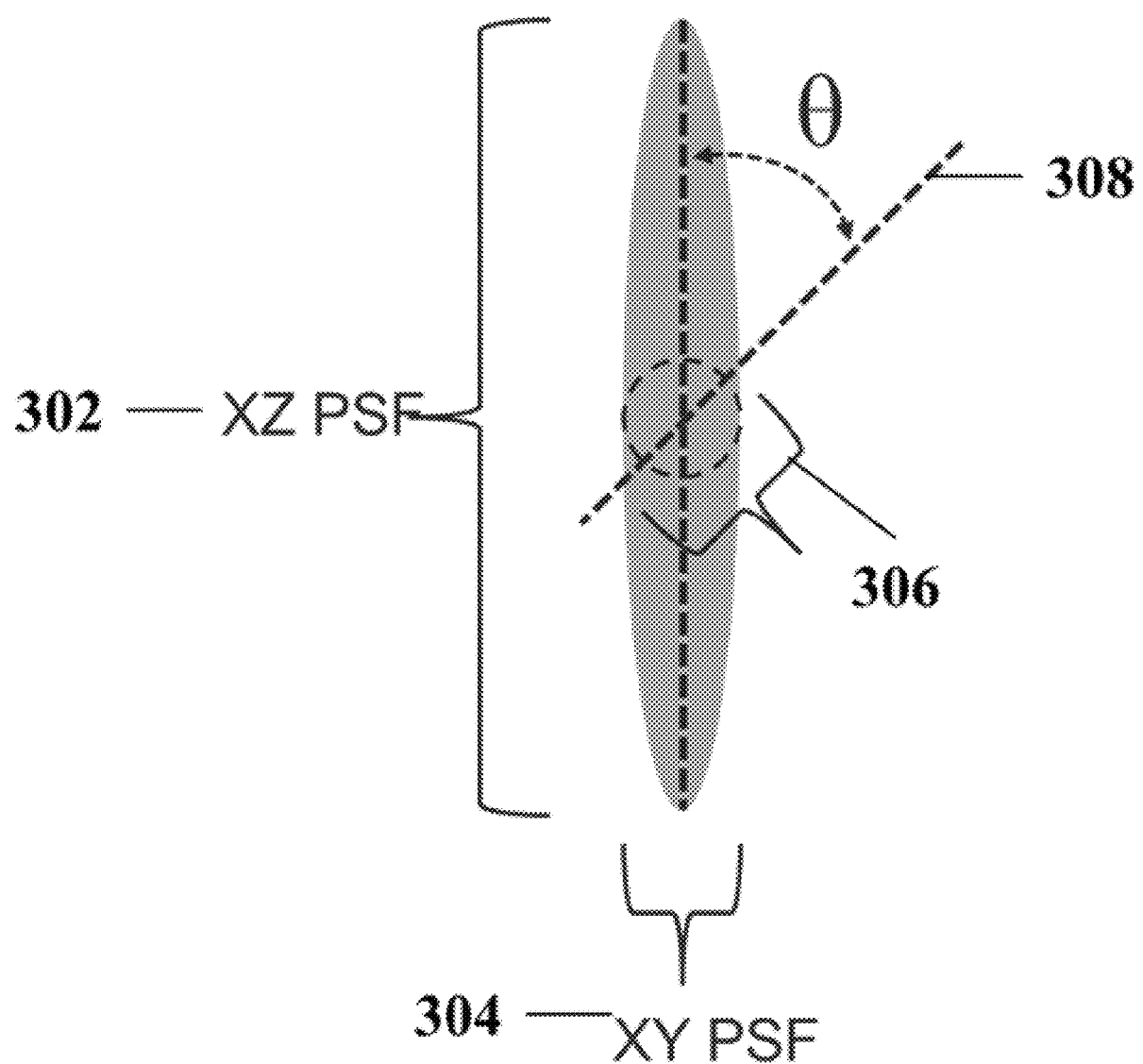
FIG. 3 shows an example of an enlarged view of the effective point spread function projected on a slanted plane.

FIG. 3 shows an example of an enlarged view of the effective PSF projected on a slanted plane. In FIG. 3, for normal scanning process, the point spread function (PSF) 302 on plane XZ (plane XZ is not shown) is in oval shape, and the PSF 304 on plane XY (plane XY is not shown) is in circle shape. For the slant scanning process, a substantial benefit in resolution may occur because the effective PSF 306 (the intersection between the slanted plane 308 and the PSF 302) may be much smaller than the PSF 302 projected on the XZ plane. The angle θ between the slanted plane 308 and the optical axis may be greater than or equal to about 5°, 10°, 15°, 20°, 25°, 30°, 35°, 40°, 45°, 55°, 60°, 65°, 70°, 75°, 80°, 85°, or greater. In other cases, the angle θ between the slanted plane 308 and the optical axis may be less than or equal to about 85°, 80°, 75°, 70°, 65°, 60°, 55°, 50°, 45°, 35°, 30°, 25°, 20°, 15°, 10°, 5°, or less. In the slanted scanning, the image resolution may be $PSF_{Slant} \leq PSF_{XY}/\sin\theta$, which shows that the effective PSF size can be approximated as $PSF_{xy}/\sin(\theta)$ for modest angles relative to the Z axis.

Figure 4:
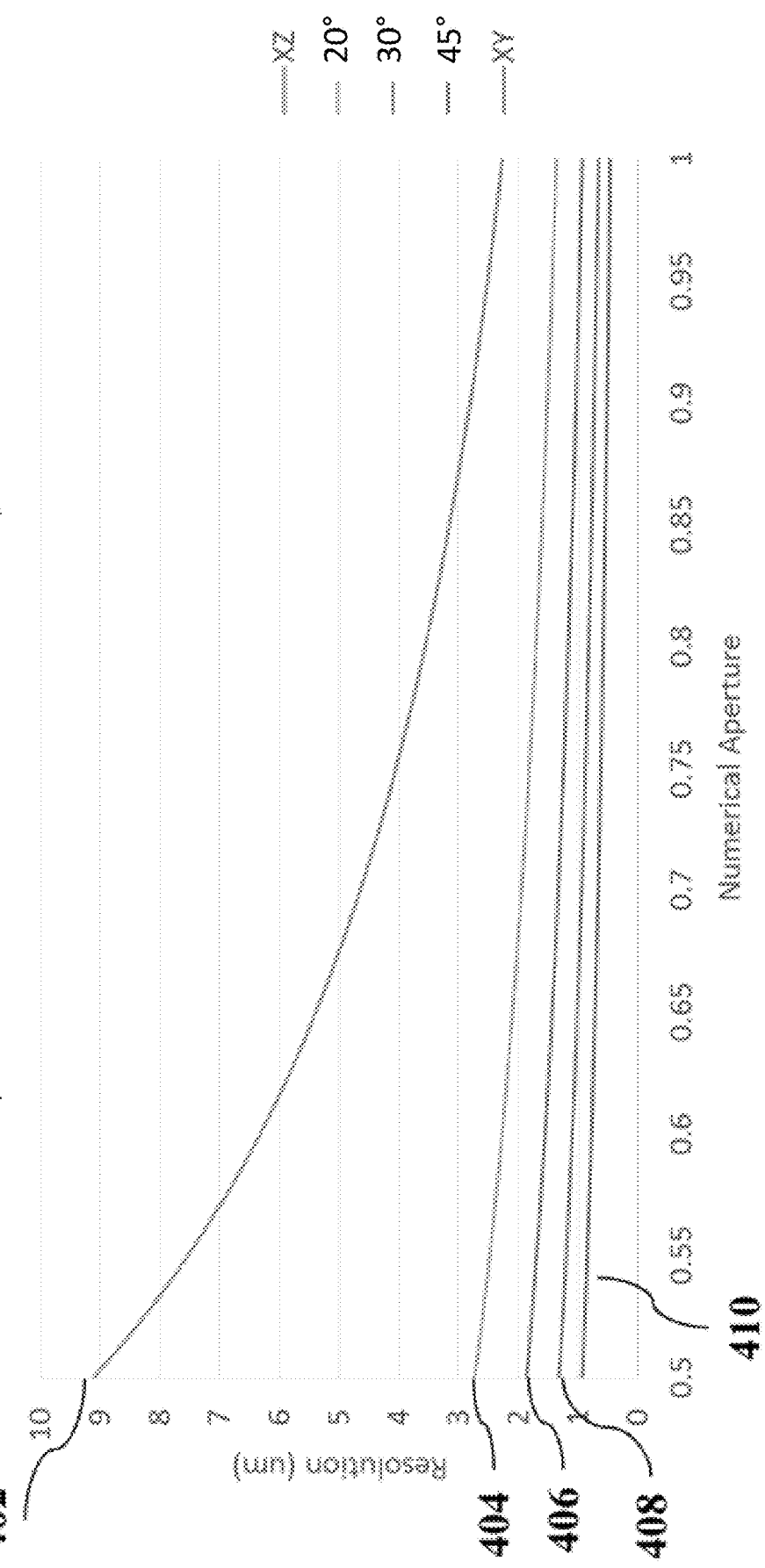
FIG. 4 shows an example of optical resolution (y-axis) changing with numerical aperture (x-axis) for various angles (θ).

FIG. 4 shows an example of optical resolution changing with θ and numerical aperture. In FIG. 4, the curve 402 represents the change of optical resolution versus numerical aperture for plane parallel to the optical axis; the curve 404 represents the change of optical resolution versus numerical aperture for slanted plane having an angle of 20° with the optical axis; the curve 406 represents the change of optical resolution versus numerical aperture for slanted plane having an angle of 30° with the optical axis; the curve 408 represents the change of optical resolution versus numerical aperture for slanted plane having an angle of 45° with the optical axis; the curve 410 represents the change of optical resolution versus numerical aperture for slanted plane having an angle of 90° with the optical axis. In FIG. 4, for the same value of numerical aperture, the resolution decreases as the θ increases; and for the same θ, the resolution decreases when numerical aperture increases.

Different scan modalities through the tissue that utilize any cross section of the ellipse can be created by independently controlling the X, Y, Z location of the excitation ellipsoid. Any continuous parametric equation that describes a 3-dimensional volume can be used to scan the structure. FIGS. 5A-5F show examples of scanning modalities.

Figure 5A:
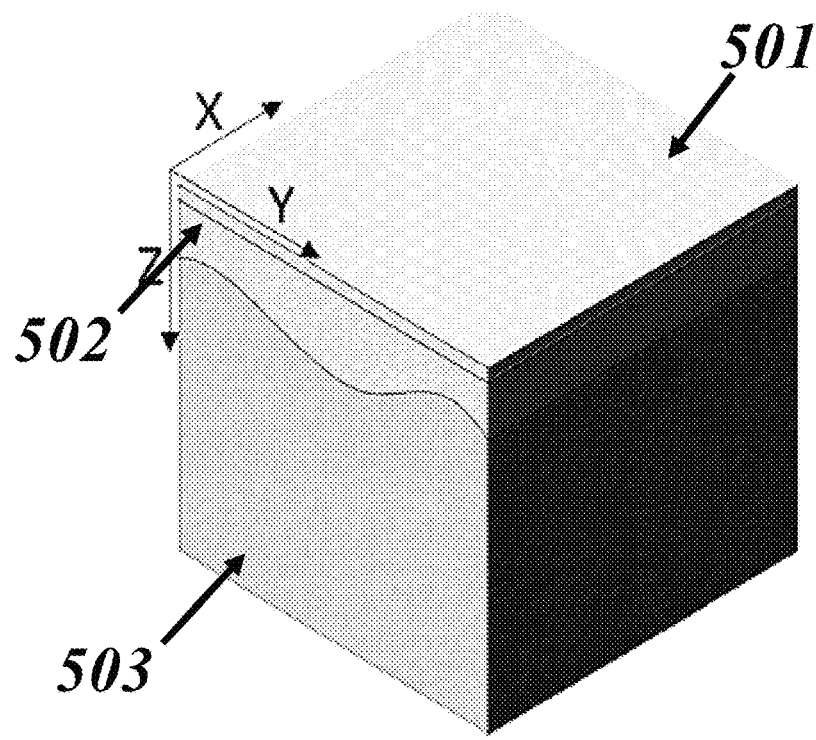
FIGS. 5A-5F show examples of various scanning modalities.
Figure 5B:
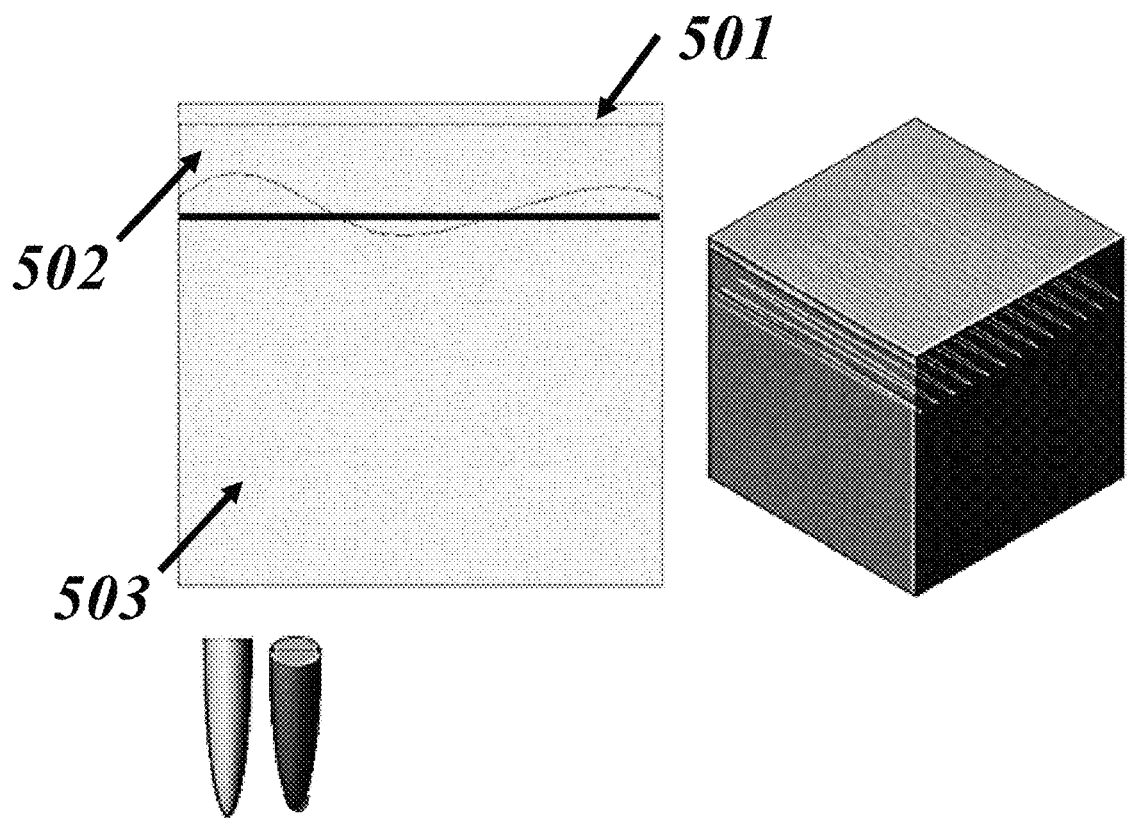
Figure 5C:
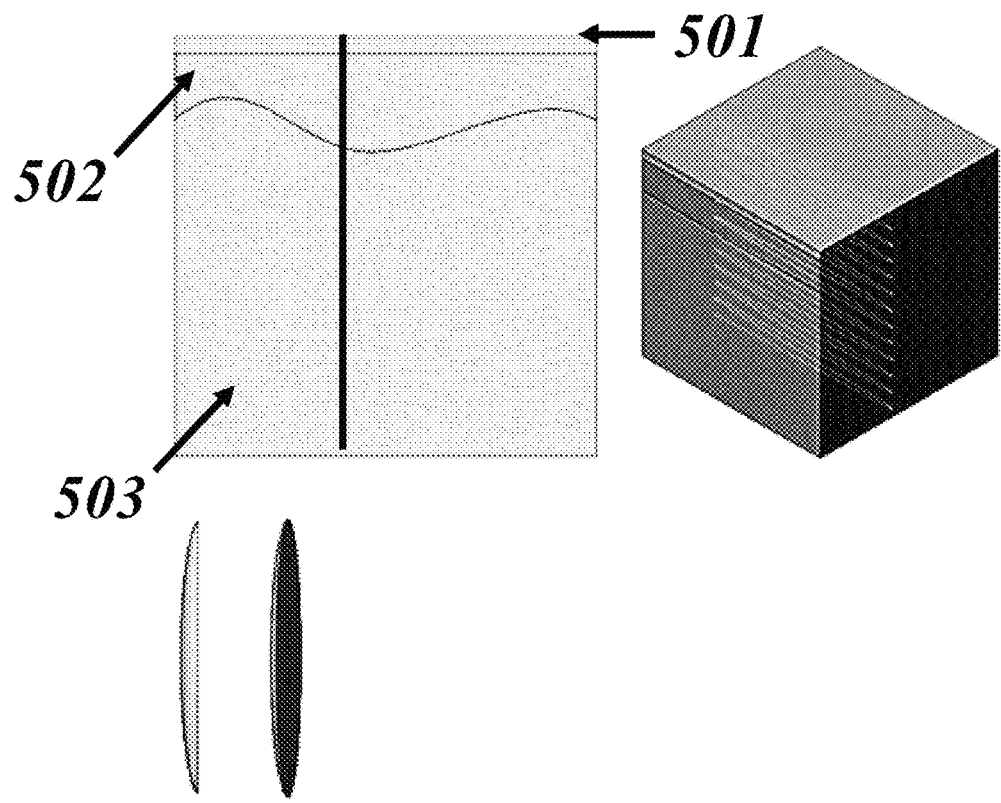
Figure 5D:
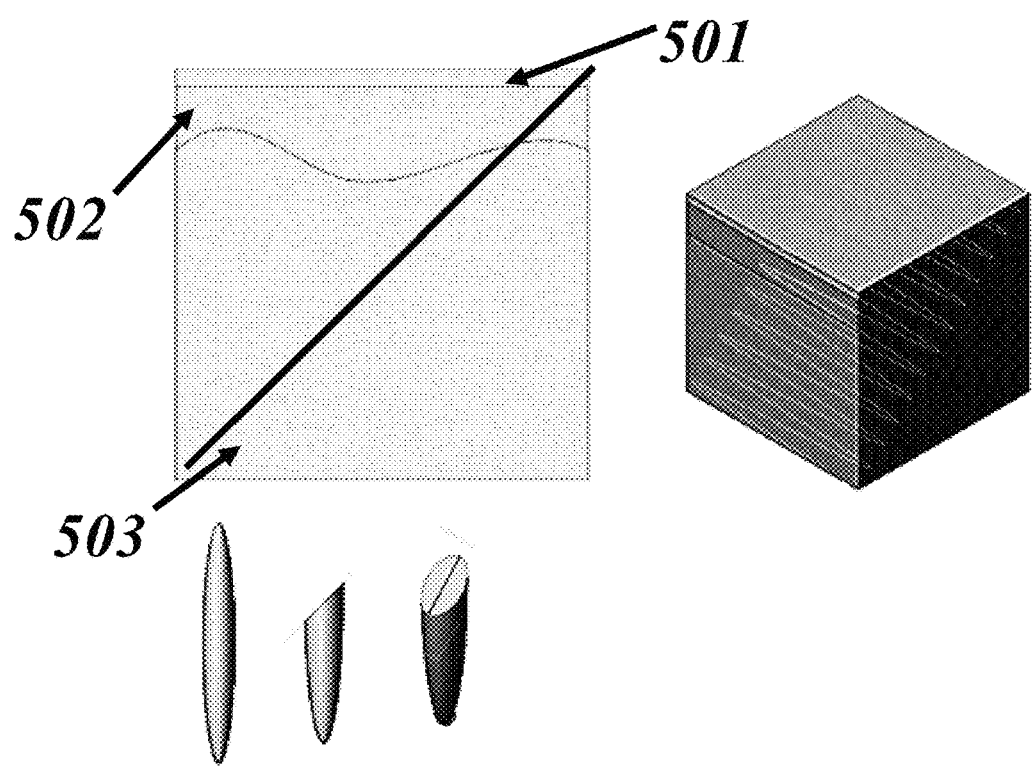
Figure 5E:
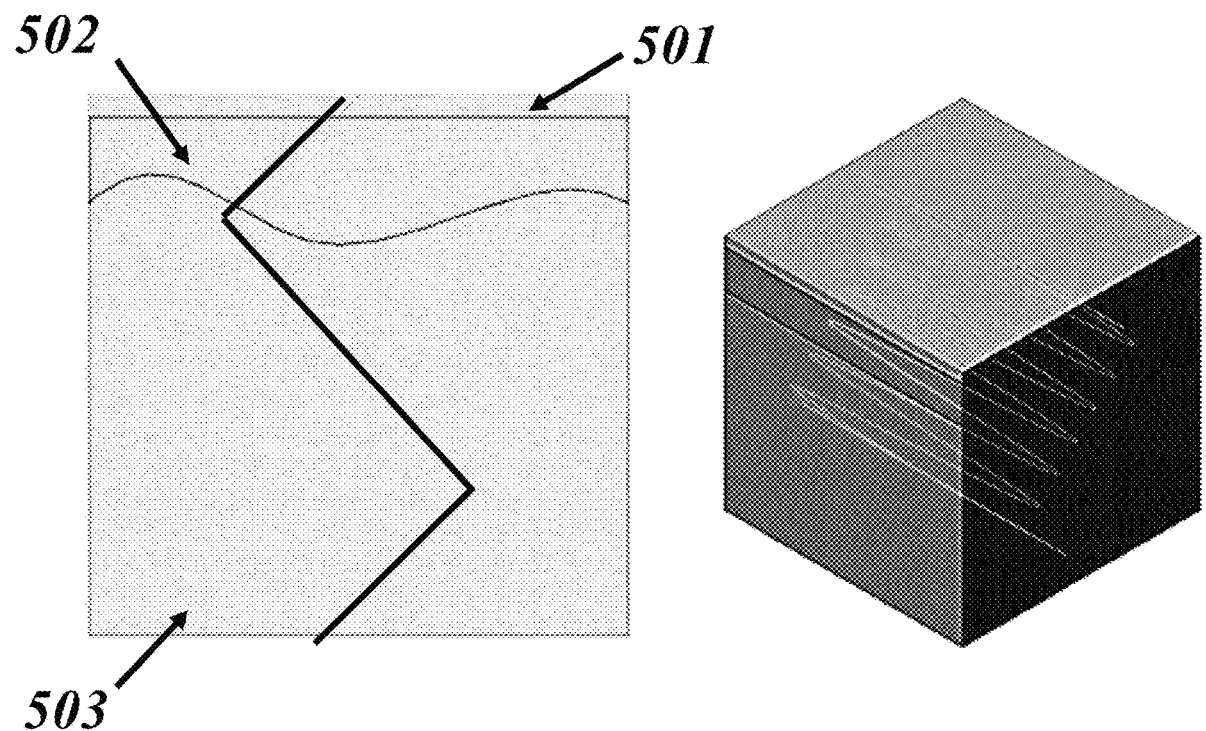

FIGS. 5A-5E shows an example of the volume that is scanned showing boundaries between the stratum corneum 501 the epidermis 502 and dermis 503. In FIG. 5A, XY and XZ are included in order to show the contrast in modalities. For each of FIGS. 5B-5F, the left image shows the side view of a scanned plane, and the right image shows the corresponding pattern of a scanning process in the three-dimensional volume. Additionally, the bottom-left images (below the left image in the plane of the figure) of FIGS. 5B-5D and 5F show the intersection between the PSF and a scan plane which represents the smallest spot size and resolvable feature for that plane. For instance, FIG. 5B shows the XY imaging, and FIG. 5C shows XZ imaging. In FIG. 5E, the left image shows the side view of the scanned plane, and the right image shows the pattern of the scanning process or geometry in the three-dimensional volume.

The benefit in resolution may occur when the scan pattern has a component in the X, Y, and Z directions, creating a slanted intersection of the PSF relative to the Z axis. There may be many different patterns, one example of which may be a single slanted plane that moves along a constant angle relative to the XZ plane. For instance, in FIG. 5D, a slanted plane moves along a 45° angle relative to the optical axis (or the XZ plane). The resolution may be XYresolution/sin(45 deg). The XZ resolution may measure five to ten times the XY resolution, which may be a large improvement in resolution.

Figure 5F:
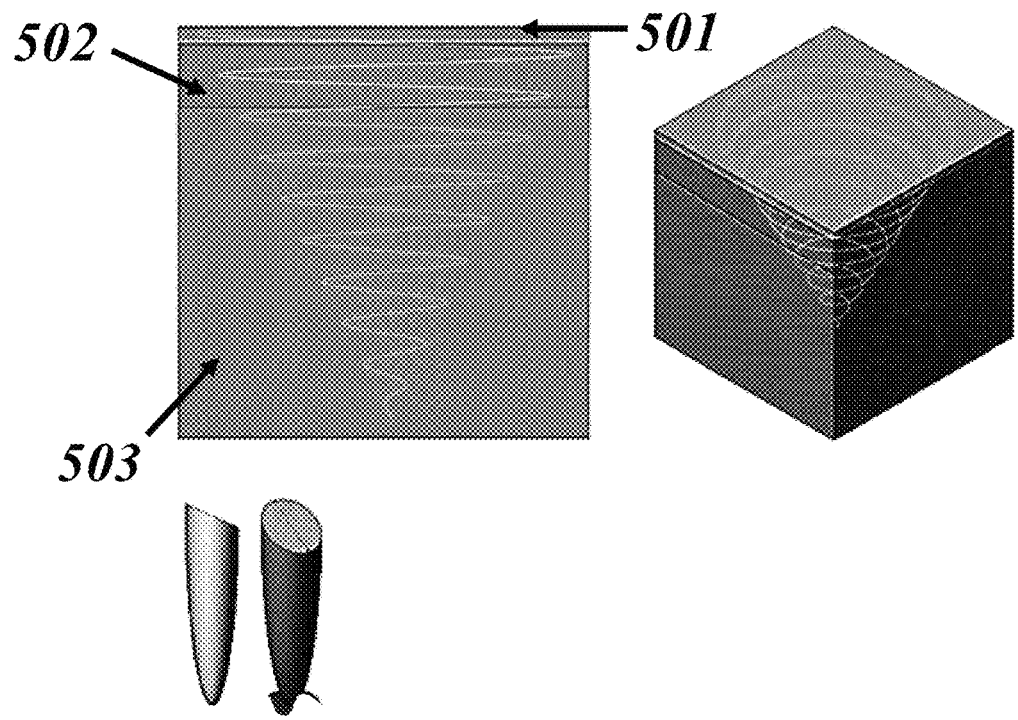

FIG. 5E shows serpentine imaging. Serpentine imaging may have the benefit of a slanted PSF, but by changing directions regularly keeps the scan closer to the central XZ plane. Optical aberrations may increase off axis, so this may be a technique to gain the benefit of the slanted PSF while minimizing the maximum distance from the centerline. The amplitude and rate of the oscillation in this serpentine can be varied. The serpentine scan may create a scan plane or image. FIG. 5F shows spiral image. Spiral imaging may have the benefit of a slanted PSF, but with higher scanning rates as a circular profile can be scanned faster than a back and forth raster pattern.

The method may be performed in an absence of removing the tissue from the subject. The method may be performed in an absence of administering a contrast enhancing agent to the subject.

The excitation light beam may comprise unpolarized light. In other embodiments, the excitation light beam may comprise polarized light. A wavelength of the excitation light beam can be at least about 400 nanometers (nm), 450 nm, 500 nm, 550 nm, 600 nm, 650 nm, 700 nm, 750 nm, 800 nm, 850 nm, 900 nm, 950 nm or longer. In some cases, a wavelength of the excitation light beam can be at most about 950 nanometers (nm), 900 nm, 850 nm, 800 nm, 750 nm, 700 nm, 650 nm, 600 nm, 550 nm, 500 nm, 450 nm, 400 nm or shorter. The wavelength of the pulses of light may be between about 700 nm and 900 nm, between about 725 nm and 875 nm, between about 750 nm and 850 nm, or between about 775 nm and 825 nm.

Multiple wavelengths may also be used. When multiple wavelengths of light are used, the wavelengths can be centered at least about 400 nm, 450 nm, 500 nm, 550 nm, 600 nm, 650 nm, 700 nm, 750 nm, 800 nm, 850 nm, 900 nm, 950 nm or longer with a bandwidth of at least about 10 nm, 20 nm, 30 nm, 40 nm, 50 nm, 75 nm, 100 nm, 125 nm, 150 nm, 175 nm, 200 nm, 225 nm, 250 nm, 275 nm, 300 nm or longer. For example, the wavelengths can be centered at about 780 nm with a bandwidth of about 50 nm (e.g., about ((780−(50/2))=755 nm) to about ((780+(50/2))=805 nm)). In some cases, the wavelengths can be centered at most about 950 nanometers (nm), 900 nm, 850 nm, 800 nm, 750 nm, 700 nm, 650 nm, 600 nm, 550 nm, 500 nm, 450 nm, 400 nm or shorter with a bandwidth of at least about 10 nm, 20 nm, 30 nm, 40 nm, 50 nm, 75 nm, 100 nm, 125 nm, 150 nm, 175 nm, 200 nm, 225 nm, 250 nm, 275 nm, 300 nm or longer.

The subset of the signals may comprise at least one of signal selected from the group consisting of second harmonic generation (SHG) signal, third harmonic generation (THG) signal, reflectance confocal microscopy (RCM) signal, and autofluorescence signal. SHG, THG, RCM, and autofluorescence are disclosed elsewhere herein. The subset of signals may comprise one or more generated signals as defined herein.

The collecting may be performed in a presence of ambient light. Ambient light can refer to normal room lighting, such as provided by various types of electric lighting sources including incandescent light bulbs or lamps, halogen lamps, gas-discharge lamps, fluorescent lamps, light-emitting diode (LED) lamps, and carbon arc lamps, in a medical examination room or an operating area where a surgical procedure is performed.

The simultaneously adjusting the depth and the position of the focal point of the excitation light beam along the slant scan, scan path or scan pattern may increase a maximum resolution depth of the depth profile. The maximum resolution depth after the increase may be at least about 1.1 times, 1.2 times, 1.5 times, 1.6 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, or greater of the original maximum resolution depth. In other embodiments, the maximum resolution depth after the increase may be at most about 3 times, 2.9 times, 2.8 times, 2.7 times, 2.6 times, 2.5 times, 2.4 times, 2.3 times, 2.2 times, 2.1 times, 2.0 times, 1.9 times, 1.8 times, 1.7 times, 1.6 times, 1.5 times, 1.4 times, or less of the original maximum resolution depth. The increase may be relative to instances in which the depth and the position of the focal point may be not simultaneously adjusted.

The signals indicative of the intrinsic property of the tissue may be detected by a photodetector. A power and gain of the photodetector sensor may be modulated to enhance image quality. The excitation light beam may be synchronized with sensing by the photodetector.

The RCM signals may be detected by a series of optical components in optical communication with a beam splitter. The beam splitter may be a polarization beam splitter, a fixed ratio beam splitter, a reflective beam splitter, or a dichroic beam splitter. The beam splitter may transmit greater than or equal to about 1%, 3%, 5%, 10%, 15%, 20%, 25%, 33%, 50%, 66%, 75%, 80%, 90%, 99% or more of incoming light. The beam splitter may transmit less than or equal to about 99%, 90%, 80%, 75%, 66%, 50%, 33%, 25%, 20%, 15%, 10%, 5%, 3%, 1%, or less of incoming light. The series of optical components may comprise one or more mirrors. The series of optical components may comprise one or more lenses. The one or more lenses may focus the light of the RCM signal onto a fiber optic. The fiber optic may be a single mode, a multi-mode, or a bundle of fiber optics. The focused light of the RCM signal may be aligned to the fiber using an adjustable mirror, a translation stage, or a refractive alignment element. The refractive alignment element may be a refractive alignment element as described elsewhere herein.

The method may be performed without penetrating the tissue of the subject. Methods disclosed herein for identifying a disease in a tissue of a subject can be used during and/or for the treatment of the disease, for example during Mohs surgery to treat skin cancer. In some cases, identifying a disease, for example a skin cancer, in an epithelial tissue of a subject can be performed in the absence of removing the epithelial tissue from the subject. This may advantageously prevent pain and discomfort to the subject and can expedite detection and/or identification of the disease. The location of the disease may be detected in a non-invasive manner, which can enable a user such as a healthcare professional (e.g., surgeon, physician, nurse, or other practitioner) to determine the location and/or boundary of the diseased area prior to surgery. Identifying a disease in an epithelial tissue of a subject, in some cases, can be performed without penetrating the epithelial tissue of the subject, for example by a needle.

The disease or condition may comprise a cancer. In some cases, a cancer may comprise thyroid cancer, adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g., Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g., uterine sarcoma), vaginal cancer, vulvar cancer, or Waldenstrom's macroglobulinemia. The disease may be epithelial cancer. The epithelial cancer may be skin cancer.

The method may further comprise processing the depth profile using the one or more computer processors to classify a disease of the tissue. The classification may identify the tissue as having the disease at an accuracy, selectivity, and/or specificity of at least about 10%, 20%, 30%, 40%, 50%, 60%, 70%, 80%, 90%, 95%, 98%, 99%, 99.9%, or more. The classification may identify the tissue as having the disease at an accuracy, selectivity, and/or specificity of at most about 99.9%, 99%, 98%, 95%, 90%, 80%, 70%, 60%, 50%, 40%, 30%, 20%, 10%, or less. The one or more computer processors may classify the disease using one or more computer programs. The one or more computer programs may comprise one or more machine learning techniques. The one or more machine learning techniques may be trained on a system other than the one or more processors.

The depth profile may have a resolution of at least about 0.5, 0.6, 0.7, 0.8, 0.9, 1, 2, 3, 4, 5, 6, 7, 8, 9, 10, 15, 20, 25, 30, 40, 50, 75, 100, 150, 200 microns, or more. The depth profile may have a resolution of at most about 200, 150, 100, 75, 50, 40, 30, 25, 20, 15, 10, 9, 8, 7, 6, 5, 4, 3, 2, 1, 0.9, 0.8, 0.7, 0.6, 0.5 microns, or less. For example, the depth profile may be able to resolve an intercellular space of 1 micron.

The method may further comprise measuring a power of the excitation light beam. A power meter may be used to measure the power of the excitation light beam. The power meter may measure the power of the excitation light beam in real time. The one or more computer processors may normalize a signal for the measured power of the excitation light beam. The normalized signal may be normalized with respect to an average power, an instantaneous power (e.g., the power read at the same time as the signal), or a combination thereof. The one or more computer processors may generate a normalized depth profile. The normalized depth profile may be able to be compared across depth profiles generated at different times. The depth profile may also include information related to the illumination power at the time the image was taken. A power meter may also be referred to herein as a power sensor or a power monitor.

The method may allow for synchronized collection of a plurality of signals. The method may enable collection of a plurality of signals generated by a single excitation event. A depth profile can be generated using signals, as described elsewhere herein, that are generated from the same excitation event. A user may decide which signals to use to generate a depth profile.

The method may generate two or more layers of information. The two or more layers of information may be information generated from data generated from the same light pulse of the single probe system. The two or more layers may be from a same depth profile. Each of the two or more layers may also form separate depth profiles from which a projected cross section image may be created or displayed. For example, each separate layer, or each separate depth profile may correspond to a particular processed signals or signals that correspond to a particular imaging method. For example, a depth profile can be generated by taking two-photon fluorescence signals from melanin and another depth profile can be generated using SHG signals from collagen, and the two depth profiles can be overlaid as two layers of information. Each group of signals can be separately filtered, processed, and used to create individual depth profiles and projected cross section images, combined into a single depth profile with data that can be used to generate a projected cross section image, data from each group of signals can be combined and the combination can be used to generate a single depth profile, or any combination thereof. Each group of signals that correspond to a particular feature or features of the tissue can be assigned a color used to display the individual cross section images of the feature or features or a composite cross section image including data from each group of signals. The cross-sectional images or individual depth profiles can be overlaid to produce a composite image or depth profile. Thus, a multi-color, multi-layer, depth profile or image can be generated.

Example Images

FIGS. 7A-7D illustrate an example of images formed from depth profiles in skin. FIG. 7A illustrates an image displayed from a depth profile derived from a generated signal resulting from two-photon autofluorescence. The autofluorescence signal was generated from an excitation signal of about 780 nm and was collected into a light guide from a collection element at the tip of the optical probe. The autofluorescence signal was detected over a range of about 415 to 650 nm with an appropriately selected optical filter. The epidermis 703 can be seen along with the stratum corneum layer 701 at the surface of the skin. Elastin 702 at the boundary of epidermis 703 and dermis 705 layers can be seen as well as epithelial cells 708 (keratinocytes) in the epidermis 703 along with other features. FIG. 7B illustrates an image displayed from a depth profile or layer that is synchronized in time and location with the depth profile or layer of 7A. The image displayed from the depth profile in 7B is derived from a second harmonic generation signal at about 390 nm detected with an appropriately selected optical filter. The second harmonic generation signal was generated from an excitation signal of about 780 nm and was collected into a light guide from a collection element at the tip of the optical probe. Collagen 704 in the dermis layer 705 can be seen as well as other features. FIG. 7C illustrates an image displayed from a depth profile or layer that is synchronized in time and location with the depth profiles or layers of 7A and 7B. The image displayed from the depth profile in 7C is derived from a reflectance confocal signal reflected back to an RCM detector. The reflected signal of about 780 nm was directed back through its path of origin and split to an alignment arrangement that focused and aligned the reflected signal into an optical fiber for detection and processing. Melanocytes 707 and collagen 706 can be seen as well as other features. The images in FIGS. 7A, 7B and 7C can be derived from a single composite depth profile resulting from the excitation light pulses and having multiple layers or can be derived as single layers from separate depth profiles. FIG. 7D shows overlaid images of 7A- to 7C. The boundaries that can be identified from the features of FIGS. 7A and 7B can help identify the location of the melanocyte identified in FIG. 7D. Diagnostic information can be contained in the individual images and/or the composite or overlaid image of 7D. For example, it is believed that some suspected lesions can be identified based on the location and shape of the melanocytes or keratinocytes in the various tissue layers. The depth profiles of FIGS. 7A-7D may be examples of data for use in a machine learning algorithm as described elsewhere herein. For example, all three layers can be input into a machine learning classifier as individual layers, as well as using the composite image as another input.

Optical Techniques for Detecting Epithelial Cancers

The present disclosure provides optical techniques that may be used for diagnosing epithelial diseases and skin pathologies. Optical imaging techniques can display nuclear and cellular morphology and may offer the capability of real-time detection of tumors in large areas of freshly excised or biopsied tissue without the need for sample processing, such as that of histology. Optical imaging methods can also facilitate non-invasive, real-time visualization of suspicious tissue without excising, sectioning, and/or staining the tissue sample. Optical imaging may improve the yield of diagnosable tissue (e.g., by avoiding areas with fibrosis or necrosis), minimize unnecessary biopsies or endoscopic resections (e.g., by distinguishing neoplastic from inflammatory lesions), and assess surgical margins in real-time to confirm negative margins (e.g., for performing limited resections). The ability to assess a tissue sample in real-time, without needing to wait for tissue processing, sectioning, and staining, may improve diagnostic turnaround time, especially in time-sensitive contexts, such as during Mohs surgery. Non-limiting examples of optical imaging techniques for diagnosing epithelial diseases and cancers include multiphoton microscopy, autofluorescence microscopy, polarized light microscopy, confocal microscopy, Raman spectroscopy, optical coherence tomography, and ultrasonography. Non-limiting examples of detectable tissue components include keratin, NADPH, melanin, elastin, flavins, protoporphyrin ix, and collagen. Other detectable components can include tissue boundaries. For example, boundaries between stratum corneum, epidermis, and dermis are schematically illustrated in FIGS. 5A-5F. Example images from depth profiles shown in FIGS. 7A-7D show some detectable components, such as, for example, including but not limited to: tissue boundaries for stratum corneum, epidermis, and dermis, melanocytes, collagen, and elastin.

Multiphoton microscopy (MPM) can be used to image intrinsic molecular signals in living specimens, such as the skin tissue of a patient. In MPM, a sample may be illuminated with light at wavelengths longer than the normal excitation wavelength, for example twice as long or three times as long. MPM can include second harmonic generation microscopy (SHG) and third harmonic generation microscopy (THG). Third harmonic generation may be used to image nerve tissue.

Autofluorescence microscopy can be used to image biological molecules (e.g. fluorophores) that are inherently fluorescent. Non-limiting examples of endogenous biological molecules that are autofluorescent include nicotinamide adenine dinucleotide (NADH), NAD(P)H, flavin adenine dinucleotide (FAD), collagen, retinol, and tryptophan and the indoleamine derivatives of tryptophan. Changes in the fluorescence level of these fluorophores, such as with tumor progression, can be detected optically. Changes may be associated with altered cellular metabolic pathways (NADH, FAD) or altered structural tissue matrix (collagen).

Polarized light can be used to evaluate biological structures and examine parameters such as cell size and refractive index. Refractive index can provide information regarding the composition and organizational structure of cells, for example cells in a tissue sample. Cancer can significantly alter tissue organization, and these changes may be detected optically with polarized light.

Confocal microscopy may also be used to examine epithelial tissue. Exogenous contrast agents may be administered for enhanced visibility. Confocal microscopy can provide non-invasive images of nuclear and cellular morphology in about 2-5 μm thin sections in living human skin with lateral resolution of about 0.5-1.0 μm. Confocal microscopy can be used to visualize in vivo micro-anatomic structures, such as the epidermis, and individual cells, including melanocytes.

Raman spectroscopy may also be used to examine epithelial tissue. Raman spectroscopy may rely on the inelastic scattering (so-called "Raman" scattering) phenomena to detect spectral signatures of disease progression biomarkers such as lipids, proteins, and amino acids.

Optical coherence tomography may also be used to examine epithelial tissue. Optical coherence tomography may be based on interferometry in which a laser light beam is split with a beam splitter, sending some of the light to the sample and some of the light to a reference. The combination of reflected light from the sample and the reference can result in an interference pattern which can be used to determine a reflectivity profile providing information about the spatial dimensions and location of structures within the sample. Current, commercial optical coherence tomography systems have lateral resolutions of about 10 to 15 μm, with depth of imaging of about 1 mm or more. Although this technique can rapidly generate 3-dimensional (3D) image volumes that reflect different layers of tissue components (e.g., cells, connective tissue, etc), the image resolution (e.g., similar to the ×4 objective of a histology microscope) may not be sufficient for routine histopathologic diagnoses.

Ultrasound may also be used to examine epithelial tissue. Ultrasound can be used to assess relevant characteristics of epithelial cancer such as depth and vascularity. While ultrasonography may be limited in detecting pigments such as melanin, it can supplement histological analysis and provide additional detail to assist with treatment decisions. It may be used for noninvasive assessment of characteristics, such as thickness and blood flow, of the primary tumor and may contribute to the modification of critical management decisions.

Methods for diagnosing epithelial diseases and skin pathologies disclosed herein may comprise one or more of multiphoton microscopy, autofluorescence microscopy, polarized light microscopy, confocal microscopy, Raman spectroscopy, optical coherence tomography, and ultrasonography. In some cases, a method for diagnosing an epithelial disease and/or skin pathology comprises autofluorescence microscopy and multiphoton microscopy. As an alternative, a method for diagnosing an epithelial disease and/or skin pathology comprises autofluorescence microscopy, multiphoton microscopy, and polarized light microscopy. Both second harmonic generation microscopy and third harmonic generation microscopy can be used. In some cases, one of second harmonic generation microscopy and third harmonic generation microscopy is used.

Methods for diagnosing epithelial diseases and skin pathologies disclosed herein may comprise using one or more depth profiles to identify anatomical features and/or other tissue properties or characteristics and overlaying the images from the one or more depth profiles to an image from which a skin pathology can be identified.

Apparatuses for Generating Depth Profiles

Disclosed herein are apparatuses for generating depth profiles of tissues. In an aspect, an apparatus for generating a depth profile of a tissue of a subject may comprise an optical probe that transmits an excitation light beam from a light source towards a surface of the tissue, which excitation light beam, upon contacting the tissue, generate signals indicative of an intrinsic property of the tissue; one or more focusing units in the optical probe that simultaneously adjust a depth and a position of a focal point of the excitation light beam along a scan path, scan pattern or in one or more slant directions, one or more sensors configured to detect at least a subset of the signals generated upon contacting the tissue with the excitation light beam; and one or more computer processors operatively coupled to the one or more sensors, wherein the one or more computer processors are individually or collectively programmed to process the at least the subset of the signals detected by the one or more sensors to generate a depth profile of the tissue.

Figure 8:
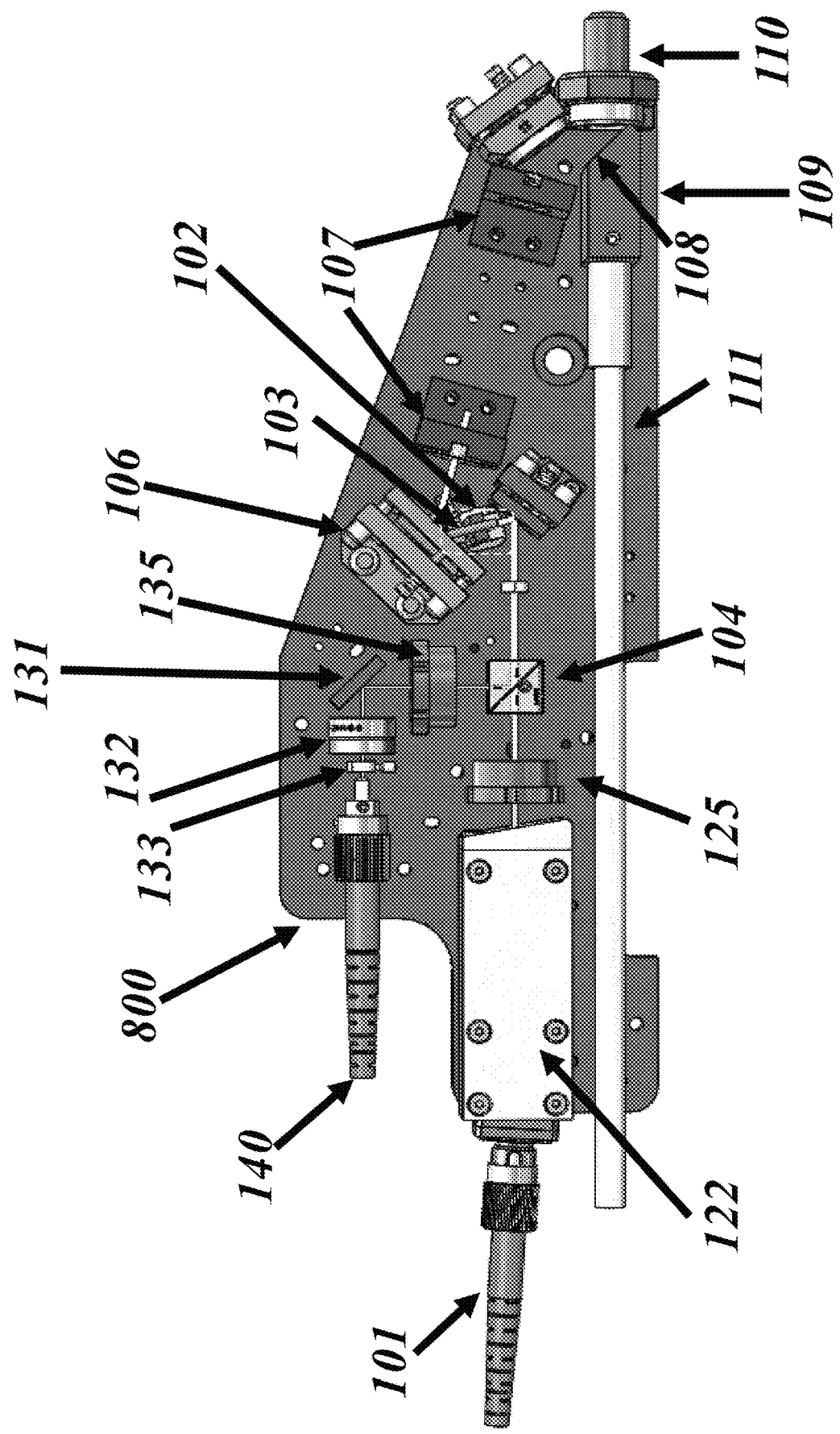
FIG. 8 shows example optical elements that may be within an optical probe housing.

FIG. 1 shows an example of focusing units configured to simultaneously adjust a depth and a position of a focal point of an excitation light beam. FIG. 1 shows examples of one or more focusing and scanning optics, i.e., focusing units of an optical probe that can be used for scanning and creating depth profiles of tissue. FIG. 8 shows examples of focusing and scanning components or units of the optical probe of FIG. 1 positioned in a handle 800. An afocal z-axis scanner 102 may comprise a moveable lens 103 and an actuator 105 (e.g., a voice coil) (FIG. 8) coupled to the moveable lens 103, and MEMS mirror 106. The afocal z-axis scanner 102 may converge or diverge the collimated beam of light, moving the focal point in the axial direction while imaging. Moving the focal point in the axial direction may enable imaging a depth profile. The MEMS mirror 106 can enable scanning by moving the focal point on a horizontal plane or an X-Y plane. According to some representative embodiments, the afocal Z-scanner 102 and the MEMS mirror 106 are separately actuated with actuators that are driven by a coordinated computer control so that their movements are synchronized to provide synchronized movement of focal points within tissue. According to some representative embodiments, moving both the moveable lens 103 and the MEMS mirror 106 may allow changing an angle between a focal plane and an optical axis, and enable imaging a depth profile through a plane (e.g., a slanted plane or focal plane as defined herein).

With continued reference to both FIG. 1 and FIG. 8, the optical probe may include a fiber optic 101 configured to transmit light from a laser to the optical probe. The fiber optic 101 may be a single mode fiber, a multi-mode fiber, or a bundle of fibers. The fiber optic 101 may be a bundle of fibers configured to transmit light from multiple lasers or light sources to the optical probe that are either pulsed or continuous beams. The fiber optic 101 may be coupled to a frequency multiplier 122 that converts the frequency to a predetermined excitation frequency (e.g., by multiplying the frequency by a factor of 1 or more). The frequency multiplier 122 may transmit light from fiber optic 101 to an optional polarizer 125 or polarization selective optical element. The light may be sent through a beam splitter 104 that directs a portion of the excitation light to a power monitor 120 and at least a portion of the returned reflected light to a light reflectance collection module 130. Other sensors may be included with the probe as well as a power monitor. The sensors and monitors may provide additional information concerning the probe or the subject that can be included as data with the depth profiles and can be used to further enhance machine learning.

The illumination light may be directed to the afocal z-axis scanner 102 and then through MEMS mirror 106. The MEMS mirror scanner may be configured to direct at least a part of the light through one or more relay lenses 107. The one or more relay lenses 107 may be configured to direct the light to a dichroic mirror 108. The dichroic mirror 108 may direct the excitation light into an objective 110. The objective 110 may be configured to direct the light to interact with a tissue of a subject. The objective 110 may be configured to collect one or more signals generated by the light interacting with the tissue of the subject. The generated signals may be either single-photon or multi-photon generated signals. A subset of the one or more signals may be transmitted through dichroic mirror 108 into a collection arrangement 109, and may be detected by one or more photodetectors as described herein, for example of detector block 1108 of FIG. 11B. The subset of the one or more signals may comprise multi-photon signals for example, that can include SHG and/or two-photon autofluorescence and/or two-photon fluorescence signals. The collection arrangement 109 may include optical elements (e.g., lenses and/or mirrors). The collection arrangement may direct the collected light through a light guide 111 to one or more photosensors. The light guide may be a liquid light guide, a multimode fiber, or a bundle of fibers.

Another subset of the one or more signals generated by light interacting with tissue and collected by the objective 110 may include single-photon signals. The subset of signals may be one or more RCM signals or single-photon fluorescence/autofluorescence signals. An RCM signal may trace a reverse path as the light that generated it. The reflected signal may be reflected by the beam splitter 104 towards an alignment arrangement that may align and focus the reflected signals or RCM signals onto an optical fiber 140. The alignment arrangement may comprise a focusing lens 132 and a refractive alignment element 133 with the refractive alignment element 133 positioned between the focusing lens 132 and optical fiber 140. The alignment arrangement may or may not comprise one or more additional optical elements such as one or more mirrors, lenses, and the like.

The reflected signal may be reflected by beam splitter 104 towards lens 132. The reflected signal may be directed to a focusing lens 132. The focusing lens 132 may be configured to focus the signal into optical fiber 140. The refractive alignment element 133 can be configured to align a focused beam of light from the focusing lens 132 into alignment with the fiber optic 140 for collection. According to some representative embodiments, the refractive alignment element 133 is moveably positioned between the focusing lens 132 and the optical fiber 140 while the focusing lens 132 and optical fiber 140 are fixed in their positions. The refractive element can be angularly or rotationally moveable with respect to the focusing lens and optical fiber. The refractive alignment element 133 may be a refractive element as described elsewhere herein. The optical fiber 140 may be a single mode fiber, a multimode fiber, or a bundle of fibers. The optical fiber 140 may be coupled to a photodetector for detecting the reflected signal.

An optional polarizer 135 or polarization selective optical element may be positioned between the beam splitter and the focusing lens. The polarizer may provide further anatomical detail from the reflected signal. A mirror 131 may be used to direct reflected signals from the beam splitter 104 to the alignment arrangement. The mirror 131 can be moveable and/or adjustable to provide larger alignment adjustments of the reflected signals before they enter the focusing lens 132. The mirror 131 can be positioned one focal length in front of the refractive alignment element 133. The mirror 131 may also be a beam splitter or may be polarized to split the reflected signal into elements with different polarizations to provide additional tissue detail from the reflected light. Once split, the split reflected signals can be directed through different alignment arrangements and through separate channels for processing.

The focusing lens 132 may focus the light of the RCM signal to a diffraction limited or nearly diffraction limited spot. The refractive alignment element 133 may be used to provide finer alignment of the light of the RCM signal to the fiber optic. The refractive alignment element can have a refractive index, a thickness, and/or a range of motion (e.g., a movement which alters the geometry) that permits alignment of the RCM signal exiting the lens to a fiber optic have a diameter less than about 20 microns, 10 microns, 5 microns, or less. According to some representative embodiments, the refractive alignment element properties (including refractive index, thickness, and range of motion) may be selected so that the aberrations introduced by the refractive alignment element do not increase the size the focused spot by greater than about 0%, 1%, 2%, 5%, 10%, 20%, or more above the focusing lens's diffraction limit. The optical fiber 140 may be coupled to a photodetector as described elsewhere herein. The photodetector may generate an image of a tissue. The refractive alignment element may enable RCM signal detection in a small form factor. The alignment arrangement can be contained within a handheld device.

The at least a subset of signals may comprise polarized light. The optical probe may comprise one or more polarization selective optics (e.g., polarization filters, polarization beam splitters, etc.). The one or more polarization selective optics may select for a particular polarization of RCM signal, such that the RCM signal that is detected is of a particular polarization from a particular portion of the tissue.

For example, polarization selective optics can be used to selectively image or amplify different features in tissue.

The at least a subset of signals may comprise unpolarized light. The optical probe may be configured to reject up to all out of focus light. By rejecting out of focus light, a low noise image may be generated from RCM signals.

Multiple refractive lenses, such as relay lenses, collimating lenses, and field lenses, may be used to focus the ultrafast pulses of light from a light source to a small spot within the tissue. The small spot of focused light can, upon contacting the tissue, generate endogenous tissue signals, such as second harmonic generation, 2-photon autofluorescence, third harmonic generation, coherent anti-stokes Raman spectroscopy, reflectance confocal microscopy signals, or other nonlinear multiphoton generated signals. The probe may also transfer the scanning pattern generated by optical elements such as mirrors and translating lenses to a movement of the focal spot within the tissue to scan the focus through the structures and generate a point by point image of the tissue. The probe may comprise multiple lenses to minimize aberrations, optimize the linear mapping of the focal scanning, and maximize resolution and field of view.

The one or more focusing units in the optical probe may comprise, but are not limited to, movable lens, an actuator coupled to an optical element (e.g., an afocal lens), MEMS mirror, relay lenses, dichroic mirror, a fold mirror, a beam splitter, and/or an alignment arrangement. An alignment element may comprise but is not limited to a focusing lens, polarizing lens, refractive element, adjustment element for a refractive element, an angular adjustment element, and/or a moveable mirror. The signals indicative of an intrinsic property of the tissue may be signals as described elsewhere herein, such as, for example, second harmonic generation signals, multi photon fluorescence signals, reflectance confocal microscopy signals, other generated signals, or any combination thereof.

Apparatuses consistent with the methods herein may comprise any element of the subject methods including, but not limited to, an optical probe; one or more light sources such as an ultrashort pulse laser; one or more mobile or tunable lenses; one or more optical filters; one or more photodetectors; one or more computer processors; one or more marking tools; and combinations thereof.

The photodetector may comprise, but are not limited to, a photomultiplier tube (PMT), a photodiode, an avalanche photodiode (APD), a charge-coupled device (CCD) detector, a charge-injection device (CID) detector, a complementary-metal-oxide-semiconductor detector (CMOS) detector, a multi-pixel photon counter (MPPC), a silicon photomultiplier (SiPM), light dependent resistors (LDR), a hybrid PMT/avalanche photodiode sensor, and/or other detectors or sensors. The system may comprise one or more photodetectors of one or more types, and each sensor may be used to detect the same or different signals. For example, a system can use both a photodiode and a CCD detector, where the photodiode detects SHG and multi photon fluorescence and the CCD detects reflectance confocal microscopy signals. The photodetector may be operated to provide a framerate, or number of images taken per second, of at least about 0.5, 1, 2, 3, 4, 5, 6, 7, 8, 9, 10, 15, 20, 24, or more. The photodetector may be operated to provide a framerate of at most about 60, 50, 40, 30, 24, 20, 15, 10, 9, 8, 7, 6, 5, 4, 3, 2, 1, 0.5, or less.

The optical probe may comprise a photomultiplier tube (PMT) that collects the signals. The PMT may comprise electrical interlocks and/or shutters. The electrical interlocks and/or shutters can protect the PMT when the photomultiplier compartment is exposed to ambient light by activating when contact between the surface of the epithelial tissue and the optical prove has been disrupted. By using activatable interlocks and/or shutters, signals can be collected in the presence of ambient light, thereby allowing a user to generate one or more real-time, pre-surgical depth profiles at the bedside of the patient. The optical probe may comprise other photodetectors as well The light source providing ultrashort pulses of light can be a wavelength-tunable, ultrashort-pulsed Ti:Sapphire laser. A Ti:Sapphire laser can be a mode-locked oscillator, a chirped-pulse amplifier, or a tunable continuous wave laser. A mode-locked oscillator can generate ultrashort pulses with a duration between about a few picoseconds and about 10 femtoseconds, and in cases about 5 femtoseconds. The pulse repetition frequency can be about 70 to 90 megahertz (MHz). The term 'chirped-pulse' generally refers to a special construction that can prevent the pulse from damaging the components in the laser. In a 'chirped-pulse' laser, the pulse can be stretched in time so that the energy is not all located at the same point in time and space, preventing damage to the optics in the amplifier. The pulse can then be optically amplified and recompressed in time to form a short, localized pulse.

The mobile lens or moveable lens of an apparatus can be translated to yield the plurality of different scan patterns or scan paths. The mobile lens may be coupled to an actuator that translates the lens. The actuator may be controlled by a programmed computer processor. The actuator can be a linear actuator, such as a mechanical actuator, a hydraulic actuator, a pneumatic actuator, a piezoelectric actuator, an electro-mechanical actuator, a linear motor, a linear electric actuator, a voice coil, or combinations thereof. Mechanical actuators can operate by converting rotary motion into linear motion, for example by a screw mechanism, a wheel and axle mechanism, and a cam mechanism. A hydraulic actuator can involve a hollow cylinder comprising a piston and an incompressible liquid. A pneumatic actuator may be similar to a hydraulic actuator but involves a compressed gas instead of a liquid. A piezoelectric actuator can comprise a material which can expand under the application of voltage. As a result, piezoelectric actuators can achieve extremely fine positioning resolution, but may also have a very short range of motion. In some cases, piezoelectric materials can exhibit hysteresis which may make it difficult to control their expansion in a repeatable manner. Electro-mechanical actuators may be similar to mechanical actuators. However, the control knob or handle of the mechanical actuator may be replaced with an electric motor.

Tunable lenses can refer to optical elements whose optical characteristics, such as focal length and/or location of the optical axis, can be adjusted during use, for example by electronic control. Electrically-tunable lenses may contain a thin layer of a suitable electro-optical material (e.g., a material whose local effective index of refraction, or refractive index, changes as a function of the voltage applied across the material). An electrode or array of electrodes can be used to apply voltages to locally adjust the refractive index to the value. The electro-optical material may comprise liquid crystals. Voltage can be applied to modulate the axis of birefringence and the effective refractive index of an electro-optical material comprising liquid crystals. In some cases, polymer gels can be used. A tunable lens may comprise an electrode array that defines a grid of pixels in the liquid crystal, similar to pixel grids used in liquid-crystal displays. The refractive indices of the individual pixels may be electrically controlled to give a phase modulation profile.

The phase modulation profile may refer to the distribution of the local phase shifts that are applied to light passing through the layer as the result of the locally-variable effective refractive index over the area of the electro-optical layer of the tunable lens.

In some cases, an electrically or electro-mechanically tunable lens that is in electrical or electro-mechanical communication with the optical probe may be used to yield the plurality of different scan patterns or scan paths. Modulating a curvature of the electrically or electro-mechanically tunable lens can yield a plurality of different scan patterns or scan paths with respect to the epithelial tissue. The curvature of the tunable lens may be modulated by applying current. The apparatus may also comprise a programmed computer processor to control the application of current.

An apparatus for identifying a disease in an epithelial tissue of a subject may comprise an optical probe. The optical probe may transmit an excitation light beam from a light source towards a surface of the epithelial tissue. The excitation light beam, upon contacting the epithelial tissue, can then generate signals that relate to an intrinsic property of the epithelial tissue. The light source may comprise an ultra-fast pulse laser, such as a Ti:Sapphire laser. The ultra-fast pulse laser may generate pulse durations less than 500 femtoseconds, 400 femtoseconds, 300 femtoseconds, 200 femtoseconds, 100 femtoseconds, or less. The pulse repetition frequency of the ultrashort light pulses can be at least 10 MHz, 20 MHz, 30 MHz, 40 MHz, 50 MHz, 60 MHz, 70 MHz, 80 MHz, 90 MHz, 100 MHz, or greater.

The tissue may be epithelial tissue. The depth profile may permit identification of the disease in the epithelial tissue of the subject. The disease in the tissue of the subject is disclosed elsewhere herein.

The scanning path or pattern may be in one or more slant directions and on one or more slanted planes. A slanted plane may be positioned along a direction that is angled with respect to an optical axis of the optical probe. The angle between a slanted plane and the optical axis may be at most 45°. The angle between a slanted plane and the optical axis may be at least about 5°, 10°, 15°, 20°, 25°, 30°, 35°, 40°, 45°, 55°, 60°, 65°, 70°, 75°, 80°, 85°, or greater. In other cases, the angle between a slanted plane and the optical axis may be at most about 85°, 80°, 75°, 70°, 65°, 60°, 55°, 50°, 45°, 35°, 30°, 25°, 20°, 15°, 10°, 5°, or less.

The optical probe may further comprise one or more optical filters, which one or more optical filters may be configured to collect a subset of the signals. Optical filters, as described elsewhere herein, can be used to collect one or more specific subsets of signals that relate to one or more intrinsic properties of the epithelial tissue. The optical filters may be a beam splitter, a polarizing beam splitter, a notch filter, a dichroic filter, a long pass filter, a short pass filter, a bandpass filter, or a response flattening filter. The optical filters may be one or more optical filters. These optical filters can be coated glass or plastic elements which can selectively transmit certain wavelengths of light, such as autofluorescent wavelengths, and/or light with other specific attributes, such as polarized light. The optical filters can collect at least one signal selected from the group consisting of second harmonic generation (SHG) signal, third harmonic generation (THG) signal, polarized light signal, reflectance confocal microscopy (RCM) signal, and autofluorescence signal. The subset of the signals may include at least one of second harmonic generation (SHG) signals, third harmonic generation (THG) signals, and autofluorescence signals.

The light source may comprise an ultra-fast pulse laser with pulse durations less than about 200 femtoseconds. An ultra-fast pulse laser may produce pulses of light with pulse durations at most 500 femtoseconds, 450 femtoseconds, 400 femtoseconds, 350 femtoseconds, 300 femtoseconds, 250 femtoseconds, 200 femtoseconds, 150 femtoseconds, 100 femtoseconds, or shorter. In some cases, the pulse duration is about 150 femtoseconds. In some cases, an ultra-fast pulse laser may produce pulses of light with pulse durations at least 100 femtoseconds, 150 femtoseconds, 200 femtoseconds, 250 femtoseconds, 300 femtoseconds, 350 femtoseconds, 400 femtoseconds, 450 femtoseconds, 500 femtoseconds, or shorter. The pulse repetition frequency of an ultra-fast pulse laser can be at least 10 MHz, 20 MHz, 30 MHz, 40 MHz, 50 MHz, 60 MHz, 70 MHz, 80 MHz, 90 MHz, 100 MHz, or greater. In some cases, the pulse repetition frequency of an ultra-fast pulse laser can be at most 100 MHz, 90 MHz, 80 MHz, 70 MHz, 60 MHz, 50 MHz, 40 MHz, 30 MHz, 20 MHz, 10 MHz, or less. In some cases, the pulse repetition frequency is about 80 MHz.

During use, the optical probe may be in contact with the surface of the tissue. The contact may be direct or indirect contact. If the contact is a direct contact, performing the contact may comprise placing the optical probe next to the tissue of the subject without an intervening layer. If the contact is an indirect contact, performing the contact may comprise placing the optical probe next to the tissue of the subject with one or more intervening layers. The one or more intervening layers may comprise, but are not limited to, clothes, medical gauzes, bandages, and so forth. The contact may be monitored such that when contact between the surface of the epithelial tissue and the optical probe is disrupted, a shutter positioned in front of the detector (e.g., relative to the path of light) can be activated and block incoming light. In some cases, the photodetector comprises electrical interlocks and/or shutters. The electrical interlocks and/or shutters can protect the photodetector when the photomultiplier compartment is exposed to ambient light by activating when contact between the surface of the epithelial tissue and the optical prove has been disrupted. By using activatable interlocks and/or shutters, signals can be collected in the presence of ambient light, thereby allowing a user to generate one or more real-time, pre-surgical depth profiles at the bedside of the patient.

The apparatus may comprise a sensor that detects a displacement between the optical probe and the surface of the tissue. This sensor can protect the photodetector, for example a photodetector, from ambient light by activating a shutter or temporarily deactivating the photodetector to prevent ambient light from reaching and damaging the photodetector, if the ambient light exceeds the detection capacity of the photodetector.

The optical probe may comprise a power meter. The power meter may be optically coupled to the light source. The power meter may be used to correct for fluctuations of the power of the light source. The power meter may be used to control the power of the light source. For example, an integrated power meter can allow for setting a power of the light source depending on how much power is needed for a particular imaging session. The power meter may ensure a consistent illumination over a period of time, such that images taken throughout the period of time have similar illumination conditions. The power meter may provide information regarding the power of the illumination light to the system processing that can be recorded with the depth profile. The power information can be included in the machine learning described elsewhere herein. The power meter may be, for example, a photodiode, a pyroelectric power meter, or a thermal power meter. The power meter may be a plurality of power meters.

The apparatus may further comprise a marking tool for outlining a boundary that is indicative of a location of the disease in the epithelial tissue of the subject. The marking tool can be a pen or other writing instrument comprising skin marking ink that is FDA approved, such as Genetian Violet Ink; prep resistant ink that can be used with aggressive skin prep such as for example CHG/isopropyl alcohol treatment; waterproof permanent ink; or ink that is easily removable such as with an alcohol. A pen can have a fine tip, an ultra-fine tip, or a broad tip. The marking tool can be a sterile pen. As an alternative, the marking tool may be a non-sterile pen.

The apparatus may be a portable apparatus. The portable apparatus may be powered by a battery. The portable apparatus may comprise wheels. The portable apparatus may be contained within a housing. The housing can have a footprint of greater than or equal to about 0.1 $ft^2$, 0.2 $ft^2$, 0.3 $ft^2$, 0.4 $ft^2$, 0.5 $ft^2$, 1 $ft^2$, or more. As an alternative, the housing can have a footprint that is less than or equal to about 1 $ft^2$, 0.5 $ft^2$, 0.4 $ft^2$, 0.3 $ft^2$, 0.2 $ft^2$, or 0.1 $ft^2$. The portable apparatus may comprise a filtered light source that emits light within a range of wavelengths not detectable by the optical probe.

The portable apparatus may be at most 50 lbs, 45 lbs, 40 lbs, 35 lbs, 30 lbs, 25 lbs, 20 lbs, 15 lbs, 10 lbs, 5 lbs or less. In some cases, the portable apparatus may be at least 5 lbs, 10 lbs, 15 lbs, 20 lbs, 25 lbs, 30 lbs, 35 lbs, 40 lbs, 45 lbs, 50 lbs, 55 lbs or more.

The optical probe may comprise a handheld housing configured to interface with a hand of a user. An optical probe that can be translated may comprise a handheld and portable housing. This can allow a surgeon, physician, nurse, or other healthcare practitioner to examine in real-time the location of the disease, for example a cancer in skin tissue, at the bedside of a patient. The portable apparatus can have a footprint of greater than or equal to about 0.1 $ft^2$, 0.2 $ft^2$, 0.3 $ft^2$, 0.4 $ft^2$, 0.5 $ft^2$, or 1 $ft^2$. As an alternative, the portable apparatus can have a footprint that is less than or equal to about 1 $ft^2$, 0.5 $ft^2$, 0.4 $ft^2$, 0.3 $ft^2$, 0.2 $ft^2$, or 0.1 $ft^2$.

The probe may have a tip diameter that is less than about 10 millimeters (mm), 8 mm, 6 mm, 4 mm, or 2 mm. The handheld device may have a mechanism to allow for the disposable probe to be easily connected and disconnected. The mechanism may have an aligning function to enable precise optical alignment between the probe and the handheld device. The handheld device may be shaped like an otoscope or a dermatoscope with a gun-like form factor. The handheld device may have a weight of at most about 8 pounds (lbs), 4 lbs, 2 lb, 1 lbs, 0.5 lbs, or 0.25 lbs. A screen may be incorporated into the handheld device to give point-of-care viewing. The screen may be detachable and able to change orientation. The handheld device may be attached to a portable system which may include a rolling cart or a briefcase-type configuration. The portable device may comprise a screen. The portable device may comprise a laptop computing device, a tablet computing device, a computing device coupled to an external screen (e.g., a desktop computer with a monitor), or a combination thereof. The portable system may include the laser, electronics, light sensors, and power system. The laser may provide light at an optimal frequency for delivery. The handheld device may include a second harmonic frequency doubler to convert the light from a frequency useful for delivery (e.g., 1,560 nm) to one useful for imaging tissue (e.g., 780 nm). For example, the delivery frequency may be at least about 800 nm, 900 nm, 1,000 nm, 1,100 nm, 1,200 nm, 1,300 nm, 1,400 nm, 1,500 nm, 1,600 nm, 1,700 nm, 1,800 nm, 1,900 nm, or more and the imaging frequency may be at least about 400 nm, 450 nm, 500 nm, 550 nm, 600 nm, 650 nm, 700 nm, 750 nm, 800 nm, 850 nm, 900 nm, 950 nm or more. The laser may be of low enough power to run the system on battery power. The system may further comprise a charging dock or ministand to hold the portable unit during operation. There may be many mini-stands in a single medical office and a singly portable system capable of being transported between rooms.

The housing may further comprise an image sensor. Alternatively, the image sensor may be located outside of the housing. In either case, the image sensor may be configured to locate the optical probe housing in space. The image sensor may locate the optical probe housing in space by tracking one or more features around the optical probe. The image sensor may be a video camera. The one or more features may be features of the tissue (e.g., freckles, birthmarks, etc.). The one or more features may be features of the space wherein the optical probe is used (e.g., furniture, walls, etc.). For example, the housing can have a number of cameras integrated into it that use a computer algorithm to track the position of the housing by tracking the movement of the furniture of the room the optical probe is being used in, and the tracking can be used to help generate a complete 3D image of a section of a tissue. By simultaneously tracking the position of the housing while recording images of tissue, a computer can reconstruct the location of the image within the tissue as the housing translates. In this way a larger mosaic region of the tissue can be imaged and digitally reconstructed. Such a region can be a 3D volume, or a 2D mosaic, or an arbitrary surface within the tissue. The image sensor may be configured to detect light in the near infrared. The housing may be configured to project a plurality of points to generate a map for the image sensor to use for tracking.

The housing may contain optical elements configured to direct the at least a subset of the signals to one or more detectors. The one or more detectors may be optically coupled to the housing via one or more fiber optics. The housing may contain the one or more detectors as well as a light source, thus having an entirely handheld imaging system.

Figure 10:
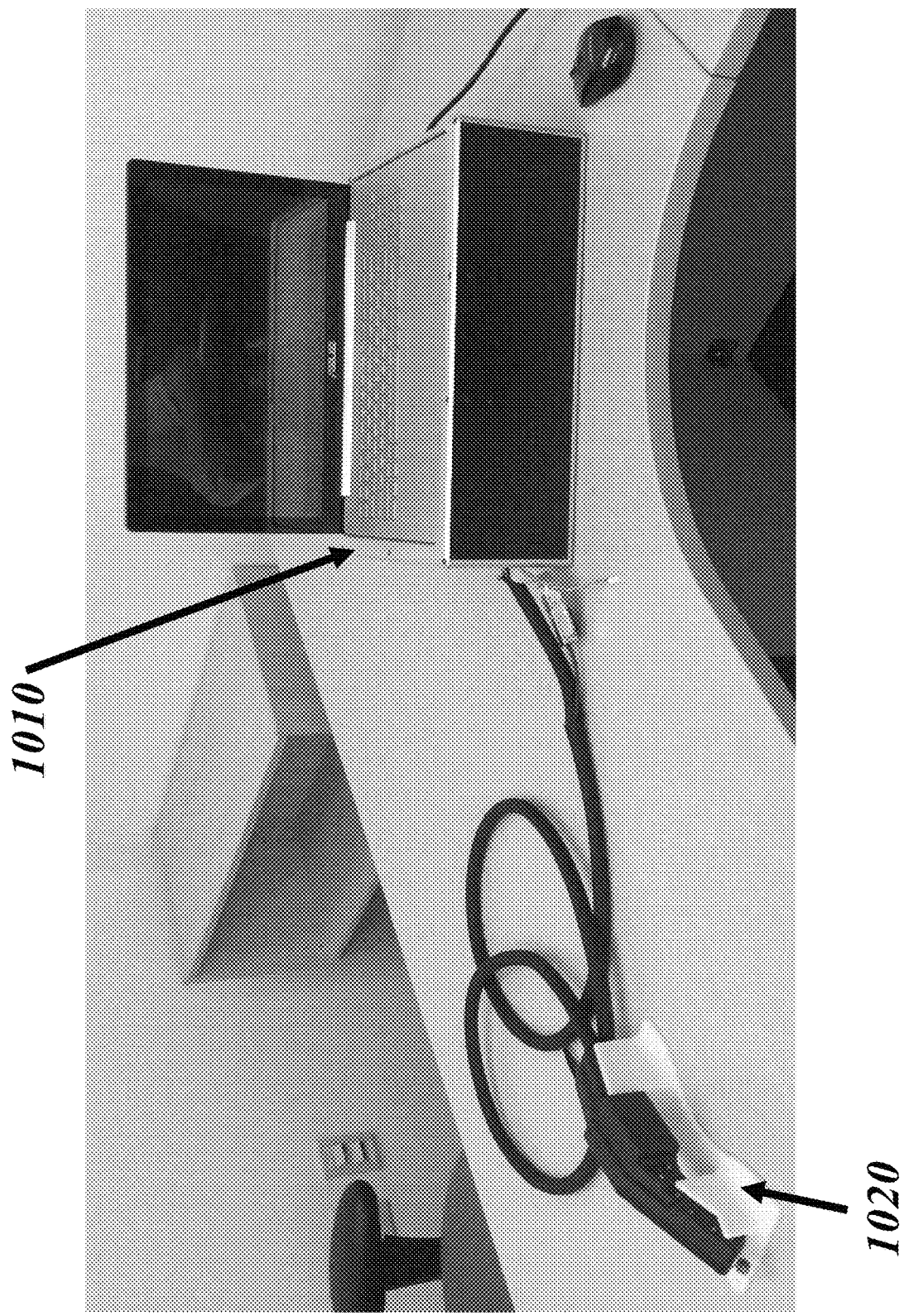
FIG. 10 shows an example housing coupled to a support system.
Figure 11A:
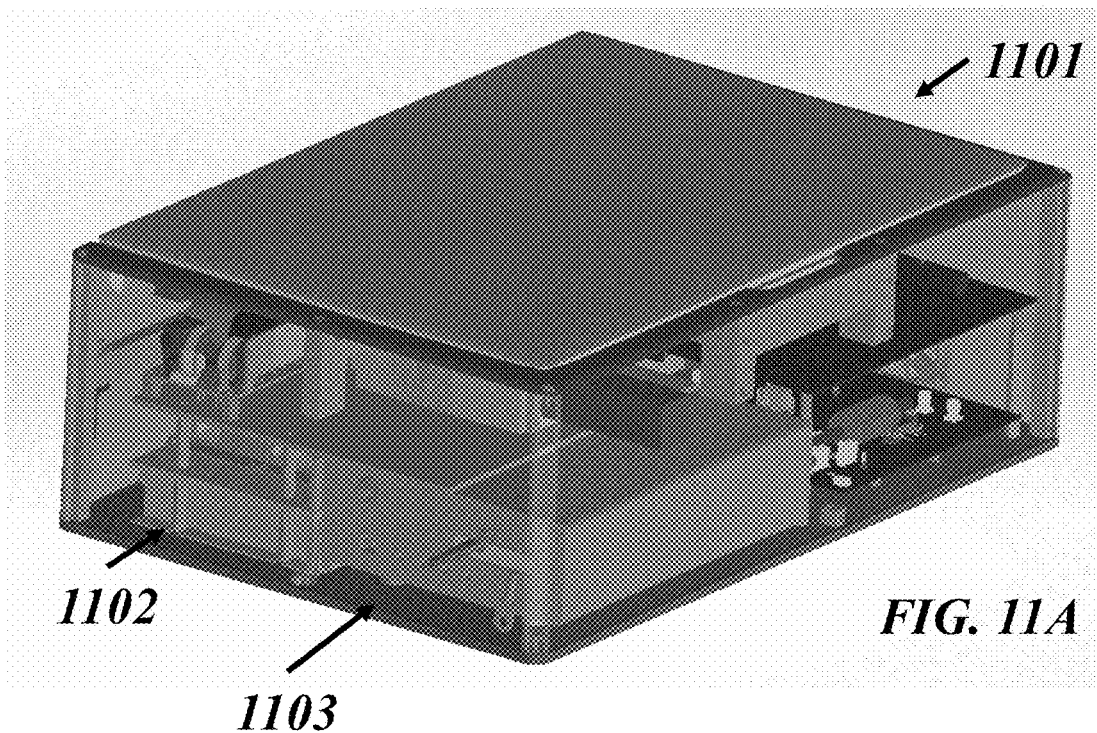
FIGS. 11A-11B shows an example support system.
Figure 11B:
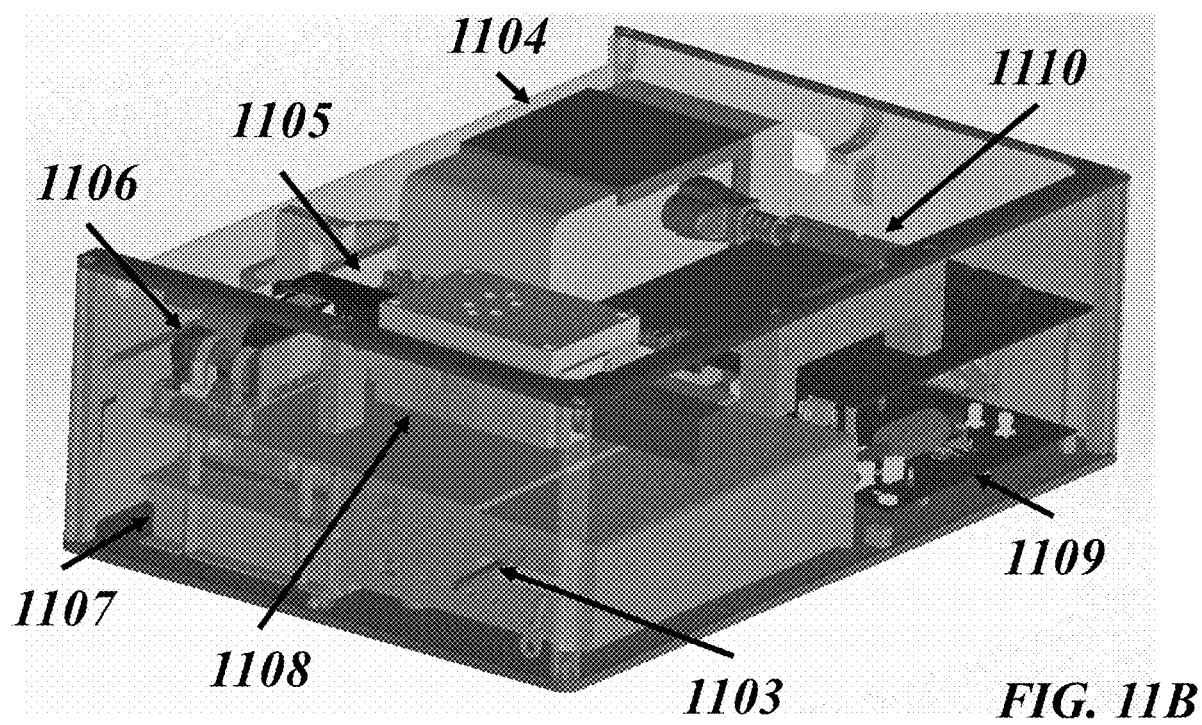

FIG. 10 shows an example of a probe housing 1020 coupled to a support system 1010. FIGS. 11A and 11B show the inside of an example support system 1010. A portable computing device 1101 may be placed on top of the support system 1010. The support system may comprise a laser 1103. The support system 1010 may comprise a plurality of support electronics, such as, for example, a battery 1104, a controller 1102 for the afocal lens actuator a MEMS mirror driver 1105, a power supply 1106, one or more transimpedance amplifiers 1107, a photodetector block 1108, a plurality of operating electronics 1109, a data acquisition board 1110, other sensors or sensor blocks or any combination thereof.

Figure 12:
FIG. 12 shows an example of the portability of the example housing coupled to a support system.
Figure 13:
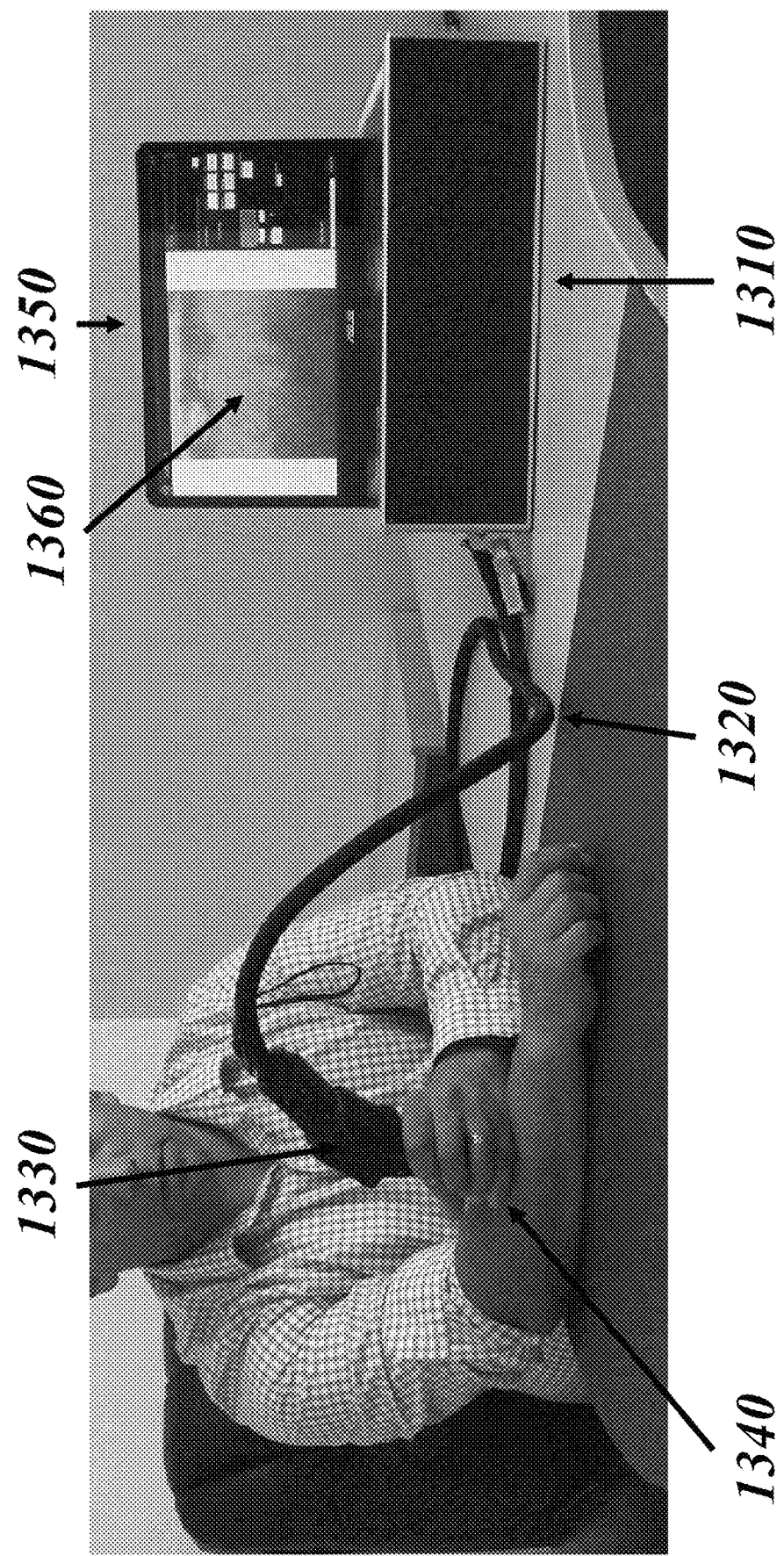
FIG. 13 shows an example system in use.
Figure 14A:
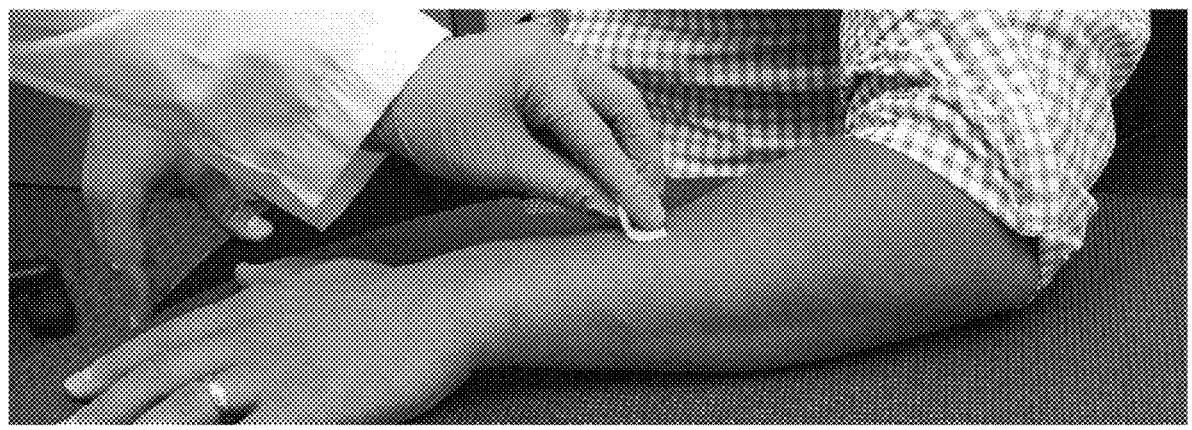
FIGS. 14A-14B shows an example of preparation of a subject for imaging.
Figure 14B:
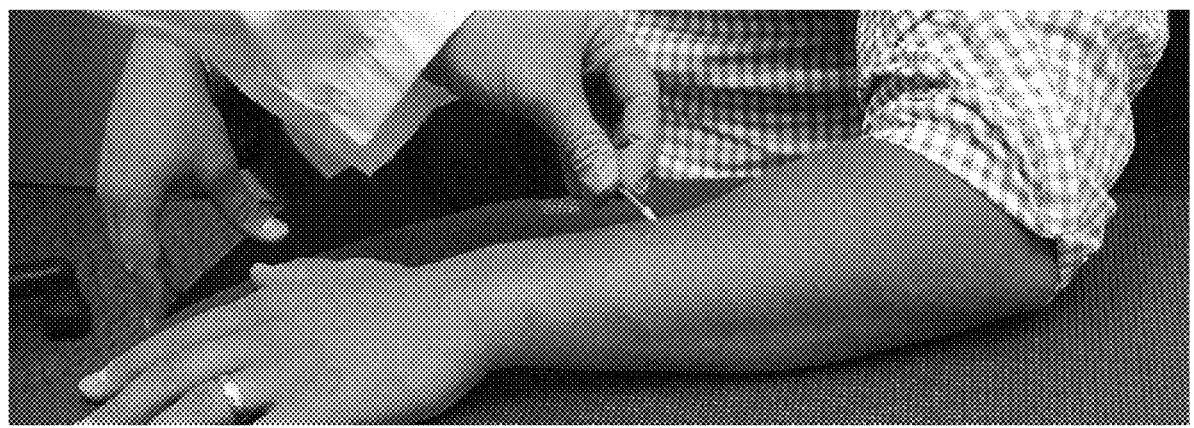

FIG. 12 shows an example of the portability of the example of FIG. 10. FIG. 13 shows an example system in use. Support system 1310 may send a plurality of optical pulses to housing 1330 via connecting cable 1320. The plurality of optical pulses may interact with tissue 1340 generating a plurality of signals. The plurality of signals may travel along the connecting cable 1320 back to the support system 1310. The support system 1310 may comprise a portable computer 1350. The portable computer may process the signals to generate and display an image 1360 that can be formed from a depth profile and collected signals as described herein. FIGS. 14A and 14B show an example of preparation of a subject for imaging. FIG. 14A shows how an alcohol swab may be used to clean a tissue of a subject for imaging. FIG. 14B shows how a drop of glycerol may be applied to a tissue of a subject. Imaging may be performed in the absence of hair removal, stains, drugs, or immobilization.

The one or more computer processors may be operatively coupled to the one or more sensors. The one or more sensors may comprise an infrared sensor, optical sensor, microwave sensor, ultrasonic sensor, radio-frequency sensors, magnetic sensor, vibration sensor, acceleration sensor, gyroscopic sensor, tilt sensor, piezoelectric sensor, pressure sensor, strain sensor, flex sensor, electromyographic sensor, electrocardiographic sensor, electroencephalographic sensor, thermal sensor, capacitive touch sensor, or resistive touch sensor.

Methods for Classifying Images of Tissue of a Subject/ Identifying a Disease

Disclosed herein are methods for generating a trained algorithm for classifying images of tissues from a subject. Classifying images of tissues may aid in identifying a disease in a tissue of a subject or in assessing or analyzing other features of the tissue in a subject pertaining to the health, function, treatment, or appearance of said tissues. In an aspect, a method for generating a trained algorithm for identifying a disease in a tissue of a subject may comprise (a) collecting signals from training tissues of subjects that have been previously or subsequently identified as having the disease, which signals are selected from the group consisting of second harmonic generation signal, third harmonic generation signal, reflectance confocal microscopy signal, autofluorescence signal, and other generated signals as defined herein; (b) processing the signals to generate data corresponding to depth profiles of the training tissues of the subjects; and (c) using the data from (b) to train a machine learning algorithm to yield a trained algorithm in computer memory for identifying the disease in the tissue of the subject wherein the tissue is independent of the training tissues. Collecting the signals from training tissues of subjects in operation (a) above may comprise collecting signals from the training tissues of subjects to generate one or more depth profiles using signals that are synchronized in time and location. Such depth profiles, for example, may be generated using the optical probe as described elsewhere herein. Such depth profiles can comprise individual components, images or depth profiles created from a plurality of subsets of gathered and processed generated signals. The depth profile may comprise a plurality of layers created from a plurality of subsets of images collected from the same location and time. Each of the plurality of layers may comprise data that identifies different anatomical structures and/or characteristics than those of the other layer(s). Such depth profiles may comprise a plurality of sub-set depth profiles. Each of the subset of depth profiles may be individually trained and/or a composite depth profile of subset depth profiles may be trained. The subset of signals that form a subset of layers or depth profiles may comprise second harmonic generation signal, third harmonic generation signal, autofluorescence signal, RCM signals, other generated signals, and/or subsets or split sets of any of the foregoing as described elsewhere herein. A plurality of depths profiles can be generated in the training tissues of the subject by translating the optical probe. A portion of the plurality of depth profiles can be generated in a region of the training tissue with the suspected disease while a portion of the depth profiles can be generated outside of said region. For example, a portion of the plurality of depth profiles generated outside of the region may be used to collect subject control data. A method for generating a trained algorithm for identifying and classifying features of the tissue in a subject pertaining to the health, function, treatment, or appearance of said tissues can proceed in a similar manner by collecting signals from training tissues of subjects that have been previously or subsequently identified as having the respective features. The respective features can include features used to identify disease and/or disfunction in tissue and/or to assess health, function or appearance of skin or tissue.

The signals may be substantially simultaneously (e.g., signals generated within a time period less than or equal to about 30 seconds (s), 20 s, 10 s, 1 s, 0.5 s, 0.4 s, 0.3 s, 0.2 s, 0.1 s, 0.01 s, 0.005 s, 0.001 s, or less; signals generated by the same pulse or beam of light, etc.) generated within a single region of the tissue (e.g., signals generated within less than or equal to about 1, 1E-1, 1E-2, 1E-3, 1E-4, 1E-5, 1E-6, 1E-7, 1E-8, 1E-9, 1E-10, 1E-11, 1E-12, 1E-13 or less cubic centimeters). The signals may be generated by the same pulse or beam of light. The signals may be generated by multiple beams of light synchronized in time and location as described elsewhere herein. Two or more of the signals may be combined to generate a composite image. The signals or subset of signals may be generated within a single region of the tissue using the same or similar scanning pattern or scanning plane. Each signal of a plurality of signals may be independent from the other signals of the plurality of signals. A user can decide which subset(s) of signals to use. For example, when both RCM and SHG signals are collected in a scan, a user can decide whether to use only the RCM signals. The substantially simultaneous generation of the signals may make the signals ideal signals for use with a trained algorithm. Additionally, video tracking of the housing position as described previously herein can be recorded simultaneously with the generated signals.

The optical data may comprise structured data, time-series data, unstructured data, relational data, or any combination thereof. Unstructured data may comprise text, audio data, image data and/or video. Time-series data may comprise data from one or more of a smart meters, a smart appliance, a smart device, a monitoring system, a telemetry device, or a sensor. Relational data may comprise data from one or more of a customer system, an enterprise system, an operational system, a website, or web accessible application program interface (API). This may be done by a user through any method of inputting files or other data formats into software or systems.

The data can be stored in a database. A database can be stored in computer readable format. A computer processor may be configured to access the data stored in the computer readable memory. A computer system may be used to analyze the data to obtain a result. The result may be stored remotely or internally on storage medium and communicated to personnel such as medication professionals. The computer system may be operatively coupled with components for transmitting the result. Components for transmitting can include wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples or wireless communication components can include a Wi-Fi receiver, a component for accessing a mobile data standard such as a 3G or 4G LTE data signal, or a Bluetooth receiver. All these data in the storage medium may be collected and archived to build a data warehouse.

The database may comprise an external database. The external database may be a medical database, for example, but not limited to, Adverse Drug Effects Database, AHFS Supplemental File, Allergen Picklist File, Average WAC Pricing File, Brand Probability File, Canadian Drug File v2, Comprehensive Price History, Controlled Substances File, Drug Allergy Cross-Reference File, Drug Application File, Drug Dosing & Administration Database, Drug Image Database v2.0/Drug Imprint Database v2.0, Drug Inactive Date File, Drug Indications Database, Drug Lab Conflict Database, Drug Therapy Monitoring System (DTMS) v2.2/DTMS Consumer Monographs, Duplicate Therapy Database, Federal Government Pricing File, Healthcare Common Procedure Coding System Codes (HCPCS) Database, ICD-10 Mapping Files, Immunization Cross-Reference File, Integrated A to Z Drug Facts Module, Integrated Patient Education, Master Parameters Database, Medi-Span Electronic Drug File (MED-File) v2, Medicaid Rebate File, Medicare Plans File, Medical Condition Picklist File, Medical Conditions Master Database, Medication Order Management Database (MOMD), Parameters to Monitor Database, Patient Safety Programs File, Payment Allowance Limit-Part B (PAL-B) v2.0, Precautions Database, RxNorm Cross-Reference File, Standard Drug Identifiers Database, Substitution Groups File, Supplemental Names File, Uniform System of Classification Cross-Reference File, or Warning Label Database.

The optical data may also be obtained through data sources other than the optical probe. The data sources may include sensors or smart devices, such as appliances, smart meters, wearables, monitoring systems, video or camera systems, data stores, customer systems, billing systems, financial systems, crowd source data, weather data, social networks, or any other sensor, enterprise system or data store. Example of smart meters or sensors may include meters or sensors located at a customer site, or meters or sensors located between customers and a generation or source location. By incorporating data from a broad array of sources, the system may be capable of performing complex and detailed analyses. The data sources may include sensors or databases for other medical platforms without limitation.

The optical probe may transmit an excitation light beam from a light source towards a surface of a reference tissue, which excitation light beam, upon contacting the tissue, generate the optical data of the tissue. The optical probe may comprise one or more focusing units to simultaneously adjust a depth and a position of a focal point of the excitation light beam along a scan path or scan pattern. The one or more focusing units in the optical probe may comprise, but are not limited to, movable lens, voice coil coupled to an optical element (e.g., an afocal lens), MEMS mirror, relay lenses, dichroic mirror, and fold mirror.

The scan path or scan pattern may comprise a path or pattern in at least one slant direction ("slanted path" or "slanted pattern"). The at least one slanted path or slanted pattern may be angled with respect to an optical axis. The angle between a slanted path or slanted pattern and the optical axis may be at most 45°. The angle between a slanted path or slanted pattern and the optical axis may be at least about 5°, 10°, 15°, 20°, 25°, 30°, 35°, 40°, 45°, 55°, 60°, 65°, 70°, 75°, 80°, 85°, or greater. In other cases, the angle between the slanted path or slanted pattern and the optical axis may be at most about 85°, 80°, 75°, 70°, 65°, 60°, 55°, 50°, 45°, 35°, 30°, 25°, 20°, 15°, 10°, 5°, or less.

The scan path or scan pattern may form a focal plane and/or may form or lie on at least one slanted plane. The at least one slanted plane may be positioned along a direction that is angled with respect to an optical axis. The angle between a slanted plane and the optical axis may be at most 45°. The angle between a slanted plane and the optical axis may be at least about 5°, 10°, 15°, 20°, 25°, 30°, 35°, 40°, 45°, 55°, 60°, 65°, 70°, 75°, 80°, 85°, or greater. In other cases, the angle between the slanted plane and the optical axis may be at most about 85°, 80°, 75°, 70°, 65°, 60°, 55°, 50°, 45°, 35°, 30°, 25°, 20°, 15°, 10°, 5°, or less.

The disease may be epithelial cancer.

The method may further comprise receiving medical data of the subject. The medical data of the subject may be obtained from a data receiver. The data receiver may be configured to either retrieve or receive data from one or more data sources, wherein retrieving data comprises a data extraction process and receiving data comprises receiving transmitted data from an electronic source of data. The medical data of the subject may comprise a physical condition, medical history, current and past occupations, age, sex, race, Fitzpatrick skin type, other metrics for skin health and appearance, and nationality of the subject. The physical conditions of the subject may be obtained through one or more medical instruments. The one or more medical instruments may include, but not limited to, stethoscope, suction device, thermometer, tongue depressor, transfusion kit, tuning fork, ventilator, watch, stopwatch, weighing scale, crocodile forceps, bedpan, cannula, cardioverter, defibrillator, catheter, dialyser, electrocardiograph machine, enema equipment, endoscope, gas cylinder, gauze sponge, hypodermic needle, syringe, infection control equipment, instrument sterilizer, kidney dish, measuring tape, medical halogen penlight, nasogastric tube, nebulizer, ophthalmoscope, otoscope, oxygen mask and tubes, pipette, dropper, proctoscope, reflex hammer, sphygmomanometer, spectrometer, dermatoscope, and camera. The physical condition of the subject may comprise vital signs of the subject. The vital signs may be measurements of the patient's basic body functions. The vital signs may include body temperature, pulse rate, respiration rate, and blood pressure.

Medical data or optical data of a subject may be paired with the subject through surgical a subject identity, so that a subject can retrieve his/her own information from a storage or a server through a subject identity. A subject identity may comprise patient's photo, name, address, social security number, birthday, telephone number, zip code, or any combination thereof. A patient identity may be encrypted and encoded in a visual graphical code. A visual graphical code may be a one-time barcode that can be uniquely associated with a patient identity. A barcode may be a UPC barcode, EAN barcode, Code 39 barcode, Code 128 barcode, ITF barcode, CodaBar barcode, GS1 DataBar barcode, MSI Plessey barcode, QR barcode, Datamatrix code, PDF417 code, or an Aztec barcode. A visual graphical code may be configured to be displayed on a display screen. A barcode may comprise QR that can be optically captured and read by a machine. A barcode may define an element such as a version, format, position, alignment, or timing of the barcode to enable reading and decoding of the barcode. A barcode can encode various types of information in any type of suitable format, such as binary or alphanumeric information. A QR code can have various symbol sizes as long as the QR code can be scanned from a reasonable distance by an imaging device. A QR code can be of any image file format (e.g., EPS or SVG vector graphs, PNG, TIF, GIF, or JPEG raster graphics format).

The process of generating datasets based on the optical data may comprise using one or more algorithms. The datasets may be selected optical data that represents one or more intrinsic properties of the tissue. The datasets can correspond to one or more depth profiles, images, layers of images or depth profiles indicating one or more intrinsic properties, characteristics, or structures of tissue. The datasets can include a plurality of depth profiles corresponding to different locations within the tissue of interest gathered by translating the optical probe while imaging. The one or more algorithms may be configured to select optical data, transfer optical data, and modify optical data. The one or more algorithms may comprise dimension reduction algorithms. Dimension reduction algorithms may comprise principal component regression and partial least squares. The principal component regression may be used to derive a low-dimensional set of features from a large set of variables. For instance, whether the tissue is at risk of cancer (a low-dimensional set of features) can be derived from all the intrinsic properties of the tissue (a large set of variables). The principal components used in the principal component regression may capture the most variance in the data using linear combinations of the data in subsequently orthogonal directions. The partial least squares may be a supervised alternative to principal component regression that makes use of the response variable in order to identify the new features.

The optical data may be uploaded to a cloud-based database, a database otherwise attached to a network, and the like. The datasets may be uploaded to a cloud-based database. The cloud-based database may be accessible from local and/or remote computer systems on which the machine learning-based sensor signal processing algorithms are running. The cloud-based database and associated software may be used for archiving electronic data, sharing electronic data, and analyzing electronic data. The optical data or datasets generated locally may be uploaded to a cloud-based database, from which it may be accessed and used to train other machine learning-based detection systems at the same site or a different site. Sensor device and system test results generated locally may be uploaded to a cloud-based database and used to update the training data set in real time for continuous improvement of sensor device and detection system test performance.

The trained algorithm may comprise one or more neural networks. A neural network may be a type of computational system that can learn the relationships between an input data set and a target data set. A neural network may be a software representation of a human neural system (e.g., cognitive system), intended to capture "learning" and "generalization" abilities as used by a human. A neural network may comprise a series of layers termed "neurons" or "nodes." A neural network may comprise an input layer, to which data is presented; one or more internal, and/or "hidden," layers; and an output layer. The input layer can include multiple depth profiles using signals that are synchronized in time and location. Such depth profiles, for example, can be generated using the optical probe as described elsewhere herein. Such depth profiles can comprise individual components, images, or depth profiles created from a plurality of subsets of gathered and processed signals. The depth profile may comprise a plurality of layers created from a plurality of subsets of images collected from the same location and time. Each of the plurality of layers may comprise data that identifies different anatomical structures and/or characteristics than those of the other layer(s). Such depth profile may comprise a plurality of sub-set depth profiles.

A neuron may be connected to neurons in other layers via connections that have weights, which are parameters that control the strength of a connection. The number of neurons in each layer may be related to the complexity of a problem to be solved. The minimum number of neurons required in a layer may be determined by the problem complexity, and the maximum number may be limited by the ability of a neural network to generalize. Input neurons may receive data being presented and then transmit that data to the first hidden layer through connections' weights, which are modified during training. The node may sum up the products of all pairs of inputs and their associated weights. The weighted sum may be offset with a bias. The output of a node or neuron may be gated using a threshold or activation function. An activation function may be a linear or non-linear function. An activation function may be, for example, a rectified linear unit (ReLU) activation function, a Leaky ReLu activation function, or other function such as a saturating hyperbolic tangent, identity, binary step, logistic, arcTan, softsign, parameteric rectified linear unit, exponential linear unit, softPlus, bent identity, softExponential, Sinusoid, Sinc, Gaussian, or sigmoid function, or any combination thereof.

A first hidden layer may process data and transmit its result to the next layer through a second set of weighted connections. Each subsequent layer may "pool" results from previous layers into more complex relationships. Neural networks may be programmed by training them with a sample set (data collected from one or more sensors) and allowing them to modify themselves during (and after) training so as to provide an output such as an output value. A trained algorithm may comprise convolutional neural networks, recurrent neural networks, dilated convolutional neural networks, fully connected neural networks, deep generative models, generative adversarial networks, deep convolutional inverse graphics networks, encoder-decoder convolutional neural networks, residual neural networks, echo state network, a long/short term memory network, gated recurrent units, and Boltzmann machines. A trained algorithm may combine elements of said neural networks or Boltzmann machines in full or in part.

Weighting factors, bias values, and threshold values, or other computational parameters of a neural network, may be "taught" or "learned" in a training phase using one or more sets of training data. For example, parameters may be trained using input data from a training data set and a gradient descent or backward propagation method so that output value(s) that a neural network computes are consistent with examples included in training data set.

The number of nodes used in an input layer of a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of node used in an input layer may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller. In some instance, the total number of layers used in a neural network (including input and output layers) may be at least about 3, 4, 5, 10, 15, 20, or greater. In other instances, the total number of layers may be at most about 20, 15, 10, 5, 4, 3 or less.

In some instances, the total number of learnable or trainable parameters, e.g., weighting factors, biases, or threshold values, used in a neural network may be at least about 10, 50, 100, 200, 300, 400, 500, 600, 700, 800, 900, 1000, 2000, 3000, 4000, 5000, 6000, 7000, 8000, 9000, 10,000, 20,000, 30,000, 40,000, 50,000, 60,000, 70,000, 80,000, 90,000, 100,000 or greater. In other instances, the number of learnable parameters may be at most about 100,000, 90,000, 80,000, 70,000, 60,000, 50,000, 40,000, 30,000, 20,000, 10,000, 9000, 8000, 7000, 6000, 5000, 4000, 3000, 2000, 1000, 900, 800, 700, 600, 500, 400, 300, 200, 100, 50, or 10 or smaller.

A neural network may comprise a convolutional neural network. A convolutional neural network may comprise one or more convolutional layers, dilated layers, or fully connected layers. The number of convolutional layers may be between 1-10 and dilated layers between 0-10. The total number of convolutional layers (including input and output layers) may be at least about 1, 2, 3, 4, 5, 10, 15, 20, or greater, and the total number of dilated layers may be at least about 1, 2, 3, 4, 5, 10, 15, 20, or greater. The total number of convolutional layers may be at most about 20, 15, 10, 5, 4, 3 or less, and the total number of dilated layers may be at most about 20, 15, 10, 5, 4, 3 or less. In some embodiments, the number of convolutional layers is between 1-10 and fully connected layers between 0-10. The total number of convolutional layers (including input and output layers) may be at least about 1, 2, 3, 4, 5, 10, 15, 20, or greater, and the total number of fully connected layers may be at least about 1, 2, 3, 4, 5, 10, 15, 20, or greater. The total number of convolutional layers may be at most about 20, 15, 10, 5, 4, 3 or less, and the total number of fully connected layers may be at most about 20, 15, 10, 5, 4, 3 or less.

A convolutional neural network (CNN) may be deep and feed-forward artificial neural networks. A CNN may be applicable to analyzing visual imagery. A CNN may comprise an input, an output layer, and multiple hidden layers. Hidden layers of a CNN may comprise convolutional layers, pooling layers, fully connected layers, and normalization layers. Layers may be organized in 3 dimensions: width, height, and depth.

Convolutional layers may apply a convolution operation to an input and pass results of a convolution operation to a next layer. For processing images, a convolution operation may reduce the number of free parameters, allowing a network to be deeper with fewer parameters. In a convolutional layer, neurons may receive input from a restricted subarea of a previous layer. Convolutional layer's parameters may comprise a set of learnable filters (or kernels). Learnable filters may have a small receptive field and extend through the full depth of an input volume. During a forward pass, each filter may be convolved across the width and height of an input volume, compute a dot product between entries of a filter and an input, and produce a 2-dimensional activation map of that filter. As a result, a network may learn filters that activate when it detects some specific type of feature at some spatial position in an input.

Pooling layers may comprise global pooling layers. Global pooling layers may combine outputs of neuron clusters at one layer into a single neuron in the next layer. For example, max pooling layers may use the maximum value from each of a cluster of neurons at a prior layer; and average pooling layers may use an average value from each of a cluster of neurons at the prior layer. Fully connected layers may connect every neuron in one layer to every neuron in another layer. In a fully-connected layer, each neuron may receive input from every element of a previous layer. A normalization layer may be a batch normalization layer. A batch normalization layer may improve a performance and stability of neural networks. A batch normalization layer may provide any layer in a neural network with inputs that are zero mean/unit variance. Advantages of using batch normalization layer may include faster trained networks, higher learning rates, easier to initialize weights, more activation functions viable, and simpler process of creating deep networks.

A neural network may comprise a recurrent neural network. A recurrent neural network may be configured to receive sequential data as an input, such as consecutive data inputs, and a recurrent neural network software module may update an internal state at every time step. A recurrent neural network can use internal state (memory) to process sequences of inputs. A recurrent neural network may be applicable to tasks such as handwriting recognition or speech recognition, next word prediction, music composition, image captioning, time series anomaly detection, machine translation, scene labeling, and stock market prediction. A recurrent neural network may comprise fully recurrent neural network, independently recurrent neural network, Elman networks, Jordan networks, Echo state, neural history compressor, long short-term memory, gated recurrent unit, multiple timescales model, neural Turing machines, differentiable neural computer, neural network pushdown automata, or any combination thereof.

A trained algorithm may comprise a supervised, partially supervised, or unsupervised learning method such as, for example, SVM, random forests, clustering algorithm (or software module), gradient boosting, logistic regression, generative adversarial networks, recurrent neural networks, and/or decision trees. It is possible according to some representative embodiments herein, to use a combination of supervised, partially supervised, or unsupervised learning methods to classify images. Supervised learning algorithms may be algorithms that rely on the use of a set of labeled, paired training data examples to infer the relationship between an input data and output data. An example of a labeled data set for supervised learning can be annotated depth profiles generated as described elsewhere herein. The annotated depth profiles can include user indicated regions of pixels within the depth profiles displaying known anatomical features. The known anatomical features can be of diseased or non-diseased tissues or elements of tissues. A partially supervised data set may include a plurality of depth profiles generated by translating the optical probe as described elsewhere herein. The plurality of profiles may be labeled as belonging to a tissues of subjects that have been previously or subsequently identified as having a disease or feature or not having a disease or feature without annotating regions of pixels within the individual profiles. Unsupervised learning algorithms may be algorithms used to draw inferences from training data sets to output data. Unsupervised learning algorithm may comprise cluster analysis, which may be used for exploratory data analysis to find hidden patterns or groupings in process data. One example of unsupervised learning method may comprise principal component analysis. Principal component analysis may comprise reducing the dimensionality of one or more variables. The dimensionality of a given variables may be at least 1, 5, 10, 50, 100, 200, 300, 400, 500, 600, 700, 800, 900, 1000, 1100, 1200 1300, 1400, 1500, 1600, 1700, 1800, or greater. The dimensionality of a given variables may be at most 1800, 1600, 1500, 1400, 1300, 1200, 1100, 1000, 900, 800, 700, 600, 500, 400, 300, 200, 100, 50, 10 or less.

A trained algorithm may be obtained through statistical techniques. In some embodiments, statistical techniques may comprise linear regression, classification, resampling methods, subset selection, shrinkage, dimension reduction, nonlinear models, tree-based methods, support vector machines, unsupervised learning, or any combination thereof.

A linear regression may be a method to predict a target variable by fitting the best linear relationship between a dependent and independent variable. The best fit may mean that the sum of all distances between a shape and actual observations at each point is the least. Linear regression may comprise simple linear regression and multiple linear regression. A simple linear regression may use a single independent variable to predict a dependent variable. A multiple linear regression may use more than one independent variable to predict a dependent variable by fitting a best linear relationship.

A classification may be a data mining technique that assigns categories to a collection of data in order to achieve accurate predictions and analysis. Classification techniques may comprise logistic regression and discriminant analysis. Logistic Regression may be used when a dependent variable is dichotomous (binary). Logistic regression may be used to discover and describe a relationship between one dependent binary variable and one or more nominal, ordinal, interval, or ratio-level independent variables. A resampling may be a method comprising drawing repeated samples from original data samples. A resampling may not involve a utilization of a generic distribution tables in order to compute approximate probability values. A resampling may generate a unique sampling distribution on a basis of an actual data. In some embodiments, a resampling may use experimental methods, rather than analytical methods, to generate a unique sampling distribution. Resampling techniques may comprise bootstrapping and cross-validation. Bootstrapping may be performed by sampling with replacement from original data, and take "not chosen" data points as test cases. Cross validation may be performed by split training data into a plurality of parts.

A subset selection may identify a subset of predictors related to a response. A subset selection may comprise best-subset selection, forward stepwise selection, backward stepwise selection, hybrid method, or any combination thereof. In some embodiments, shrinkage fits a model involving all predictors, but estimated coefficients are shrunken towards zero relative to the least squares estimates. This shrinkage may reduce variance. A shrinkage may comprise ridge regression and a lasso. A dimension reduction may reduce a problem of estimating n+1 coefficients to a simple problem of m+1 coefficients, where n<m. It may be attained by computing n different linear combinations, or projections, of variables. Then these n projections are used as predictors to fit a linear regression model by least squares. Dimension reduction may comprise principal component regression and partial least squares. A principal component regression may be used to derive a low-dimensional set of features from a large set of variables. A principal component used in a principal component regression may capture the most variance in data using linear combinations of data in subsequently orthogonal directions. The partial least squares may be a supervised alternative to principal component regression because partial least squares may make use of a response variable in order to identify new features.

A nonlinear regression may be a form of regression analysis in which observational data are modeled by a function which is a nonlinear combination of model parameters and depends on one or more independent variables. A nonlinear regression may comprise step function, piecewise function, spline, generalized additive model, or any combination thereof.

Tree-based methods may be used for both regression and classification problems. Regression and classification problems may involve stratifying or segmenting the predictor space into a number of simple regions. Tree-based methods may comprise bagging, boosting, random forest, or any combination thereof. Bagging may decrease a variance of prediction by generating additional data for training from original dataset using combinations with repetitions to produce multistep of the same carnality/size as original data. Boosting may calculate an output using several different models and then average a result using a weighted average approach. A random forest algorithm may draw random bootstrap samples of a training set. Support vector machines may be classification techniques. Support vector machines may comprise finding a hyperplane that best separates two classes of points with the maximum margin. Support vector machines may be constrained optimization problem where a margin is maximized subject to a constraint that it perfectly classifies data.

Unsupervised methods may be methods to draw inferences from datasets comprising input data without labeled responses. Unsupervised methods may comprise clustering, principal component analysis, k-Mean clustering, hierarchical clustering, or any combination thereof.

The method may train a machine learning algorithm to yield a trained algorithm in computer memory for identifying the disease in the tissue of the subject at an accuracy of at least 90%, wherein the tissue is independent of the training tissues. The method may train a machine learning algorithm to yield a trained algorithm in computer memory for identifying the disease in the tissue of the subject at an accuracy of at least 50%, 60%, 70%, 80%, 90% or greater. In some cases, the method may train a machine learning algorithm to yield a trained algorithm in computer memory for identifying the disease in the tissue of the subject at an accuracy of at most 90%, 80%, 70%, 60%, 50% or greater.

A method may train using a plurality of virtual cross-sections. The virtual cross sections may comprise a plurality of layers, images and/or depth profiles that were obtained using an excitation light beam directed at tissue at a synchronized time and location. A virtual cross-section may comprise depth profiles from an in vivo sample. Examples of a virtual cross section that can be used is illustrated as an image derived from one or more synchronized depth profiles in FIG. 7D.

Systems for Training an Algorithm

Disclosed herein are systems for generating a trained algorithm for identifying a disease in a tissue of a subject. A system for generating a trained algorithm for identifying a disease in a tissue of a subject may comprise a database comprising data corresponding to depth profiles, related images, and or layers thereof, of training tissues of subjects that have been previously identified as having the disease, which depth profiles related images, and or layers thereof, are generated signals and data synchronized or correlated in time and location; which depth profiles, related images, and or layers thereof are generated from signals generated from an excitation light beam; and/or which depth profiles, related images, and or layers thereof are generated from signals selected from the group consisting of second harmonic generation signal, third harmonic generation signal, reflectance confocal microscopy signal, autofluorescence signal and other generated signals described herein; and one or more computer processors operatively coupled to the database, wherein the one or more computer processors are individually or collectively programmed to (i) retrieve the data from the database and (ii) use the data to train a machine learning algorithm to yield a trained algorithm in computer memory for identifying the disease in the tissue of the subject, wherein the tissue is independent of the training tissues.

The optical data is described elsewhere herein. The optical data may comprise second harmonic generation signal, third harmonic generation signal, reflectance confocal microscopy signal, and autofluorescence signal and/or other generated signals as defined herein. The apparatus may be connected to a database. The optical data may be stored in the database. The database may be a centralized database. The database may be connected with the one or more processors. The one or more processors may analyze the data stored in the database through one or more algorithms. The analysis performed by the one or more processors may include, but not limited to, selecting optical data, creating datasets based on optical data, obtaining the patient health status from one or more databases, and yield a training algorithm based on data obtained. The one or more processors may provide one or more instructions based on the analysis.

The one or more instructions may be displayed on a display screen. The display screen may be a detachable display screen. The display screen may have a zoom function. The display screen may comprise editable feature that allows for marking of the epithelial features on the display screen. The display screen may be split and comprises the macroscopic image and the polychromatic image created from the depth profile. The display screen may be a liquid crystal display, similar to a tablet computer. The display screen may be accompanied by one or more speakers, and may be configured for providing visual and audial instructions to a user. The one or more instructions may comprise showing whether the subject has the rick of certain types of cancer, requesting the subject to take a given medication or go through a given treatment based on whether the subject has the risk of cancer. The one or more instructions may also comprise requesting the subject to provide his/her health status.

The depth profile can comprise a monochromatic image displaying colors derived from a single base hue. Alternatively or additionally, the depth profile can comprise a polychromatic image displaying more than one color. In a polychromatic image, color components may correspond to multiple depth profiles using signals or subsets of signals that are synchronized in time and location. Such depth profiles, for example, may be generated using the optical probe as described elsewhere herein. Such depth profiles can comprise individual components, images or depth profiles created from a plurality of subsets of gathered and processed generated signals. The depth profile may comprise a plurality of layers created from a plurality of subsets of images collected from the same location and time. Each of the plurality of layers may comprise data that identifies different anatomical structures and/or characteristics than those of the other layer(s). Such depth profiles may comprise a plurality of sub-set depth profiles. In this manner multiple colors can be used to highlight different elements of the tissue such as cells, nuclei, cytoplasm, connective tissues, vasculature, pigment, and tissue layer boundaries. The contrast can be adjusted in real-time to provide and/or enhance structure specific contrast. The contrast can be adjusted by a user (e.g. surgeon, physician, nurse, or other healthcare practitioner) or a programmed computer processor may automatically optimize the contrast in real-time. In a polychromatic image, each color may be used to represent a specific subset of the signals collected, such as second harmonic generation signals, third harmonic generation signals, signals resulting from polarized light, and autofluorescence signals. The colors of a polychromatic depth profile can be customized to reflect the image patterns a surgeon and/or pathologist may typically see when using standard histopathology. A pathologist may more easily interpret the results of a depth profile when the depth profile is displayed similar to how a traditional histological sample, for example a sample stained with hematoxylin and eosin, may be seen.

The optical probe may transmit an excitation light beam from a light source towards a surface of a reference tissue, which excitation light beam, upon contacting the tissue, generate the optical data of the tissue. The optical probe may comprise one or more focusing units to simultaneously adjust a depth and a position of a focal point of the excitation light beam along a scanning path or scanning pattern or at a different depth and position.

The scan path or scan pattern may comprise a path or pattern in at least one slant direction ("slanted path" or "slanted pattern"). The at least one slanted path or slanted pattern may be angled with respect to an optical axis. The angle between a slanted path or slanted pattern and the optical axis may be at most 45°. The angle between a slanted path or slanted pattern and the optical axis may be at least about 5°, 10°, 15°, 20°, 25°, 30°, 35°, 40°, 45°, 55°, 60°, 65°, 70°, 75°, 80°, 85°, or greater. In other cases, the angle between the slanted path or slanted pattern and the optical axis may be at most about 85°, 80°, 75°, 70°, 65°, 60°, 55°, 50°, 45°, 35°, 30°, 25°, 20°, 15°, 10°, 5°, or less.

The scan path or scan pattern may form a focal plane and/or lie on at least one slanted plane. The at least one slanted plane may be positioned along a direction that is angled with respect to an optical axis. The angle between a slanted plane and the optical axis may be at most 45°. The angle between a slanted plane and the optical axis may be at least about 5°, 10°, 15°, 20°, 25°, 30°, 35°, 40°, 45°, 55°, 60°, 65°, 70°, 75°, 80°, 85°, or greater. In other cases, the angle between the slanted plane and the optical axis may be at most about 85°, 80°, 75°, 70°, 65°, 60°, 55°, 50°, 45°, 35°, 30°, 25°, 20°, 15°, 10°, 5°, or less.

The identifying the disease may be at an accuracy of at least about 50%, 60%, 70%, 80%, 90%, 95%, 99%, 99.9%, or more. The identifying the disease may be at an accuracy of at most about 99.9%, 99%, 95%, 90%, 80%, 70%, 60%, 50%, or less.

The disease may be epithelial cancer.

The optical data may further comprise structured data, time-series data, unstructured data, and relational data. The unstructured data may comprise text, audio data, image data and/or video. The relational data may comprise data from one or more of a customer system, an enterprise system, an operational system, a website, or web accessible application program interface (API). This may be done by a user through any method of inputting files or other data formats into software or systems.

The optical data may be uploaded to, for example, a cloud-based database or other remote or networked database. The datasets may be uploaded to, for example, a cloud-based database or other remote or networked database. The cloud-based database may be accessible from local and/or remote computer systems on which the machine learning-based sensor signal processing algorithms are running. The cloud-based database and associated software may be used for archiving electronic data, sharing electronic data, and analyzing electronic data. The optical data or datasets generated locally may be uploaded to a cloud-based database, from which it may be accessed and used to train other machine learning-based detection systems at the same site or a different site. Sensor device and system test results generated locally may be uploaded to a cloud-based database and used to update the training data set in real time for continuous improvement of sensor device and detection system test performance.

The data may be stored in a database. A database can be stored in computer readable format. A computer processor may be configured to access the data stored in the computer readable memory. A computer system may be used to analyze the data to obtain a result. The result may be stored remotely or internally on storage medium, and communicated to personnel such as medication professionals. The computer system may be operatively coupled with components for transmitting the result. Components for transmitting can include wired and wireless components. Examples of wired communication components can include a Universal Serial Bus (USB) connection, a coaxial cable connection, an Ethernet cable such as a Cat5 or Cat6 cable, a fiber optic cable, or a telephone line. Examples or wireless communication components can include a Wi-Fi receiver, a component for accessing a mobile data standard such as a 3G or 4G LTE data signal, or a Bluetooth receiver. In some embodiments, all these data in the storage medium is collected and archived to build a data warehouse.

The training of a machine learning algorithm may yield a trained algorithm in computer memory for identifying the disease in the tissue of the subject wherein the tissue is independent of the training tissues. The training of a machine learning algorithm may yield a trained algorithm in computer memory for identifying the disease in the tissue of the subject at an accuracy of at least 50%, 60%, 70%, 80%, 90% or greater. In some cases, the training of a machine learning algorithm may yield a trained algorithm in computer memory for identifying the disease in the tissue of the subject at an accuracy of at most 90%, 80%, 70%, 60%, 50% or greater.

Machine Learning Methods and Systems

Disclosed herein are methods for analyzing tissue of a body of a subject. In an aspect, a method for analyzing tissue of a body of a subject may comprise (a) directing light to the tissue of the body of the subject; (b) receiving a plurality of signals from the tissue of the body of the subject in response to the light directed thereto in (a), wherein at least a subset of the plurality of signals are from within the tissue; (c) inputting data corresponding to the plurality of signals to a trained machine learning algorithm that processes the data to generate a classification of the tissue of the body of the subject; and outputting the classification on a user interface of an electronic device of a user.

The classification may identify the subject as having a disease. The disease may be a disease as described elsewhere herein. The disease may be a cancer. The tissue of the subject may be a skin of the subject, and the cancer may be skin cancer. The cancer may be benign or malignant. The classification may identify the tissue as having the disease at an accuracy of at least about 50%, 60%, 70%, 80%, 90%, 95%, 98%, 99%, 99.9%, or more.

The plurality of signals may comprise a second harmonic generation (SHG) signal, a multi photon fluorescence signal, a reflectance confocal microscopy (RCM) signal, any other generated signals described herein, or any combination thereof. The multi photon fluorescence signal may be a plurality of multi photon fluorescence signals. The plurality of multi photon fluorescence signals may be at a plurality of wavelengths. The plurality of multi photon fluorescence signals may be generated by a plurality of components of the tissue. The method may comprise identifying one or more features corresponding to the plurality of signals using the trained machine learning algorithm. A plurality of signals may be filtered such that fewer signals than are recorded are used. A plurality of generated signals may be used to generate a plurality of depth profiles.

The trained machine learning algorithm may comprise a neural network. The neural network may be a convolutional neural network. The data may be controlled for an illumination power of the optical signal. The control may be normalization. The data may be controlled for an illumination power by the trained machine learning algorithm. The data may be controlled for an illumination power before the trained machine learning algorithm is applied. The convolutional neural network may be configured to use colorized data as an input of the neural network.

The method may comprise receiving medical data of the subject. The medical data may be as described elsewhere herein. The medical data may be uploaded to a cloud or network attached device. The data may be kept on a local device.

The method may be configured to use data augmentation to improve the trained machine learning algorithm. For example, an augmented data set can be a data set where a fast image capture created a dataset with a number of similar, but not the same, images from a tissue.

The method may be configured to use images taken using a controlled power of illumination. The controlled power of illumination may improve the performance of the trained machine learning algorithm. For example, a controlled illumination can enable a trained machine learning algorithm to attribute differences between two images to differences in a tissue rather than differences in the conditions used to take the images, thus improving the accuracy of the trained machine learning algorithm.

The method may be configured to use data with minimal variations to improve the trained machine learning algorithm. For example, due to the low variation in image parameters generated by optical probes described herein the trained machine learning algorithm can more accurately determine if a lesion is cancerous, if tissue is normal or abnormal, or other features of the tissue in a subject pertaining to the health, function, treatment, or appearance of said tissues as all images used by the trained machine learning algorithm use the same labeling and coloring scheme. The method may be configured to use data generated from an excitation light beam interacting with a tissue. The excitation light beam may generate a plurality of depth profiles for use in a trained machine learning algorithm. The excitation light beam may generate a plurality of depth profiles to train a machine learning algorithm. The excitation light beam may generate a depth profile from a subset of a plurality of return signals.

The trained machine learning algorithm may be trained to generate a spatial map of the tissue. The spatial map may be a three-dimensional model of the tissue. The spatial map may be annotated by a user and/or the trained machine learning algorithm.

Disclosed herein are systems for analyzing tissue of a body of a subject. In an aspect, a system for analyzing tissue of a body of a subject may comprise an optical probe that is configured to (i) direct light to the tissue of the body of the subject, and (ii) receive a plurality of signals from the tissue of the body of the subject in response to the light directed thereto in (i), wherein at least a subset of the plurality of signals are from within the tissue; and one or more computer processors operatively coupled to the optical probe, wherein the one or more computer processors are individually or collectively programmed to (i) receive data corresponding to the plurality of signals, (ii) input the data to a trained machine learning algorithm that processes the data to generate a classification of the tissue of the body of the subject, and (iii) output the classification on a user interface of an electronic device of a user.

The optical probe and the one or more computer processors may comprise a same device. The device may be a mobile device. The device may be a plurality of devices that may be operatively coupled to one another. For example, the system can be a handheld optical probe optically connected to a laser and detection box, and the box can also contain a computer.

The optical probe may be part of a device, and the one or more computer processors may be separate from the device. The one or more computer processors may be part of a computer server. The one or more processors may be part of a distributed computing infrastructure. For example, the system can be a handheld optical probe containing all of the optical components that is wirelessly connected to a remote server that processes the data from the optical probe.

The system may comprise receiving medical data of the subject. The medical data may be as described elsewhere herein. The medical data may be uploaded to a cloud or network attached device. The data may be kept on a local device.

Computer Systems

Figure 6:
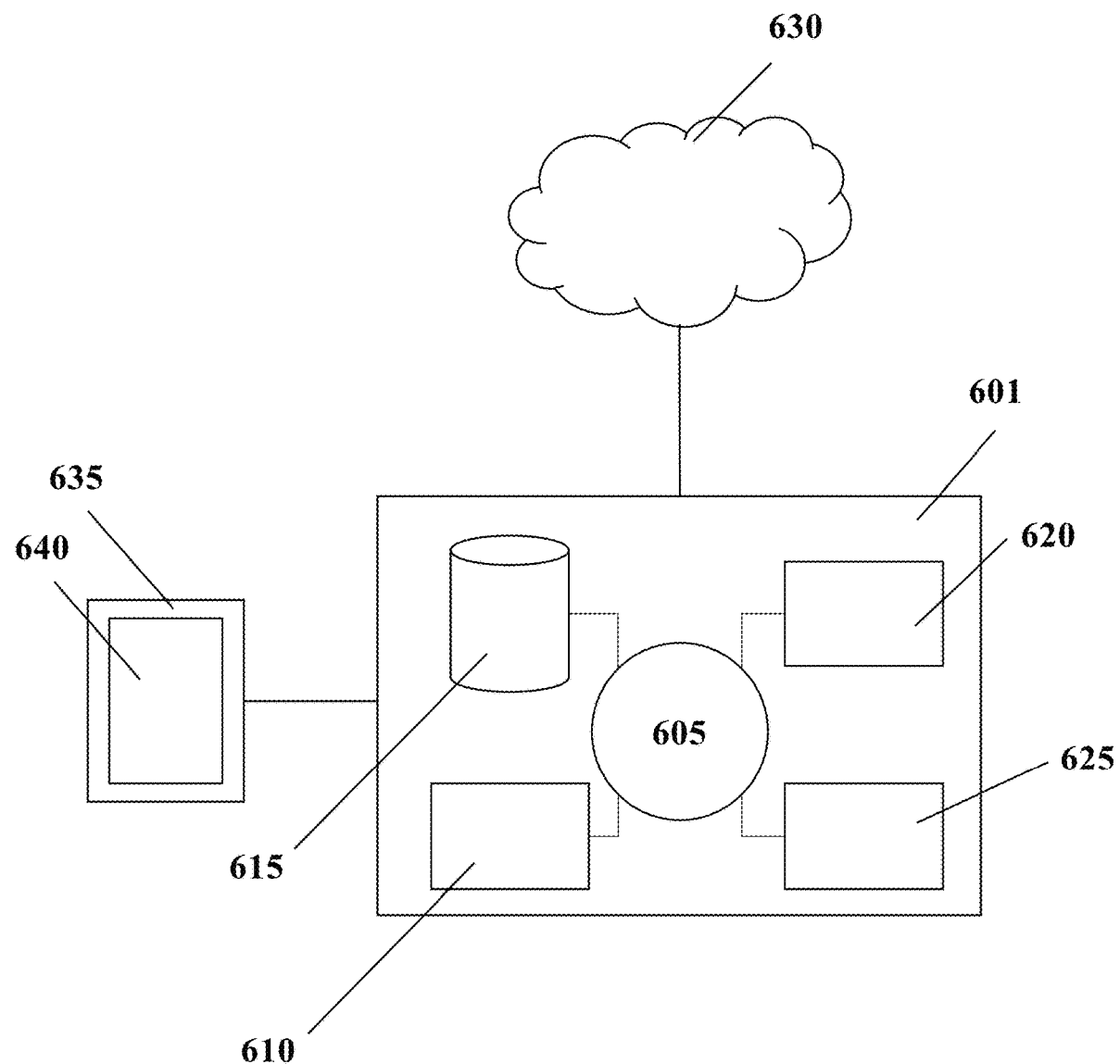
FIG. 6 shows a computer system that is programmed or otherwise configured to implement methods provided herein.

The present disclosure provides computer systems that are programmed to implement methods of the disclosure. FIG. 6 shows a computer system 601 that is programmed or otherwise configured to receive the optical data and generate a trained algorithm. The computer system 601 can regulate various aspects of the present disclosure, such as, for example, receiving and selecting the optical data, generating datasets based on the optical data, and creating a trained algorithm. The computer system 601 can be an electronic device of a user or a computer system that is remotely located with respect to the electronic device. The electronic device can be a mobile electronic device. The electronic device may be configured to receive optical data generated from a light source of a probe system. The optical data may comprise one or more types of optical data as described herein. For example, the electronic device can receive second harmonic generation signal, two photon fluorescence signal, reflectance confocal microscopy signal, or other generated signals, all generated by one light source and collected by one handheld system. The optical data may comprise two or more layers of information. The two or more layers of information may be information generated from data generated from the same light pulse of the single probe system. The two or more layers may be from a same depth profile or may each form a distinct depth profile. Distinct depth profiles forming one layer of a composite depth profile may or may not be separately trainable. For example, a depth profile can be generated by taking two-photon fluorescence signals from epithelium, SHG signals from collagen, and RCM signals from melanocytes and pigment, overlaying the signals, and generating a multicolor, multi-layer, depth profile.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries, and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user (e.g., phone). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine-readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, results of the optical data analysis to the user. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, be used for selecting data, identifying features in the data, and/or classifying the data.

Refractive Alignment Methods and Systems

Also provided herein a method for aligning a light beam (e.g., aligning a light beam between a beam splitter and an optical fiber). In some cases, the method of aligning a light beam can be used to align a beam of light between any two components. For example, a focused beam of light can be aligned between a lens and a pinhole using a refractive element. In another example, a beam of light can be aligned to a specific region of a sample using the methods and systems described herein.

In an aspect, a method of the present disclosure may comprise providing (i) a light beam in optical communication with a beam splitter. The beam splitter is in optical communication with a lens. The lens may be in optical communication with a refractive element, (ii) an optical fiber, and (iii) a detector in optical communication with the optical fiber. An optical path from the refractive element may be misaligned with respect to the optical fiber. In an aspect, the method may further comprise adjusting the refractive element to align the optical path with the optical fiber. In an aspect, the method may further comprise directing the light beam to the beam splitter that splits the light beam into a beamlet. The beamlet may be directed through the lens to the refractive element that directs the beamlet along the optical path to the optical fiber, such that the detector detects the beamlet.

The method of aligning a light beam using a refractive element may allow for significantly faster and easier alignment of a beam of light to a fiber optic. The method may allow for a single mode fiber optic to be aligned in less than about 60, 45, 30, 15, 5, or less minutes with high long-term stability. The method may allow for a small alignment adjustment to be performed by a large adjustment to the refractive element, which may give fine control of the alignment adjustment.

The beamlet may be directed to an additional element that reflects the beamlet to the beam splitter, which beam splitter directs the beamlet through the lens to the refractive element. The additional element may be a mirror. The mirror may be used in the alignment process by providing a strong signal to align with. The beamlet may be directed from the beam splitter through one or more additional elements prior to being reflected by the refractive element. The additional elements may be the elements of the optical probe described elsewhere herein. The additional elements may be a mirror scanner, a focus lens pair, a plurality of relay lenses, a dichroic mirror, an objective, a lens, or any combination thereof. The refractive element may be operatively coupled to a lens. The refractive element and a lens may be on the same or different mounts.

The point spread function of the beamlet after interacting with the refractive element may be sufficiently small to enable a resolution of the detector to be less than about 200, 150, 100, 75, 50, 40, 30, 25, 20, 15, 10, 9, 8, 7, 6, 5, 4, 3, 2, 1, 0.9, 0.8, 0.7, 0.6, 0.5, or less microns. For example, the refractive element may introduce astigmatism or defocus into the beamlet, but the astigmatism or defocus is sufficiently small as to not impact the overall resolution of the detector (e.g., the astigmatism or defocus can be less than the diffraction point spread function). The refractive element may be a flat window, a curved window, a window with surface patterning, or the like.

The adjusting the position may comprise applying a rotation of the refractive element. The adjusting the position may comprise a translation of the refractive element. The rotation may be at most about 180, 170, 160, 150, 125, 100, 90, 80, 70, 60, 50, 40, 30, 20, 10, 9, 8, 7, 6, 5, 4, 3, 2, 1 degree, or less. The rotation may be at most about 1, 2, 3, 4, 5, 6, 7, 8, 9, 10, 20, 30, 40, 50, 60, 70, 80, 90, 100, 125, 150, 179 degrees, or more. The rotation or translation or both may be in at most three, two, or one dimensions. An adjustment ratio of the refractive alignment can be defined as the degree of misalignment divided by the deflection of the refractive element that corrects the misalignment. For example, a beam of light that is 0.05 degrees out of alignment that is corrected by a rotation of 20 degrees of the refractive element can have an adjustment ratio of 0.05/20=0.0025 or 2.5E-3. The adjustment ratio may be at least about 1E-5, 5E-5, 1E-4, 5E-4, 1E-3, 5E-3, 1E-2, 5E-2, 1E-1, 1, 5, or more. The adjustment ratio may be at most about 5, 1, 5E-1, 1E-1, 5E-2, 1E-2, 5E-3, 1E-3, 5E-4, 1E-4, 5E-5, 1E-5, or less.

Also disclosed herein are systems for aligning a light beam. In an aspect, a system for aligning a light beam may comprise a light source that is configured to provide a light beam; a focusing lens in optical communication with the light beam; a moveable refractive element in optical communication with the lens; an optical fiber; and a detector in optical communication with the optical fiber wherein the refractive element is positioned between the focusing lens and the optical fiber. The refractive alignment element may be adjustable to align the optical path with the optical fiber, such that, when the optical path is aligned with the optical fiber, the light beam may be directed through the lens to the refractive element that directs the beam along the optical path to the optical fiber, such that the detector detects the beam. The refractive alignment element may be rotationally or angularly moveable with respect to the optical fiber and/or the optical fiber mount.

Figure 9A:
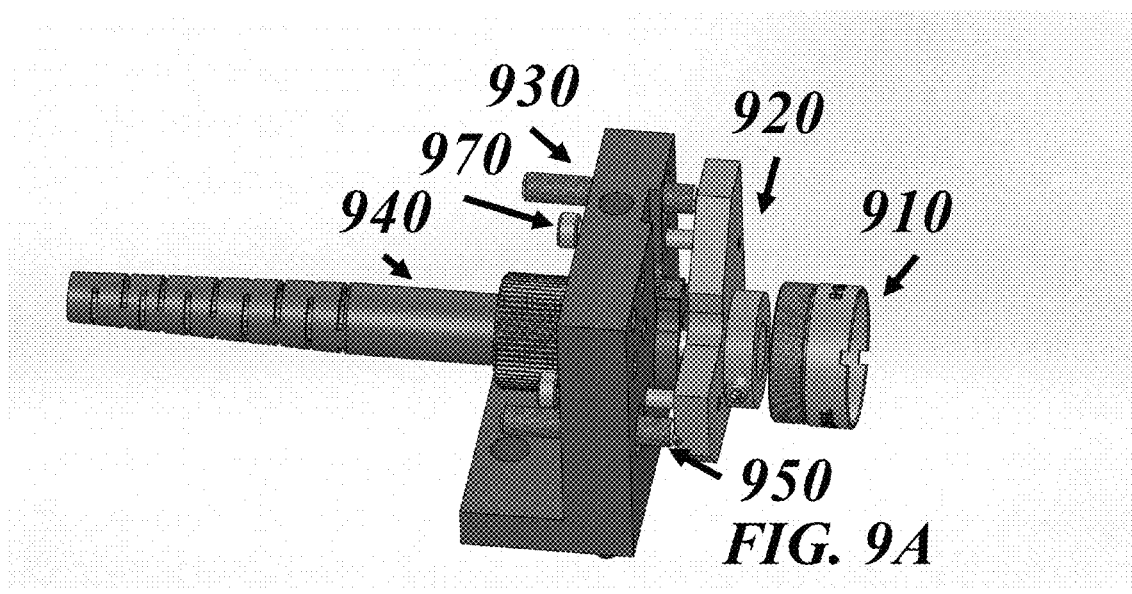
FIGS. 9A-9C shows an example refractive alignment setup system.
Figure 9B:
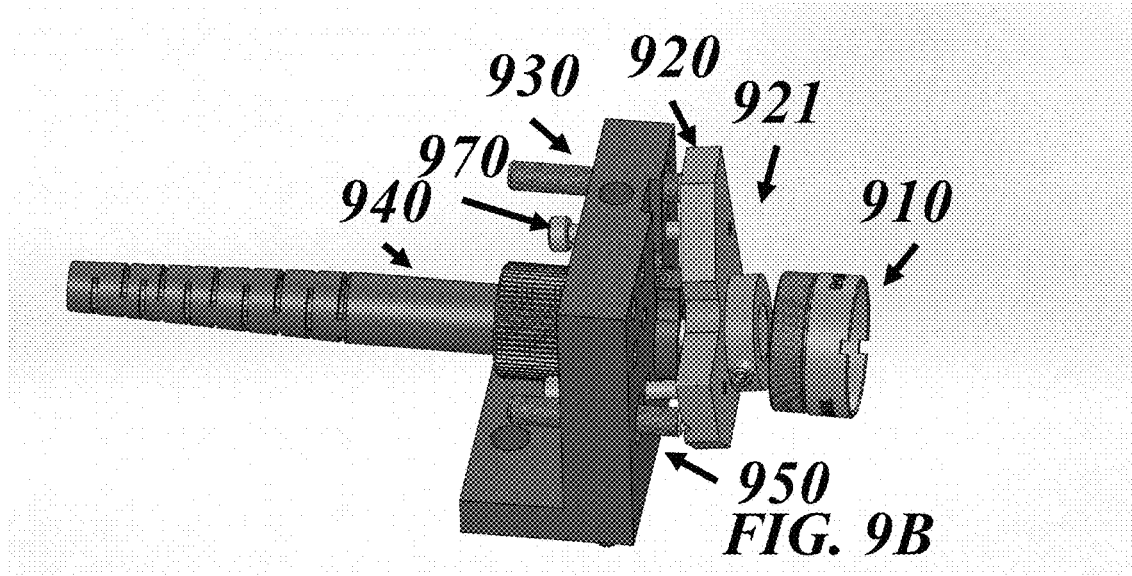
Figure 9C:
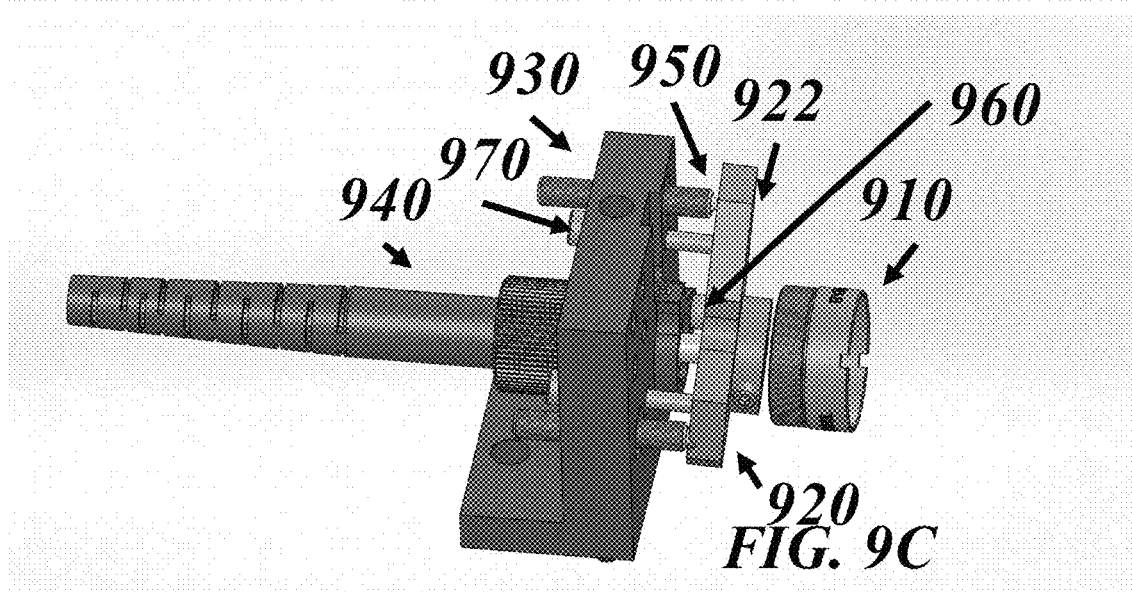

FIGS. 9A, 9B, and 9C show an example alignment arrangement described elsewhere herein. A lens 910 may be configured to focus a beam of light onto optical fiber 940. Refractive alignment element 920 may be placed between the lens and the optical fiber. Refractive alignment element 920 may be operatively coupled to mount 930. Refractive alignment element 920 may be adjusted to align the light beam with the optical fiber. For example, if the light beam is too high, the refractive element can be adjusted to position 921, thus deflecting the light beam down into the fiber. In another example, if the light beam is too low, the refractive element can be adjusted to position 922 to correct the misalignment. Adjustment elements 950 can be used to angularly or rotationally move the refractive alignment element 920 with respect to the fiber optic. Adjustment elements 950 may be screws, motorized screws, piezoelectric adjusters, and the like. The refractive alignment element is shown with adjustment elements that move the refractive adjustment element angularly with respect to the optical fiber mount while the refractive element is stabilized with a ball element 960 positioned between the refractive adjustment element and the mount, and with spring loaded screws 970 coupling the refractive alignment element and mount.

The light beam can be a beamlet split from a beam splitter prior to directing the beamlet to the alignment arrangement. The alignment arrangement can further comprise a moveable mirror positioned between the beam splitter and the focusing lens (for example, as shown in FIGS. 1 and 8). The mirror may be used to direct split signals from the beam splitter to the alignment arrangement. The mirror can be moveable and/or adjustable to provide larger alignment adjustments of the beamlet entering the focusing lens. The mirror can be positioned one focal length in front of the refractive alignment element for example, to cause the chief ray of the beamlet to remain parallel or nearly parallel to the optical axis of the lens during mirror adjustments. The mirror may also be a beam splitter or may be a polarized optical element to split the reflected signal into signal elements with different polarizations. Once split, the split signals can be directed through different alignment arrangements and through separate channels for processing. A separate polarizer may also be used to split the beamlet into polarized signals.

The focusing lens may focus the light of the beamlet to a diffraction limited or nearly diffraction limited spot. The refractive alignment element may be used to correct any additional fine misalignment of the beamlet to the fiber optic. The refractive alignment element can have a refractive index, thickness and/or range of motion (e.g., a movement which alters the geometry) that permits alignment of the beamlet exiting the lens to a fiber optic have a diameter less than about 20 microns, 10 microns, 5 microns, or less. According to some representative embodiments, the refractive alignment element properties (including refractive index, thickness, and range of motion) may be selected so that the aberrations introduced by the refractive alignment element do not increase the size the beamlet focused on the optical fiber by more than 0%, 1%, 2%, 5%, 10%, 20%, or more above the focusing lens's diffraction limit. The alignment arrangement can be contained within a handheld device.

The beamlet may comprise polarized light. The optical probe may comprise one or more polarization selective optics (e.g., polarization filters, polarization beam splitters, etc.). The one or more polarization selective optics may be selected for a particular polarization of the beamlet, such that the beamlet that is detected is of a particular polarization.

The system may comprise a controller operatively coupled to the refractive element. The controller may be programmed to direct adjustment of the refractive element to align the optical path with the optical fiber. The adjustment may also be performed with an input of a user or manually. The adjustment may be performed by an actuator operatively coupled to the refractive element. The actuator may be an actuator as described elsewhere herein. For example, a piezoelectric motor can be attached to a three-axis optical mount holding a flat plate of quartz, and the piezoelectric motor can be controlled by an alignment algorithm programmed to maximize signal of the detector. The adjustment may be performed by a user. For example, a user can adjust a micrometer that is attached to a three-axis optical mount holding a flat plate of glass, moving the stage until an acceptable level of signal is read out on the detector.

The refractive element may be a flat window, a curved window, a flat window with a patterned surface, a curved window with a patterned surface, a photonic structure, or the like. The refractive element may be made of glass, quartz, calcium fluoride, germanium, barium, fused silica, sapphire, silicon, zinc selenide, magnesium fluoride, and a plastic. The refractive element may have an index of refraction greater than 2.

The point spread function of the beam after interacting with the refractive element may be sufficiently small to enable a resolution of the detector to be less than about 200, 150, 100, 75, 50, 40, 30, 25, 20, 15, 10, 9, 8, 7, 6, 5, 4, 3, 2, 1, 0.9, 0.8, 0.7, 0.6, 0.5 microns, or less. The refractive element may be configured to adjust the beam at most about 45, 40, 35, 30, 25, 20, 15, 10, 5, 4, 3, 2, 1, 0.5, 0.1, 0.01 degrees, or less. The refractive element may be configured to adjust the beam at least about 0.01, 0.1, 0.5, 1, 2, 3, 4, 5, 6, 7, 8, 9, 10, 15, 20, 25, 30, 35, 40, 45 degrees, or more. The refractive element may be adjusted to change the amount of adjustment. For example, the refractive element was set to a deflection of 60 degrees, but the system has fallen out of alignment. In this example, the refractive element can be adjusted to generate an adjustment of 15 degrees to bring the system back into alignment.

The refractive element may have a footprint of at most about 100, 90, 80, 70, 60, 50, 40, 30, 20, 10, 5, 4, 3, 2, 1, 0.5, 0.1 square inches, or less. The refractive element and an associated housing may have a footprint of at most about 100, 90, 80, 70, 60, 50, 40, 30, 20, 10, 5, 4, 3, 2, 1, 0.5, 0.1 square inches, or less. The refractive element may have a footprint of at least about 0.1, 0.5, 1, 2, 3, 4, 5, 10, 20, 30, 40, 50, 60, 70, 80, 90, 100 square inches, or more. The refractive element and an associated housing may have a footprint of at least about 0.1, 0.5, 1, 2, 3, 4, 5, 10, 20, 30, 40, 50, 60, 70, 80, 90, 100 square inches, or more.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

Further Aspects of the Disclosure

1. A method for generating a depth profile of a tissue of a subject, comprising:
   (a) using an optical probe to transmit an excitation light beam from a light source to a surface of said tissue, which pulses of said excitation light beam, upon contacting said tissue, yield signals indicative of an intrinsic property of said tissue, wherein said optical probe comprises one or more focusing units that simultaneously adjust a depth and a position of a focal point of said excitation light beam;
   (b) detecting at least a subset of said signals; and
   (c) using one or more computer processors programmed to process said at least said subset of said signals detected in (b) to generate said depth profile of said tissue.
2. The method of aspect 1, wherein said excitation light beam is a pulsed light beam.
3. The method of aspect 1, wherein said excitation light beam is a single beam of light.
4. The method of aspect 3, wherein said single beam of light is a pulsed beam of light.
5. The method of aspect 1, wherein said excitation light beam comprises multiple beams of light.
6. The method of aspect 1, wherein (b) comprises simultaneously detecting a plurality of subsets of said signals.
7. The method of aspect 1, further comprising processing said plurality of subsets of said signals to generate a plurality of depth profiles, wherein said plurality of depth profiles correspond to a probe position at a time of detecting said signals.
8. The method of aspect 7, wherein said plurality of depth profiles corresponds to a same scanning path.
9. The method of aspect 8, wherein said scanning path comprises a slanted scanning path.
10. The method of aspect 7, further comprising assigning a least one distinct color for each of said plurality of depth profiles.
11. The method of aspect 7, further comprising combining at least a subset of data from said plurality of depth profiles to form a composite depth profile.
12. The method of aspect 7, further comprising displaying, on a display screen, a composite image derived from said composite depth profile.
13. The method of aspect 12, wherein said composite image is a polychromatic image.
14. The method of aspect 13, wherein color components of said polychromatic images correspond to multiple depth profiles using subsets of signals that are synchronized in time and location.
15. The method of aspect 13, wherein each of said plurality of layers comprise data that identifies different characteristics than those of other layers.
16. The method of aspect 13, wherein said depth profiles comprises a plurality of sub-set depth profiles, wherein said plurality of sub-set depth profiles comprise optical data from processed generated signals.
17. The method of aspect 7, wherein said plurality of depth profiles comprises a first depth profile and a second depth profile.
18. The method of aspect 17, wherein said first depth profile comprises data processed from a signal that is different from data generated from a signal comprised in said second depth profile.
19. The method of aspect 17, wherein said first depth and said second depth profile comprise one or more processed signals independently selected from the group consisting of a second harmonic generation (SHG) signal, a multi photon fluorescence signal, and a reflectance confocal microscopy (RCM) signal.
20. The method of aspect 17, wherein said plurality of depth profile comprises a third depth profile comprising data processed from a signal selected from the group consisting of a SHG signal, a multi photon fluorescence signal, and an RCM signal.
21. The method of aspect 1, wherein said depth profile comprises individual components, images, or depth profiles created from a plurality of subsets of said signals.
22. The method of aspect 1, wherein said depth profile comprises a plurality of layers created from a plurality of subsets of images collected from a same location and time.

23. The method of aspect 1, further comprising generating a plurality of depth profiles.
24. The method of aspect 23, wherein each of said plurality of depth profiles corresponds to a different probe position.
25. The method of aspect 23, wherein said plurality of depth profiles correspond to different scan patterns at the time of detecting the signals.
26. The method of aspect 25, wherein said different scan patterns correspond to a same time and probe position.
27. The method of aspect 25, wherein at least one scanning pattern of said different scan patterns comprises a slanted scanning pattern.
28. The method of aspect 27, wherein said slanted scanning pattern forms a slanted plane.
29. The method of aspect 1, wherein said tissue comprises in vivo tissue.
30. The method of aspect 29, wherein (c) comprises generating an in vivo depth profile.
31. The method of aspect 1, wherein said depth profile is an annotated depth profile.
32. The method of aspect 31, wherein said annotation comprises at least one annotation selected from the group consisting of words and markings.
33. The method of aspect 1, wherein said signals comprise at least one signal selected from the group consisting of an SHG signal, a multi photon fluorescence signal, and an RCM signal.
34. The method of aspect 33, wherein said multi photon fluorescence signal comprises a plurality of multi photon fluorescence signals.
35. The method of aspect 33, wherein said signals comprise at least two signals selected from the group consisting of an SHG signal, a multi photon fluorescence signal, and an RCM signal.
36. The method of aspect 35, wherein said signals comprise an SHG signal, a multi photon fluorescence signal, and an RCM signal.
37. The method of aspect 33, wherein said signals further comprise at least one signal selected from the group consisting of third harmonic generation signals, coherent anti-stokes Raman scattering signals, stimulated Raman scattering signals, and fluorescence lifetime imaging signals.
38. The method of aspect 1, wherein said signals are generated at a same time and location within said tissue.
39. The method of aspect 1, further comprising, prior to (a), contacting said tissue of said subject with said optical probe.
40. The method of aspect 1, further comprising adjusting said depth and said position of said focal point of said excitation light beam along a scanning path.
41. The method of aspect 40, wherein said scanning path is a slanted scanning path.
42. The method of aspect 41, wherein said slanted scanning path forms a slanted plane positioned along a direction that is angled with respect to an optical axis of said optical probe.
43. The method of aspect 42, wherein an angle between said slanted plane and said optical axis is greater than 0 degrees and less than 90 degrees.
44. The method of aspect 1, wherein (a)-(c) are performed in an absence of administering a contrast enhancing agent to said subject.
45. The method of aspect 1, wherein said excitation light beam comprises unpolarized light.
46. The method of aspect 1, wherein said excitation light beam comprises polarized light.
47. The method of aspect 1, wherein said detecting is performed in a presence of ambient light.
48. The method of aspect 1, wherein (a) is performed without penetrating said tissue of said subject.
49. The method of aspect 1, further comprising using said one or more computer processors to identify a characteristic of said tissue using said depth profile.
50. The method of aspect 1, further comprising using said one or more computer processors to identify a disease in said tissue.
51. The method of aspect 50, wherein said disease is identified with an accuracy of at least about 80%.
52. The method of aspect 51, wherein said disease is identified with an accuracy of at least about 90%.
53. The method of aspect 50, wherein said disease is a cancer.
54. The method of aspect 53, wherein said tissue is a skin of said subject, and wherein said cancer is skin cancer.
55. The method of aspect 1, wherein said depth profile has a resolution of at least about 0.8 micrometers.
56. The method of aspect 55, wherein said depth profile has a resolution of at least about 4 micrometers.
57. The method of aspect 56, wherein said depth profile has a resolution of at least about 10 micrometers.
58. The method of aspect 1, further comprising measuring a power of said excitation light beam.
59. The method of aspect 58, further comprising monitoring said power of said excitation light beam in real-time.
60. The method of aspect 58, further comprising using said one or more computer processors to normalize for said power, thereby generating a normalized depth profile.
61. The method of aspect 1, further comprising displaying a projected cross section image of said tissue generated at least in part from said depth profile.
62. The method of aspect 61, further comprising displaying a composite of a plurality of layers of images.
63. The method of aspect 62, wherein each of said plurality of layers is generated by a corresponding depth profile of a plurality of depth profiles.
64. A system for generating a depth profile of a tissue of a subject, comprising:
  an optical probe that is configured to transmit an excitation light beam from a light source to a surface of said tissue, which said excitation light beam, upon contacting said tissue, yield signals indicative of an intrinsic property of said tissue, wherein said optical probe comprises one or more focusing units that are configured to simultaneously adjust a depth and a position of a focal point of said excitation light beam;
  one or more sensors configured to detect at least a subset of said signals; and
  one or more computer processors operatively coupled to said one or more sensors, wherein said one or more computer processors are individually or collectively programmed to process said at least said subset of said signals detected by said one or more sensors to generate a depth profile of said tissue.
65. The system of aspect 64, wherein said excitation light beam is a pulsed light beam.
66. The system of aspect 65, wherein said pulsed light beam is a single beam of light.

67. The system of aspect 64, wherein said one or more focusing units comprise a z-axis scanner and a micro-electro-mechanical-system (MEMS) mirror.
68. The system of aspect 67, wherein said z-axis scanner comprises one or more lenses.
69. The system of aspect 68, wherein at least one of said one or more lenses is an afocal lens.
70. The system of aspect 67, wherein said z-axis scanner comprises an actuator.
71. The system of aspect 70, wherein said actuator comprises a voice coil.
72. The system of aspect 70, wherein said z-axis scanner and said MEMS mirror are separately actuated by two or more actuators controlled by said one or more computer processors.
73. The system of aspect 72, wherein said one or more computer processors are programmed or otherwise configured to synchronize movement of said z-axis scanner and said MEMS mirror.
74. The system of aspect 73, wherein said synchronized movement of said z-axis scanner and said MEMS mirror provides synchronized movement of one or more focal points at a slant angle.
75. The system of aspect 64, wherein said signals comprises at least one signal selected from the group consisting of a second harmonic generation (SHG) signal, a multi photon fluorescence signal, and a reflectance confocal microscopy (RCM) signal.
76. The system of aspect 75, wherein said multi photon fluorescence signal comprises a plurality of multi photon fluorescence signals.
77. The system of aspect 75, wherein said signals comprise at least two signals selected from the group consisting of a SHG signal, a multi photon fluorescence signal, and an RCM signal.
78. The system of aspect 77, wherein said signals comprise a SHG signal, a multi photon fluorescence signal, and an RCM signal.
79. The system of aspect 64, wherein said tissue is epithelial tissue, and wherein said depth profile facilitates identification of a disease in said epithelial tissue of said subject.
80. The system of aspect 64, wherein said depth and said position of said focal point of said excitation light beam are adjusted along a scanning path.
81. The system of aspect 80, wherein said scanning path is a slanted scanning path.
82. The system of aspect 81, wherein said slanted scanning path is a slanted plane positioned along a direction that is angled with respect to an optical axis of said optical probe.
83. The system of aspect 82, wherein an angle between said slanted plane and said optical axis is between 0 degrees to 90 degrees.
84. The system of aspect 64, wherein said light source comprises an ultra-fast pulse laser with a pulse duration less than about 200 femtoseconds.
85. The system of aspect 64, wherein, during use, said optical probe is in contact with said surface of said tissue.
86. The system of aspect 64, further comprising a sensor that detects a displacement between said optical probe and said surface of said tissue.
87. The system of aspect 64, wherein said optical probe is configured to receive at least one of said subset of said signals, wherein at least one of said subset of said signals comprises at least one RCM signal.
88. The system of aspect 87, wherein said optical probe comprises a selective optic configured to send said at least one of said subset of said signals into a fiber optic element.
89. The system of aspect 88, wherein said optical probe comprises an alignment arrangement configured to focus and align said at least one of said subset of signals into said fiber optic element.
90. The system of aspect 89, wherein said alignment arrangement comprises a focusing lens and an adjustable refractive element between said focusing lens and said fiber optic element.
91. The system of aspect 90, wherein said focusing lens and said fiber optic element are in a fixed position with respect to said adjustable refractive element.
92. The system of aspect 91, wherein said adjustable refractive element is angularly moveable.
93. The system of aspect 92, wherein said adjustable refractive element further comprises at least one adjustment element.
94. The system of aspect 90, further comprising a moveable mirror, wherein the focusing lens is positioned between the moveable mirror and the refractive element.
95. The system of aspect 90, further comprising a polarizing selective optic positioned between a beam splitter and the focusing lens.
96. The system of aspect 88, wherein said selective optic comprises an optical filter selected from the group consisting of a beam splitter, a polarizing beam splitter, a notch filter, a dichroic mirror, a long pass filter, a short pass filter, a bandpass filter, and a response flattening filter.
97. The system of aspect 87, wherein said at least said subset of said signals comprises polarized light.
98. The system of aspect 97, wherein said optical probe comprises one or more polarization selective optics which select a polarization of said polarized light.
99. The system of aspect 98, wherein said at least said subset of said signals comprises an RCM signal from a polarization of said polarized light.
100. The system of aspect 87, wherein said at least said subset of signals comprise unpolarized light.
101. The system of aspect 87, wherein said optical probe is configured to reject out of focus light.
102. The system of aspect 64, wherein said one or more sensors comprises one or more photosensors.
103. The system of aspect 64, further comprising a marking tool for outlining a boundary that is indicative of a location of said disease in said tissue of said subject.
104. The system of aspect 64, wherein said system is a portable system.
105. The system of aspect 104, wherein said portable system is less than or equal to 50 pounds.
106. The system of aspect 64, wherein said optical probe comprises a housing configured to interface with a hand of a user.
107. The system of aspect 106, wherein said housing further comprises a sensor within said housing.
108. The system of aspect 107, wherein said sensor is configured to locate said optical probe in space.
109. The system of aspect 108, wherein said sensor is an image sensor, wherein said image sensor is configured to locate said optical probe in space by tracking one or more features.

110. The system of aspect 109, wherein said one or more features comprise features of said tissue of said subject.
111. The system of aspect 109, wherein said one or more features comprise features of a space wherein said optical probe is used.
112. The system of aspect 109, wherein said image sensor is a video camera.
113. The system of aspect 106, wherein said system further comprises an image sensor adjacent to said housing.
114. The system of aspect 113, wherein said image sensor locates said optical probe in space.
115. The system of aspect 114, wherein said one or more features comprise features of said tissue of said subject.
116. The system of aspect 113, wherein said one or more features comprise features of a space wherein said optical probe is used.
117. The system of aspect 64, further comprising a power sensor optically coupled to said excitation light beam.
118. The system of aspect 64, wherein said depth profile has a resolution of at least about 0.8 micrometers.
119. The system of aspect 116, wherein said depth profile has a resolution of at least about 4 micrometers.
120. The system of aspect 119, wherein said depth profile has a resolution of at least about 10 micrometers.
121. The system of aspect 62, wherein said depth profile is an in vivo depth profile.
122. The system of aspect 64, wherein said depth profile is an annotated depth profile.
123. The system of aspect 64, wherein said depth profile comprises a plurality of depth profiles.
124. The system of aspect 64, wherein said one or more computer processors are programmed to display a projected cross section image of tissue.
125. A method for analyzing tissue of a body of a subject, comprising:
  (a) directing light to said tissue of said body of said subject;
  (b) receiving a plurality of signals from said tissue of said body of said subject in response to said light directed thereto in (a), wherein at least a subset of said plurality of signals are from within said tissue;
  (c) inputting data corresponding to said plurality of signals to a trained machine learning algorithm that processes said data to generate a classification of said tissue of said body of said subject; and
  (d) outputting said classification on a user interface of an electronic device of a user.
126. The method of aspect 125, wherein said data comprises at least one depth profile.
127. The method of aspect 126, wherein said at least one depth profile comprises one or more layers.
128. The method of aspect 127, wherein said one or more layers are synchronized in time and location.
129. The method of aspect 126, wherein said depth profile comprises one or more depth profiles synchronized in time and location.
130. The method of aspect 126, wherein said plurality of signals are generated substantially simultaneously by said light.
131. The method of aspect 126, wherein said depth profile comprises an annotated depth profile.
132. The method of aspect 126, wherein said depth profile comprises an in-vivo depth profile.
133. The method of aspect 126, wherein said trained machine learning algorithm comprises an input layer, to which said data is presented; one or more internal layers; and an output layer.
134. The method of aspect 133, wherein said input layer includes a plurality of said depth profiles using data processed from one or more signals that are synchronized in time and location.
135. The method of aspect 134, wherein said depth profiles are generated using said optical probe.
136. The method of aspect 134, wherein said depth profiles comprise individual components, images, or depth profiles generated from a plurality of said subsets of signals.
137. The method of aspect 134, wherein said depth profile comprises a plurality of layers generated from a plurality of subsets of images collected from the same location and time.
138. The method of aspect 134, wherein each of a plurality of layers comprises data that identifies different characteristics than those of the other layers.
139. The method of aspect 134, wherein said depth profiles comprise a plurality of sub-set depth profiles.
140. The method of aspect 125, wherein said classification identifies features of said tissue in said subject pertaining to a property of said tissue selected from the group consisting of health, function, treatment, and appearance.
141. The method of aspect 125, wherein said classification identifies said subject as having a disease.
142. The method of aspect 141, wherein said disease is a cancer.
143. The method of aspect 142, wherein said tissue is a skin of said subject, and wherein said cancer is skin cancer.
144. The method of aspect 125, wherein said plurality of signals comprise at least one signal selected from the group consisting of an SHG signal, a multi photon fluorescence signal, and an RCM signal.
145. The method of aspect 144, wherein said plurality of signals comprise at least two signals selected from the group consisting of a SHG signal, a multi photon fluorescence signal, and an RCM signal.
146. The method of aspect 145, wherein said plurality of signals comprise a SHG signal, a multi photon fluorescence signal, and an RCM signal.
147. The method of aspect 144, wherein said multi photon fluorescence signal comprises one or more multi photon fluorescence signals.
148. The method of aspect 144, wherein (c) comprises identifying one or more features corresponding to said plurality of signals using said trained machine learning algorithm.
149. The method of aspect 125, wherein said trained machine learning algorithm comprises a neural network.
150. The method of aspect 149, wherein said neural network comprises an input layer, to which data is presented.
151. The method of aspect 150, wherein said neural network further comprises one or more internal layers and an output layer.
152. The method of aspect 150, wherein said input layer comprises a plurality of depth profiles generated using at least a subset of said plurality of signals synchronized in time and location.
153. The method of aspect 152, wherein at least one of said plurality of depth profiles is generated using said optical probe, wherein said optical probe comprises one or more focusing units, wherein said one or more focusing units comprise a z-axis scanner and a MEMS mirror.

154. The method of aspect 152, wherein at least one of said plurality of depth profiles comprises individual components from a plurality of subsets of said plurality of signals.

155. The method of aspect 152, wherein at least one depth profile of said plurality of depth profiles comprises a plurality of layers generated from optical data collected from the same location and time.

156. The method of aspect 155, wherein each of said plurality of layers comprises data that identifies a different characteristic than those of another layers.

157. The method of aspect 152, wherein said depth profile comprises a plurality of sub-set depth profiles.

158. The method of aspect 149, wherein said neural network comprises a convolutional neural network.

159. The method of aspect 125, wherein said data is controlled for an illumination power of said optical signal.

160. The method of aspect 125, further comprising receiving medical data of said subject.

161. The method of aspect 160, wherein said medical data of said subject comprises at least one medical data selected from the group consisting of a physical condition, medical history, current and past occupations, age, sex, race, and nationally of said subject.

162. The method of aspect 161, wherein said physical condition comprises vital signs of said subject.

163. The method of aspect 161, wherein said medical data comprises at least one medical data selected from the group consisting of structured data, time-series data, unstructured data, and relational data.

164. The method of aspect 161, wherein said medical data is uploaded to a cloud-based database.

165. The method of aspect 160, wherein said data comprises at least one medical data selected from the group consisting of structured data, time-series data, unstructured data, and relational data.

166. The method of aspect 160, wherein said data is uploaded to a cloud-based database.

167. The method of aspect 160, wherein said data is kept on a local device.

168. The method of aspect 125, wherein said data comprises depth profiles taken of overlapping regions of said tissue.

169. A system for analyzing tissue of a body of a subject, comprising:
an optical probe that is configured to (i) direct an excitation light beam to said tissue of said body of said subject, and (ii) receive a plurality of signals from said tissue of said body of said subject in response to said light excitation beam directed thereto in (i), wherein at least a subset of said plurality of signals are from within said tissue; and
one or more computer processors operatively coupled to said optical probe, wherein said one or more computer processors are individually or collectively programmed to (i) receive data corresponding to said plurality of signals, (ii) input said data to a trained machine learning algorithm that processes said data to generate a classification of said tissue of said body of said subject, and (iii) output said classification on a user interface of an electronic device of a user.

170. The system of aspect 169, wherein said excitation light beam is a pulsed light beam.

171. The system of aspect 170, wherein said pulsed light beam is a single beam of light.

172. The system of aspect 169, wherein said data comprises at least one depth profile.

173. The system of aspect 172, wherein said at least one depth profile comprises one or more layers.

174. The system of aspect 173, wherein said one or more layers are synchronized in time and location.

175. The system of aspect 172, wherein said depth profile comprises one or more depth profiles synchronized in time and location.

176. The system of aspect 172, wherein said depth profile comprises an annotated depth profile.

177. The system of aspect 172, wherein said depth profile comprises an in-vivo depth profile.

178. The system of aspect 172, wherein said trained machine learning algorithm comprises an input layer, to which said data is presented; one or more internal layers; and an output layer.

179. The system of aspect 178, wherein said input layer includes a plurality of said depth profiles using data processed from one or more signals that are synchronized in time and location.

180. The system of aspect 179, wherein said depth profiles are generated using said optical probe.

181. The system of aspect 169, wherein said optical probe comprises one or more focusing units.

182. The system of aspect 181, wherein said one or more focusing units comprise a z-axis scanner and a micro-electro-mechanical-system (MEMS) mirror.

183. The system of aspect 182, wherein said z-axis scanner comprises one or more lenses.

184. The system of aspect 183, wherein at least one of said one or more lenses is an afocal lens.

185. The system of aspect 182, wherein said z-axis scanner comprises an actuator.

186. The system of aspect 185, wherein said actuator comprises a voice coil.

187. The system of aspect 185, wherein said z-axis scanner and said MEMS mirror are separately actuated by two or more actuators controlled by said one or more computer processors.

188. The system of aspect 187, wherein said one or more computer processors are programmed or otherwise configured to synchronize movement of said z-axis scanner and said MEMS mirror.

189. The system of aspect 188, wherein said synchronized movement of said z-axis scanner and said MEMS mirror provides synchronized movement of focal points at a slant angle.

190. The system of aspect 169, wherein said optical probe and said one or more computer processors are in a same device.

191. The system of aspect 190, wherein said device is a mobile device.

192. The system of aspect 169, wherein said optical probe is part of a device, and wherein said one or more computer processors are separate from said device.

193. The system of aspect 192, wherein said one or more computer processors are part of a computer server.

194. The system of aspect 192, wherein said one or more computer processors are part of a distributed computing infrastructure.

195. The system of aspect 169, wherein said one or more computer processors are programmed to receive medical data of said subject.

196. The system of aspect 195, wherein said medical data of said subject comprises at least one medical data selected from the group consisting of a physical condition, medical history, current and past occupations, age, sex, race, and nationally of said subject.

197. The system of aspect 196, wherein said physical condition comprises vital signs of said subject.

198. The system of aspect 195, wherein said medical data comprises at least one medical data selected from the group consisting of structured data, time-series data, unstructured data, and relational data.

199. The system of aspect 169, wherein said data comprises at least one medical data selected from the group consisting of structured data, time-series data, unstructured data, and relational data.

200. A method for generating a trained algorithm for identifying a characteristic in a tissue of a subject, comprising:
   (a) collecting signals from training tissues of subjects that have been previously or subsequently identified as having said characteristic;
   (b) processing said signals to generate data corresponding to depth profiles of said training tissues of said subjects; and
   (c) using said data from (b) to train a machine learning algorithm to yield a trained algorithm in computer memory for identifying said characteristic in said tissue of said subject wherein said tissue is independent of said training tissues.

201. The method of aspect 200, wherein said characteristic is a disease.

202. The method of aspect 200, wherein said characteristic is a characteristic corresponding to a property of said tissue selected from the group consisting of a health, function, treatment, and appearance of the tissue.

203. The method of aspect 200, wherein said data comprises data having a consistent labeling and consistent properties.

204. The method of aspect 203, wherein said consistent properties comprise properties selected from the group consisting of illumination intensity, contrast, color, size, and quality.

205. The method of aspect 203, wherein said data is normalized with respect to an illumination intensity.

206. The method of aspect 203, wherein said depth profiles correspond to different positions of an optical probe on said tissue.

207. The method of aspect 200, wherein (a) comprises generating one or more depth profiles using at least a subset of said signals.

208. The method of aspect 207, wherein said at least said subset of said signals is synchronized in time and location.

209. The method of aspect 207, wherein said data correspond to said one or more depth profiles.

210. The method of aspect 207, wherein at least one of said one or more depth profiles comprises a plurality of layers.

211. The method of aspect 210, wherein said plurality of layers is generated from a plurality of subsets of images collected at the same time and location.

212. The method of aspect 210, wherein each of the plurality of layers comprises data that identifies a different characteristics than that of another layer.

213. The method of aspect 207, wherein each of said one or more depth profiles comprises a plurality of sub-set depth profiles.

214. The method of aspect 213, further comprising training said machine learning algorithm using each of said plurality of sub-set depth profiles individually.

215. The method of aspect 213, further comprising generating a composite depth profile using said plurality of sub-set depth profiles.

216. The method of aspect 215, further comprising using said composite depth profile to train said machine learning algorithm.

217. The method of aspect 207, further comprising generating said one or more depth profiles using a first set of signals collected from a first region of a training tissue and a second set of signals from a second region of said training tissue.

218. The method of aspect 217, wherein said first region of said training tissue is different from said second region of said training tissue.

219. The method of aspect 217, wherein said first region of said training tissue has said disease.

220. The method of aspect 200, wherein said signals comprise two or more signals.

221. The method of aspect 220, wherein said two or more signals are selected from the group consisting of a second harmonic generation (SHG) signal, a multi photon fluorescence signal, and a reflectance confocal microscopy (RCM) signal.

222. The method of aspect 220, wherein said two or more signals are substantially simultaneous signals of a single region of said tissue.

223. The method of aspect 220, wherein said two or more signals are processed and combined to generate a composite image.

224. A system for generating a trained algorithm for identifying a characteristic in a tissue of a subject, comprising:
   a database comprising data corresponding to depth profiles of training tissues of subjects that have been previously or subsequently identified as having said characteristic, which depth profiles are generated from processing signals collected from said training tissues; and
   one or more computer processors operatively coupled to said database, wherein said one or more computer processors are individually or collectively programmed to (i) retrieve said data from said database and (ii) use said data to train a machine learning algorithm to yield a trained algorithm in computer memory for identifying said characteristic in said tissue of said subject wherein said tissue is independent of said training tissues.

225. The system of aspect 224, wherein said characteristic is a disease.

226. The system of aspect 224, wherein said characteristic corresponds to a characteristic of said tissue selected from the group consisting of a health, function, treatment, and appearance.

227. The system of aspect 224, wherein said one or more computer processors are programmed to receive optical data of one or more depth profiles.

228. The system of aspect 224, wherein said depth profiles are generated using signals collected from said training tissues.

229. The system of aspect 228, wherein said signals are synchronized in time and location.

230. The system of aspect 228, wherein said depth profiles comprise a plurality of layers.

231. The system of aspect 230, wherein said plurality of layers is generated from a plurality of subsets of images collected at the same time and location.

232. The system of aspect 230, wherein each of said plurality of layers comprises data that identifies a different characteristic than that of another layer.

233. The system of aspect 224, wherein said one or more computer processors are programmed to receive medical data of said subject.

234. The system of aspect 233, wherein said medical data comprises at least one medical data selected from the group consisting of structured data, time-series data, unstructured data, and relational data.

235. The system of aspect 224, wherein said data comprises structured data, time-series data, unstructured data, relational data, or any combination thereof.

236. A method for aligning a light beam, comprising:
   (a) providing (i) a light beam in optical communication with a lens, wherein said lens is in optical communication with a refractive element, (ii) an optical fiber, and (iii) a detector in optical communication with said optical fiber, wherein said refractive element is positioned between said lens and said optical fiber; and
   (b) adjusting said refractive element to align said optical path with said optical fiber, wherein said optical path is thereby aligned with said optical fiber.

237. The method of aspect 236, wherein a point spread function of a beamlet after interacting with said refractive element is sufficiently small to enable a resolution of said detector to be less than 1 micrometer.

238. The method of aspect 236, wherein said adjusting said position comprises applying a rotation to said refractive element.

239. The method of aspect 238, wherein said rotation is at most a 180° rotation.

240. The method of aspect 238, wherein said rotation is a rotation in at most two dimensions.

241. The method of aspect 240, wherein said rotation is a rotation in one dimension.

242. The method of aspect 240, further comprising providing an adjustable mirror wherein said lens is fixed between said adjustable mirror and said adjustable refractive element and adjusting said adjustable mirror aligns said optical path prior to using said adjustable refractive element.

243. The method of aspect 240, wherein said providing said light beam comprises providing a generated light signal from an interaction with a tissue of a subject.

244. The method of aspect 243, wherein said tissue is an in vivo skin tissue.

245. A system for aligning a light beam, comprising:
   a light source that is configured to provide a light beam;
   a focusing lens in optical communication with said light source;
   an adjustable refractive element in optical communication with said lens;
   an optical fiber; and
   a detector in optical communication with said optical fiber, wherein the adjustable refractive element is positioned between the focusing lens and the optical fiber and is moveable to align an optical path between the focusing lens and said optical fiber.

246. The system of aspect 245, wherein said focusing lens and said optical fiber are fixed with respect to said adjustable refractive element.

247. The system of aspect 245, wherein said adjustable refractive element is angularly moveable.

248. The system of aspect 245, further comprising adjustment elements coupled to said adjustable refractive element, wherein said adjustment elements are configured to adjust a position of said adjustable refractive element.

249. The system of aspect 248, wherein said adjustment elements angularly move said adjustable refractive element.

250. The system of aspect 245, further comprising a controller operatively coupled to said refractive element, wherein said controller is programmed to direct adjustment of said refractive element to align said optical path with said optical fiber.

251. The system of aspect 250, wherein said adjustment is performed without an input of a user.

252. The system of aspect 250, wherein said adjustment is performed by a user.

253. The system of aspect 245, further comprising a beam splitter configured to direct light along said optical path towards said optical fiber.

254. The system of aspect 253, further comprising a moveable mirror positioned between said beam splitter and said focusing lens.

255. The system of aspect 253, further comprising a polarization selective optic positioned on said optical path.

256. The system of aspect 255, wherein said polarization selective optic is positioned between said beam splitter and said focusing lens.

257. The system of aspect 245, wherein said refractive element is a flat window.

258. The system of aspect 245, wherein said refractive element is a glass refractive element.

259. The system of aspect 245, wherein a point spread function of a beamlet of light after interacting with said refractive element is sufficiently small to enable a resolution of said detector to be less than 1 micrometer.

260. The system of aspect 245, wherein said refractive element has a footprint of less than 1,000 mm$^2$.

261. The system of aspect 245, wherein said refractive element is configured to adjust a beamlet of light at most about 10 degrees.

262. The system of aspect 245, wherein said refractive element has a has a property that permits alignment of a beam of light exiting said lens to a fiber optic.

263. The system of aspect 262, wherein said diameter is less than about 20 microns.

264. The system of aspect 263, wherein said diameter is less than about 10 microns.

265. The system of aspect 264, wherein said fiber optic has a diameter of less than about 5 microns.

266. The system of aspect 262, wherein said property is at least one property selected from the group consisting of a refractive index, a thickness, and a range of motion.

267. The system of aspect 245, wherein an aberration introduced by said refractive element is less than 20% of a diffraction limit of said focusing lens.

268. The system of aspect 267, wherein said aberration is less than 10% of said diffraction limit.

269. The system of aspect 268, wherein said aberration is less than 5% of said diffraction limit.

270. The system of aspect 269, wherein said aberration is less than 2% of said diffraction limit.

271. The system of aspect 270, wherein said aberration is less than 1% of said diffraction limit.

272. A method for aligning a light beam, comprising:
  a. providing (i) a light beam in optical communication with a beam splitter, wherein said beam splitter is in optical communication with a lens, wherein said lens is in optical communication with a refractive element, (ii) an optical fiber, and (iii) a detector in optical communication with said optical fiber, wherein an optical path from said refractive element is misaligned with respect to said optical fiber;
  b. adjusting said refractive element to align said optical path with said optical fiber; and
  c. directing said light beam to said beam splitter that splits said light beam into a beamlet, wherein said beamlet is directed through said lens to said refractive element that directs said beamlet along said optical path to said optical fiber, such that said detector detects said beamlet.

273. A system for aligning a light beam, comprising:
  a light source that is configured to provide a light beam;
  a beam splitter in optical communication with said light source;
  a lens in optical communication with said beam splitter;
  a refractive element in optical communication with said lens;
  an optical fiber; and
  a detector in optical communication with said optical fiber, wherein an optical path from said refractive element is misaligned with respect to said optical fiber,
  wherein said refractive element is adjustable to align said optical path with said optical fiber, such that, when said optical path is aligned with said optical fiber, said light beam is directed from said light source to said beam splitter that splits said light beam into a beamlet, wherein said beamlet is directed through said lens to said refractive element that directs said beamlet along said optical path to said optical fiber, such that said detector detects said beamlet.

What is claimed is:

1. A method for generating a depth profile of a tissue of a subject, comprising:
  (a) using an optical probe, comprising one or more focusing units, to transmit an excitation light beam from a light source to a surface of said tissue, which pulses of said excitation light beam, upon contacting said tissue, yield one or more signals;
  (b) detecting, via said optical probe, at least a subset of said one or more signals, wherein a point spread function of said subset of said one or more signals is sufficiently small to enable a resolution of less than 200 microns; and
  (c) using one or more computer processors programmed to process said at least said subset of said one or more signals detected in (b) to generate said depth profile of said tissue,
  wherein said one or more focusing units simultaneously adjust a depth and a position of a focal point of said excitation light beam along a slanted path forming a slanted plane positioned along a direction angled with respect to an optical axis of said optical probe.

2. The method of claim 1, wherein (b) further comprises simultaneously detecting a plurality of subsets of said one or more signals.

3. The method of claim 2, further comprising processing said plurality of subsets of said one or more signals to generate a plurality of depth profiles, wherein said plurality of depth profiles correspond to a probe position at a time of detecting said one or more signals.

4. The method of claim 3, wherein said plurality of depth profiles corresponds to a same scanning path.

5. The method of claim 3, further comprising assigning a least one distinct color for each of said plurality of depth profiles.

6. The method of claim 3, further comprising combining at least a subset of data from said plurality of depth profiles to form a composite depth profile.

7. The method of claim 6, further comprising displaying, on a display screen, a composite image derived from said composite depth profile, wherein said composite image is a polychromatic image.

8. The method of claim 1, wherein said depth profile comprises a plurality of layers created from a plurality of subsets of images collected from a same location and time, wherein of said plurality of layers comprise data that identifies different characteristics than those of other layers.

9. The method of claim 1, wherein said depth profiles comprises a plurality of sub-set depth profiles, wherein said plurality of sub-set depth profiles comprise optical data from processed one or more signals.

10. The method of claim 3, wherein said plurality of depth profiles comprises a first depth profile and a second depth profile, and wherein said first depth profile comprises data processed from a signal that is different from data generated from a signal comprised in said second depth profile.

11. The method of claim 10, wherein said first depth and said second depth profile comprise at least one processed one or more signals independently selected from the group consisting of a second harmonic generation (SHG) signal, a multi photon fluorescence signal, and a reflectance confocal microscopy (RCM) signal.

12. The method of claim 1, wherein said tissue comprises in vivo tissue.

13. The method of claim 1, wherein said detecting is performed in a presence of ambient light.

14. The method of claim 1, wherein said depth profile has a resolution of at least 0.8 micrometers.

15. The method of claim 1, further comprising displaying a projected cross section image of said tissue generated at least in part from said depth profile, further comprising displaying a composite of a plurality of layers of images, wherein each of said plurality of layers is generated by a corresponding depth profile of a plurality of depth profiles.

16. The method of claim 1, wherein said one or more focusing units comprises an afocal lens arrangement comprising a fixed lens and a mobile lens.

17. The method of claim 1, wherein said optical probe comprises an objective lens and said objective lens is stationary with respect to said tissue or in contact with said tissue.

18. The method of claim 1, wherein said optical probe maintains a constant numerical aperture while said one or more focusing units adjust a depth of said focal point.

19. The method of claim 1, wherein an angle between said slanted plane and said optical axis is between 10 degrees and 80 degrees.

20. The method of claim 1, wherein a point spread function of said subset of one or more signals is sufficiently small to enable a resolution of less than 10 microns.

* * * * *